US007205142B2

(12) United States Patent
Lloyd et al.

(10) Patent No.: US 7,205,142 B2
(45) Date of Patent: Apr. 17, 2007

(54) NUCLEIC ACID SEQUENCE ENCODING OVARIAN ANTIGEN, CA125, AND USES THEREOF

(75) Inventors: Kenneth O. Lloyd, Bronx, NY (US); Beatrice W. T. Yin, Forest Hills, NY (US)

(73) Assignee: Sloan-Kettering Institute for Cancer Research, New York, NY (US)

( * ) Notice: Subject to any disclaimer, the term of this patent is extended or adjusted under 35 U.S.C. 154(b) by 236 days.

(21) Appl. No.: 10/243,243

(22) Filed: Sep. 13, 2002

(65) Prior Publication Data
US 2003/0104442 A1 Jun. 5, 2003

Related U.S. Application Data

(63) Continuation-in-part of application No. 10/142,515, filed on May 9, 2002, now abandoned, and a continuation-in-part of application No. PCT/US02/14768, filed on May 9, 2002.

(60) Provisional application No. 60/290,480, filed on May 11, 2001.

(51) Int. Cl.
C12N 1/20 (2006.01)
(52) U.S. Cl. .................. 435/252.3; 435/325; 435/69.1; 435/320.1; 536/23.1; 536/23.5
(58) Field of Classification Search ............... 536/23.1, 536/23.5; 530/350; 514/44; 435/69.1, 252.3, 435/320.1, 325
See application file for complete search history.

(56) References Cited

OTHER PUBLICATIONS

. McClean and Hill (Eur J of Cancer, 1993, vol. 29A, pp. 2243-2248).*
Fu et al (EMBO Journal, 1996, vol. 15, pp. 4392-4401).*
Yokota, J et al (Oncogene, 1988, vol. 3, pp. 471-475).*
Guo et al (Journal of Pharmacology and Experimental Therapeutics, 2002, vol. 300, pp. 206-212).*
Drexler et al (Leukemia and Lymphoma, 1993, 9:1-25).*
Embleton et al (Immunol Ser, 1984, 23:181-207).*
Hsu (in Tissue Culture Methods and Applications, Kruse and Patterson, Eds, 1973, Academic Press, NY, see abstract, p. 764).*
Freshney (Culture of Animal Cells, A Manual of Basic Technique, Alan R. Liss, Inc., 1983, New York, p. 4).*
Dermer (Bio/Technology, 1994, 12:320).*
Miller (1995, FASEB J., vol. 9, pp. 190-199).*
Deonarain (1998, Expert Opin. Ther. Pat., vol. 8, pp. 53-69).*
Verma (Sep. 1997, Nature, vol. 389, pp. 239-242).*
Crystal (1995, Science, vol. 270, p. 404-410).*
Ezzell (J. NIH Res, 1995, 7:46-49).*

Spitler (Cancer Biotherapy, 1995, 10:1-3).*
Gura (Science, 1997, 278:1041-1042).*
Jain (Sci. Am., 1994, 271:58-65).*
Curti (Crit. Rev. in Oncology/Hematology, 1993, 14:29-39).*
Hartwell et al (Science, 1997, 278:1064-1068).*
Montesano, R et al, 1996, Intl J Cancer, 69(3): 225-235.*
Burmer, GC et al, 1991, Environmental Health perspectives, 93: 27-31.*
Busken, C et al, Digestive Disease Week Abstracts and Itinerary Planner, 2003, abstract No. 850.*
Bowie et al (Science, 1990, 257 : 1306-1310).*
Burgess et al, (Journal of Cell Biology, 1990, 11: 2129-2138.*
Lazar et al. Molecular and Cell Biology, 1988, 8: 1247-1252.*
Tao. et al. The Journal of Immunology, 1989, 143(8): 2595-2601.*
Gillies et al. Human Antibodies and Hybridomas, 1990, 1(1): 47-54.*
Sambrook et al, eds, 1989, 2nd ed, Molecular Cloning, a laboratory manual, Cold Spring Harbor Laboratory Press, Cold Spring Harbor, p. 11.52.*
Roitt et al, 1998, Immunology, 4th ed, Mosby, London, p. 7.7-7.8.*
Holmes (Exp. Opin.Invest. Drugs, 2001, 10(3):511-519).*
Lewin, B, ed, Genes, 1983, John Wiley & Sons, p. 27.*
International Search Report for PCT/US02/14768, filed May 9, 2002 for Sloan-Kettering Institute for Cancer Research, et al., dated Jun. 23, 2005.
Campbell, et al., "A novel gene encoding a B-box protein within the BRCA 1 region at 17q21.1", Human Mol Genet, vol. 3, No. 4, pp. 589-594 (1994).
O'Brien, T. et al. The CA 125 Gene: A Newly Discovered Extension of the Glycosylated N-Terminal Domain Doubles the Size of This Extracellular Superstructure. Tumor Biol. 23:154-169 (2002) [Exhibit 1].
O'Brien, T. et al. The CA 125 Gene: An Extracellular Superstructure Dominated by Repeat Sequences. Tumor Biol., 22:348-366 (2001).
Yin, B.W.T. et al. Ovarian Cancer Antigen CA125 Is Encoded by the *MUC16* Mucin Gene. Int. J. Cancer, 98:737-740 (2002).
Yin, B.W.T. and Lloyd, K.O. Molecular Cloning of the CA125 Ovarian Cancer Antigen. The Journal of Biological Chemistry, vol. 276, No. 29, pp. 27371-27375 (Jul. 20, 2001).

* cited by examiner

Primary Examiner—Susan Ungar
Assistant Examiner—Minh-Tam Davis
(74) Attorney, Agent, or Firm—Law Offices of Albert Wai-Kit Chan, LLC

(57) ABSTRACT

The present invention provides an isolated nucleic acid molecule comprising sequences encoding the CA125 protein or a portion thereof. This invention also provides a method to detect ovarian cancer in a subject. Furthermore, this invention provides a method for the diagnosis of a cancer which expresses CA125 by detecting CA125-expressing cells in the blood or other fluids of patients. This invention also provides a method of producing CA125 protein. This invention also provides a method of silencing CA125 protein production. Finally, this invention provides a method to treat or prevent cancer using a vaccine comprising CA125 nucleic acid or protein.

6 Claims, 18 Drawing Sheets

FIGURE 2

Figure 1:
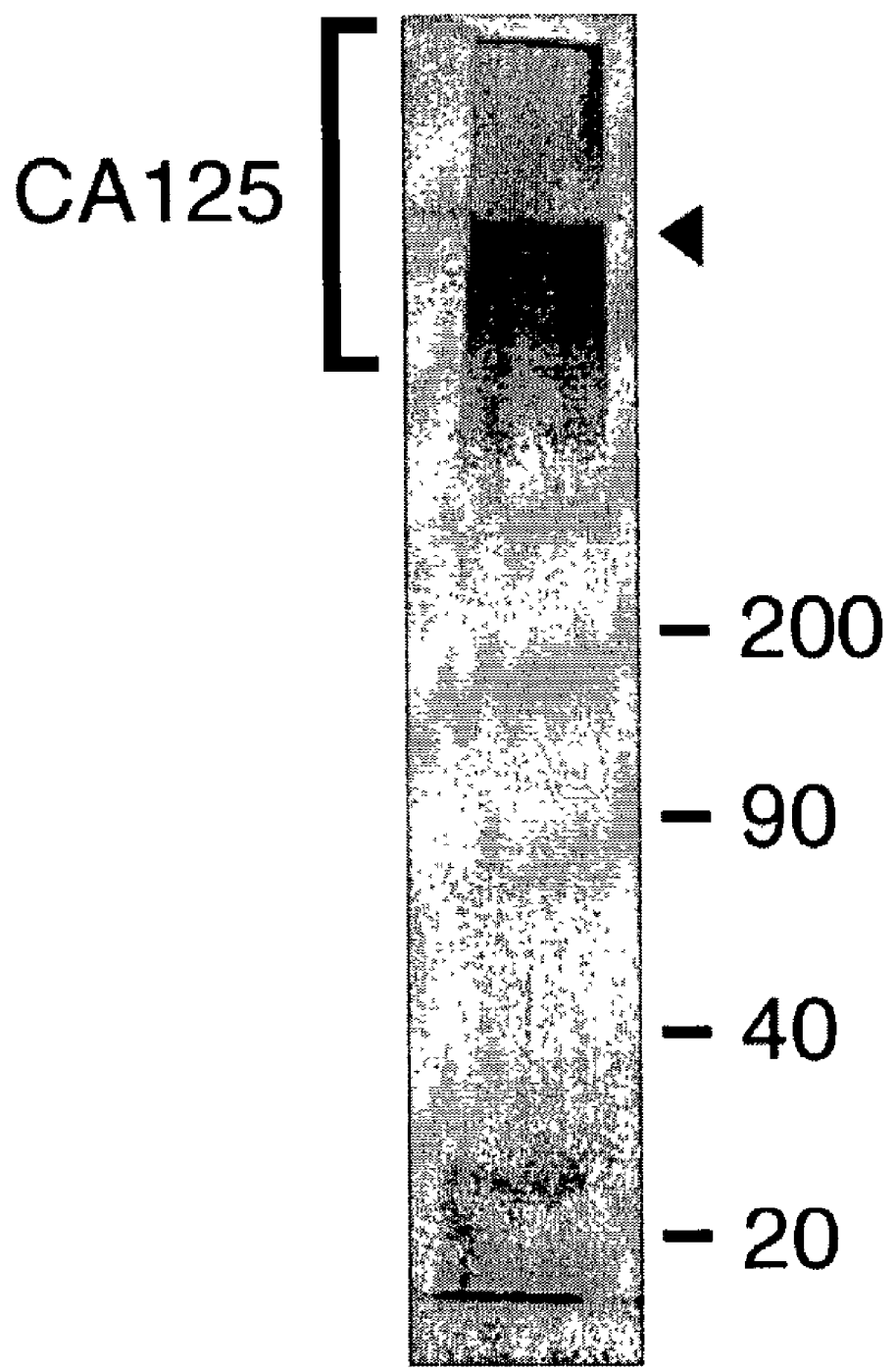

```
Y   Y   Q   S   H   L   D   L   E   D   L   Q   *
TACTACCAGTCACACCTAGACCTGGAGGATCTGCAATGACTGGAACTTGCC           5685

GGTGCCTGGGGTGCCTTTCCCCCAGCCAGGGTCCAAAGAAGCTTGGCTGG            5736

GGCAGAAATAAACCATATTGGTCGGAAAAAGGAAGGAGAATACAACGTCCA           5787

GCAACAGTGCCCAGGCTACTACCAGTCCCCCCTAGACCTGGAGGATTTGCA           5838

ATGACTGGAACTTGCCGGTGCCTGGGGTGCCTTTCCCCCAGCCAGGGTCC            5889

AAAAAAGCTTGGCTGGGGCAAAAATAAACCCATATTGGTCGGAAAAAAAAA           5940

AAAAAAAAAAAAAAAAAAAAAAAAA                                     5965
```

FIGURE 3

```
**  ***  *********  *  ** * ***  *** ****  **   *****  **
                          RVDPIGPGLDRERLYWELSQLTNSITELGPYTLDRDSLYVNG     42
LFKSTSVGPLYSGCRLTLLRPEKHGAATGVDAICTLRLDPTGPGLDRERLYWELSQLTNSVTELGPYTLDRDSLYVNG   198
LFKSTSVGPLYSGCRLTLLRPEKRGAATGVDTICTHRLDPLNPGLDREQLYWELSKLTRGIIELGPYLLDRGSLYVNG   354
LFKNTSIGPLYSGCRLTLLRPEKDKAATGVDTICTHHPDPQSPGLNREQLYWELSQLTHGITELGPYTLDRDSLYVDG   510
LFKSTSVGPLYSGCRLTLLRPEKDGVATRVDAICTHRPDPKIPGLDRQQLYWELSQLTHSITELGPYTLDRDSLYVNG   666
LFKSTSVSSLYSGCRLTLLRPEKDGAATRVDAVCTHRPDPKSPGLDRERLYWKLSQLTHGITELGPYTLDRHSLYVNG   822
VFKNTSVGPLYSGCRLTLLRPKKDGAATKVDAICTYRPDPKSPGLDREQLYWELSQLTHSITELGPYTLDRDSLYVNG   978
LFKSTSVGPLYSGCRLTLLRPEKDGTATGVDAICTHHPDPKSPRLDREQLYWELSQLTHNITELGPYALDNDSLFVNG  1134
LFKNTSVGPLYSGCRLTLLRPEKDGEATGVDAICTHRPDPTGPGLDREQLYLELSQLTHSITELGPYTLDRDSLYVNG  1290

*                              * **   ** ****** **
FNPWSSVPIPGHVHLAISGPSSLPGHHAPVPLLIPFTLNFTITNLHYEENMQHPGSRKFNTTERVLQGLLKP         120
FTHRSSVPIPGHSIPGHSAVHLEISGPASLPGHHAPGPLLVPFTLNFTITNLQYEEDMRHPGSRKFNTTERVLQGLLKP  276
FTHRNFVPIPSHSIPGHSVHLGISEAPSSLPRPIVPGPLLVPFTLNFTITNLQYEEAMRHPGSRKFNTTERVLQGLLRP  432
FTHWSPIPHSIPGHSIVNLGISGIPPSLPEHAGPLLVPFTLNFTITNLQYEENMGHPGSRKFNITESVLQGLLKP     588
FTQRSSMIPHSVPGHFIVQPEISEPSSLPGHAHGPVLLPFTLNFTIINLQYEEDMHRPGSRKFNTTERVLQGLLMP    744
FTHQSSIPGHPDFSTMHLAISRAPASLSGPHASPLLVLFTINFTITNLRYEENMHPGSRKFNTTERVLQGLLRP      900
FTQRSSVPIPGHVDLGIEGAPVSKPGSAASPLLVLFTLNFTITNLRYEENMQHPGSRKFNTTERVLQGLLRS       1056
FTHRSSVPIGHSTAIPGHPVYLGASKHPASIFGPSAASHLLILFTLNFTITNLRYEENMW-PGSRKFNTTERVLQGLLRP  1212
FTHRSSVPIGHSGVVSEE----------PFTLNFTINNLRYMADMGQPGSLKFNITDNVMQHLLSP              1345

LFQRSSLGARYTGCRVIALRSVKNGAETRVDLLCTYLQPLSGPGLPIKQVFHELSQQTHGITRLGPYSLDKDSLYLNG  1423
YNEPGLDEPPTTPKPATTFLPPLSEATTAMGVHLKTLTLNFTISNLQYSPDMGKGSATFNSTEGVLQHLLRPLFQKSS  1501
MGPFYLGCQLISLRPEKDGAATGVDTTCTYHPDPVGPGLDIQQLYWELSQLTHGVTQLGFYVLDRDSLFINGYAPQNL  1579
SIRGEYQINFHIVNWNLSNPDPTSSEYITLLRDIQDKVTTLYKGSQLHDTFRFCLVTNLTMDSVLVTVKALFSSNLDP  1657
SLVEQVFLDKTLNASFHWLGSTYQLVDIHVTEMESSVYQPISSSHQHFYPNFTITNLPYSQDKAQPGTTNYQRNKRN  1735
IEDALNQLFRNSSIKSYFSDCQVSTFRSVPNRHHTGVDSLCNFSPLARRVDRVAIYEEFLRMTRNGTQLQNFTLDRSS 1813
VLVDGYSPNRNEPLTGNSDLPFWAVIFIGLAGLLGLLITCLICGVLVTTRRRKKEGEYNVQQQCPGYYQSHLDLEDLQ 1890
```

FIGURE 5

```
   1 cgcgttgatc ccatcggacc tggactggac agagagcggc tatactggga gctgagccag
  61 ctgaccaaca gcatcacaga gctgggaccc tacaccctgg ataggacag tctctatgtc
 121 aatggcttca acccttggag ctctgtgcca accaccagca ctcctgggac ctccacagtg
 181 cacctggcaa cctctgggac tccatcctcc ctgcctggcc acagccccc tgtccctctc
 241 ttgataccat tcaccctcaa ctttaccatc accaacctgc attatgaaga aacatgcaa
 301 caccctggtt ccaggaagtt caacaccacg gagagggttc tgcagggtct gctcaagccc
 361 ttgttcaaga gcaccagcgt tggccctctg tactctggct gcagactgac cttgctcaga
 421 cctgagaaac atggggcagc cactggagtg gacgccatct gcaccctccg ccttgatccc
 481 actggtcctg gactggacag agcggcta ctgggagc tgagccagct gaccaacagc
 541 gttacagagc tgggcccta caccctggac agggacagtc tctatgtcaa tggcttcacc
 601 catcggagct ctgtgccaac caccagtatt cctgggacct gcagtgca cctggaaacc
 661 tctgggactc cagcctccct ccctggccac acagccctg ccctctcct ggtgccattc
 721 accctcaact tcactatcac caacctgcag tatgaggagg acatgcgtca ccctggttcc
 781 aggaagttca acaccacgga gagtcctg cagggtctgc tcaagccctt gttcaagagc
 841 accagtgttg gccctctgta ctctggctgc agactgacct tgctcaggcc tgaaaaacgt
 901 ggggcagcca ccggcgtgga ccatcctgc actcaccgcc ttgaccctct aaaccctgga
 961 ctggacagag agcagctata ctgggagctg agcaaactga cccgtggcat catcgagctg
1021 ggccctacc tcctggacag aggcagtctc tatgtcaatg gtttcaccca tcggaacttt
1081 gtgcccatca ccagcactcc tgggacctcc acagtacacc taggaacctc tgaaactcca
1141 tcctccctac ctagacccat agtgcctggc cctctcctgg tgccattcac cctcaacttc
1201 accatcacca acttgcagta tgaggaggcc atgcgacacc ctggctccag gaagttcaat
1261 accacggaga gggtcctaca gggtctgctc aggcccttgt caagaatac agtatcggc
1321 cctctgtact ccagctgcag actgaccttg ctcaggccag agaaggacaa ggcagccacc
1381 agagtggatg ccatctgtac ccaccaccct gaccctcaaa gccctggact gaacagagag
1441 cagctgtact gggagctgag ccagctgacc cacggcatca ctgagctggg ccctacacc
1501 ctggacaggg acagtctcta tgtcgatggt tcactcatt ggagcccat accaaccacc
1561 agcactcctg gacctccat agtgaacctg gaacctctg gatcccacc ttccctccct
1621 gaaactacag ccaccggccc tctcctggtg ccattcacac tcaacttcac catcactaac
1681 ctacagtatg aggagaacat gggtcaccct ggctccagga agttcaacat cacggagagt
1741 gttctgcagg gtctgctcaa gcccttgttc aagagcacca gtgttggccc tctgtattct
1801 ggctgcagac tgaccttgct caggcctgag aaggacggag tagccaccag agtggacgcc
1861 atctgcaccc accgccctga ccccaaaatc cctgggctag acagacagca gctatactgg
1921 gagctgagcc agctgaccca cagcatcact gagctgggac cctacaccct ggataggac
1981 agtctctatg tcaatggttt caccagcgg agctctgtgc caccaccag cactcctgg
2041 actttcacag tacagccgga aacctctgag actccatcat ccctccctgg ccccacagcc
2101 actggccctg tcctgctgcc attcaccctc aatttacca tcattaacct gcagtatgag
2161 gaggacatgc atcgcctgg ctccaggaag ttcaacacca cggagagggt ccttcagggt
2221 ctgcttatgc ccttgttcaa gaacaccagt gtcagctctc tgtactctgg ttgcagactg
2281 accttgctca ggcctgagaa ggatgggca gccaccagag tggatgctgt ctgcacccat
2341 cgtcctgacc ccaaaagccc tggactggac agagagcggc tgtactggaa gctgagccag
2401 ctgacccacg gcatcactga gctggcccc tacaccctgg acaggcacag tctctatgtc
2461 aatggtttca cccatcagag ctctatgacg accaccagaa ctcctgatac ctccacaatg
2521 cacctggcaa cctcgagaac tccagcctcc ctgtctggac ctacgaccgc cagccctctc
2581 ctggtgctat tcacaattaa cttcaccatc actaacctgc ggtatgagga aacatgcat
2641 caccctggct ctagaaagtt taacaccacg gagagtcc ttcagggtct gctcaggcct
2701 gtgttcaaga acaccagtgt tggccctctg tactctggct gcagactgac cttgctcagg
2761 cccaagaagg atggggcagc caccaaagtg gatgccatct gcacctaccg ccctgatccc
2821 aaaagccctg gactggacag agcagcta ctgggagc tgagccagct aacccacagc
2881 atcactgagc tgggcccta caccctggac agggacagtc tctatgtcaa tggtttcaca
2941 cagcggagct ctgtgccac actagcatt cctgggaccc cacagtgga cctgggaaca
3001 tctgggactc cagtttctaa acctggtccc tcggctgcca gccctctcct ggtgctattc
3061 actctcaact tcaccatcac caacctgcgg tatgaggaga acatgcagca cctggctcc
3121 aggaagttca acaccacgga gagggtcctt caggcctgc tcaggtccct gttcaagagc
3181 accagtgttg gccctctgta ctctggctgc agactgactt tgctcaggcc tgaaaaggat
```

FIGURE 5

(cont.)

```
3241 gggacagcca ctggagtgga tgccatctgc acccaccacc ctgaccccaa aagccctagg
3301 ctggacagag agcagctgta ttgggagctg agccagctga cccacaatat cactgagctg
3361 ggcccctatg ccctggacaa cgacagcctc tttgtcaatg gtttcactca tcggagctct
3421 gtgtccacca ccagcactcc tgggaccccc acagtgtatc tgggagcatc taagactcca
3481 gcctcgatat ttggcccttc agctgccagc catctcctga tactattcac cctcaacttc
3541 accatcacta acctgcggta tgaggagaac atgtggcctg gctccaggaa gttcaacact
3601 acagagaggg tccttcaggg cctgctaagg cccttgttca agaacaccag tgttggccct
3661 ctgtactctg gctgcaggct gaccttgctc aggccagaga agatgggga agccaccgga
3721 gtggatgcca tctgcaccca ccgcctgac cccacaggcc tgggctgga cagagagcag
3781 ctgtatttgg agctgagcca gctgacccac agcatcactg agctgggccc ctacacactg
3841 gacagggaca gtctctatgt caatggtttc acccatcgga gctctgtacc caccaccagc
3901 accggggtgg tcagcgagga gccattcaca ctgaacttca ccatcaacaa cctgcgctac
3961 atggcggaca tgggccaacc cggctccctc aagttcaaca tcacagacaa cgtcatgcag
4021 cacctgctca gtcctttgtt ccagaggagc agcctgggtg cacggtacac aggctgcagg
4081 gtcatcgcac taaggtctgt gaagaacggt gctgagacac gggtggacct cctctgcacc
4141 tacctgcagc ccctcagcgg cccaggtctg cctatcaagc aggtgttcca tgagctgagc
4201 cagcagaccc atggcatcac ccggctgggc ccctactctc tggacaaaga cagcctctac
4261 cttaacggtt acaatgaacc tggtccagat gagcctccta caactcccaa gccagccacc
4321 acattcctgc ctcctctgtc agaagccaca acagccatgg gtaccacct gaagaccctc
4381 acactcaact tcaccatctc caatctccag tattcaccag atatgggcaa gggctcagct
4441 acattcaact ccaccgaggg ggtccttcag cacctgctca gacccttgtt ccagaagagc
4501 agcatgggcc ccttctactt gggttgccaa ctgatctccc tcaggcctga gaaggatggg
4561 gcagccactg gtgtggacac cacctgcacc taccacctg accctgtggg ccccgggctg
4621 gacatacagc agctttactg ggagctgagt cagctgaccc atggtgtcac ccaactgggc
4681 ttctatgtcc tggacaggga tagcctcttc atcaatggct atgcaccca gaatttatca
4741 atccggggcg agtaccagat aaatttccac attgtcaact ggaacctcag taatccagac
4801 cccacatcct cagagtacat cacccctgctg agggacatcc aggacaaggt caccacactc
4861 tacaaaggca gtcaactaca tgacacattc cgcttctgcc tggtcaccaa cttgacgatg
4921 gactccgtgt tggtcactgt caaggcattg ttctcctcca atttggaccc cagcctggtg
4981 gagcaagtct ttctagataa gaccctgaat gcctcattcc attggctggg ctccacctac
5041 cagttggtgg acatccatgt gacagaaatg gagtcatcag tttatcaacc aacaagcagc
5101 tccagcaccc agcacttcta cccgaatttc accatcacca acctaccata ttcccaggac
5161 aaagcccagc caggcaccac caattaccag aggaacaaaa ggaatattga ggatgcgctc
5221 aaccaactct tccgaaacag cagcatcaag agttattttt ctgactgtca agtttcaaca
5281 ttcaggtctg tccccaacag gcaccacacc ggggtggact ccctgtgtaa cttctcgcca
5341 ctggctcgga gagtagacag agttgccatc tatgaggaat ttctgcggat gacccggaat
5401 ggtacccagc tgcagaactt caccctggac aggagcagtg tccttgtgga tgggtattct
5461 cccaacagaa atgagccctt aactgggaat tctgaccttc ccttctgggc tgtcatcttc
5521 atcggcttgg caggactcct gggactcatc acatgcctga tctgcggtgt cctggtgacc
5581 acccgccggc ggaagaagga aggagaatac aaagtccagc aacagtgccc aggctactac
5641 cagtcacacc tagacctgga ggatctgcaa tgactggaac ttgccggtgc tggggtgcc
5701 tttcccccag ccagggtcca agaagcttg gctggggcag aaataaacca tattggtcgg
5761 aaaaaggaag gagaatacaa cgtccagcaa cagtgcccag gctactacca gtccccccta
5821 gacctggagg atttgcaatg actggaactt gccggtgcct ggggtgcctt cccccagcc
5881 agggtccaaa aaagcttggc tggggcaaaa ataaaccata ttggtcggaa aaaaaaaaa
5941 aaaaaaaaaa aaaaaaaaaa aaaaa
```

FIGURE 7

```
      E   Y   S   T   D   V   P   M   A   P   I   L   Q   Q   T   *
TGAGTATTCTACTGATGTTCCCATGGCCCCAATCTTACAACAAACTTAGCAGGAGCTGACCCCTATTCAT
AAGCCCTTATGTCCTTTCCATAAGGGAAGGAACATAGAGGACACAAATTATTCCCCTTCCCCACTGCCCC
AGCTAATCAGAGTCCCAGCTGAAGCCCCACAGGCAAAAATCCCCATGAATAGTCCCTCCTGCTGGCATTA
CNTTCCATGAGAGCACNTTGCTCCTTTCACTGTTGAGGGCTTCTCCTCAGCTCCTGGGACTTTCACAGTA
CAGCCGGAAACCTCTGAGACTCCATCATCCCTCCCTGGCCCCACAGGTAAATACCAGTCAATGGTATTTG
GAGCATGGTTGATGAGTGTAAACATCTCTGTTTATACTCTGTTAGAGCATGGTTGATGAGTGTAAACATC
TCTGTCATTATTCACTCAACTAAAGATGGAAATTCATAGTAAATGTAGTAACCATAGGTCAACCAACCCA
GTTCATTGAGCACTGCCTCTGTATCAGGACCTGGATATACATCAGGGAACAAAAAAAAAAAAAAAAAA
```

FIGURE 8

```
CCTGTGACTTCTCTTCTCACCCCTGGCCTGGTGATAACCACAGACAGGATGGGCATAAGCAGAGAACCTGGAAC
CAGTTCCACTTCAAATTTGAGCAGCACCTCCCATGAGAGACTGACCACTTTGGAAGACACTGTAGATACAGAAG
CCATGCAGCCTTCCACACACACAGCAGTGACCAACGTGAGGACCTCCATTTCTGGACATGAATCACAATCTTCT
GTCCTATCTGACTCAGAGACACCCAAAGCCACATCTCCAATGGGTACCACCTACACCATGGGGGAAACGAGTGT
TTCCATATCCACTTCTGACTTCTTTGAGACCAGCAGAATTCAGATAGAACCAACATCCTCCCTGACTTCTGGAT
TGAGGGAGACCAGCAGCTCTGAGAGGATCAGCTCAGCCACAGAGGGAAGCACTGTCCTTTCTGAAGTGCCCAGT
GGTGCTACCACTGAGGTCTCCAGGACAGAAGTGATATCCTCTAGGGGAACATCCATGTCAGGGCCTGATCAGTT
CACCATATCACCAGACATCTCTACTGAAGCGATCACCAGGCTTTCTACTTCCCCCATTATGACAGAATCAGCAG
AAAGTGCCATCACTATTGAGACAGGTTCTCCTGGGGCTACATCAGAGGGTACCCTCACCTTGGACACCTCAACA
ACAACCTTTTGGTCAGGGACCCACTCAACTGCATCTCCAGGATTTTCACACTCAGAGATGACCACTCTTATGAG
TAGAACTCCTGGAGATGTGCCATGGCCGAGCCTTCCCTCTGTGGAAGAAGCCAGCTCTGTCTCTTCCTCACTGT
CTTCACCTGCCATGACCTCAACTTCTTTTTTCTCCACATTACCAGAGAGCATCTCCTCCTCTCCTCATCCTGTG
ACTGCACTTCTCACCCTTGGCCCAGTGAAGACCACAGACATGTTGCGCACAAGCTCAGAACCTGAAACCAGTTC
ACCTCCAAATTTGAGCAGCACCTCAGCTGAAATATTAGCCACGTCTGAAGTCACCAAAGATAGAGAGAAAATTC
ATCCCTCCTCAAACACACCTGTAGTCAATGTAGGGACTGTGATTTATAAACATCTATCCCCTTCCTCTGTTTTG
GCTGACTTAGTGACAACAAAACCCACATCTCCAATGGCTACCACCTCCACTCTGGGGAATACAAGTGTTTCCAC
ATCAACTCCTGCCTTCCCAGAAACTATGATGACACAGCCAACTTCCTCCCTGACTTCTGGATTAAGGGAGATCA
GTACCTCTCAAGAGACCAGCTCAGCAACAGAGAGAAGTGCTTCTCTTTCTGGAATGCCCACTGGTGCTACTACT
AAGGTCTCCAGAACAGAAGCCCTCTCCTTAGGCAGAACATCCACCCCAGGTCCTGCTCAATCCACAATATCACC
AGAAATCTCCACGGAAACCATCACTAGAATTTCTACTCCCCTCACCACGACAGGATCAGCAGAAATGACCATCA
CCCCCAAAACAGGTCATTCTGGGGCATCCTCACAAGGTACCTTTACCTTGGACACATCAAGCAGAGCCTCCTGG
CCAGGAACTCACTCAGCTGCAACTCACAGATCTCCACACTCAGGGATGACCACTCCTATGAGCAGAGGTCCTGA
GGATGTGTCATGGCCAAGCCGCCCATCAGTGGAAAAAACTAGCCCTCCATCTTCCCTGGTGTCTTTATCTGCAG
TAACCTCACCTTCGCCACTTTATTCCACACCATCTGAGAGTAGCCACTCGTCTCCTCTCCGGGTGACTTCTCTT
TTCACCCCTGTCATGATGAAGACCACAGACATGTTGGACACAAGCTTGGAACCTGTGACCACTTCACCTCCCAG
TATGAATATCACCTCAGATGAGAGTCTGGCCACTTCTAAAGCCACCATGGAGACAGAGGCAATTCAGCTTTCAG
AAAACACAGCTGTGACTCAGATGGGCACCATCAGTGCTAGACAAGAATTCTATTCCTCTTATCCAGGCCTCCCA
GAGCCATCCAAAGTGACATCTCCAGTGGTCACCTCTTCCACCATAAAAGACATTGTTTCTACAACCATACCTGC
TTCCTCTGAGATAACAAGAATTGAGATGGAGTCAACATCCACCCTGACCCCCACACCAAGGGAGACCAGCACCT
CCCAGGAGATCCACTCAGCCACAAAGCCAAGCACTGTTCCTTACAAGGCACTCACTAGTGCCACGATTGAGGAC
TCCATGACACAAGTCATGTCCTCTAGCAGAGGACCTAGCCCTGATCAGTCCACAATGTCACAAGACATATCCAC
TGAAGTGATCACCAGGCTCTCTACCTCCCCCATCAAGACAGAATCTACAGAAATGACCATTACCACCCAAACAG
GTTCTCCTGGGGCTACATCAAGGGGTACCCTTACCTTGGACACTTCAACAACTTTTATGTCAGGGACCCATTCA
ACTGCATCTCAAGGATTTTCACACTCACAGATGACCGCTCTTATGAGTAGAACTCCTGGAGAGGTGCCATGGCT
AAGCCATCCCTCTGTGGAAGAAGCCAGCTCTGCCTCTTTCTCACTGTCTTCACCTGTCATGACCTCATCTTCTC
CCGTTTCTTCCACATTACCAGACAGCATCCACTCTTCTTCGCTTCCTGTGACATCACTTCTCACCTCAGGGCTG
GTGAAGACCACAGAGCTGTTGGGCACAAGCTCAGAACCTGAAACCAGTTCACCCCCAAATTTGAGCAGCACCTC
AGCTGAAATACTGGCCACCACTGAAGTCACTACAGATACAGAGAAACTGGAGATGACCAATGTGGTAACCTCAG
GTTATACACATGAATCTCCTTCCTCTGTCCTAGCTGACTCAGTGACAACAAAGGCACATCTTCAATGGGTATC
ACCTACCCCACAGGAGATACAAATGTTCTCACATCAACCCCTGCCTTCTCTGACACCAGTAGGATTCAAACAAA
GTCAAAGCTCTCACTGACTCCTGGGTTGATGGAGACCAGCATCTCTGAAGAGACCAGCTCTGCCACAGAAAAAA
GCACTGTCCTTTCTAGTGTGCCCACTGGTGCTACTACTGAGGTCTCCAGGACAGAAGCCATCTCTTCTAGCAGA
ACATCCATCCCAGGCCCTGCTCAATCCACAATGTCATCAGACACCTCCATGGAAACCATCACTAGAATTTCTAC
CCCCCTCACAAGGAAAGAATCAACAGACATGGCCATCACCCCCAAAACAGGTCCTTCTGGGGCTACCTCGCAGG
GTACCTTTACCTTGGACTCATCAAGCACAGCCTCCTGGCCAGGAACTCACTCAGCTACAACTCAGAGATTTCCA
CGGTCAGTGGTGACAACTCCTATGAGCAGAGGTCCTGAGGATGTGTCATGGCCAAGCCCGCTGTCTGTGGAAAA
AAACAGCCCTCCATCTTCCCTGGTATCTTCATCTTCAGTAACCTCACCTTCGCCACTTTATTCCACACCATCTG
GGAGTAGCCACTCCTCTCCTGTCCCTGTCACTTCTCTTTTCACCTCTATCATGATGAAGGCCACAGACATGTTG
```

FIGURE 8

(cont.)

GATGCAAGTTTGGAACCTGAGACCACTTCAGCTCCCAATATGAATATCACCTCAGATGAGAGTCTGGCCGCTTC
TAAAGCCACCACGGAGACAGAGGCAATTCACGTTTTTGAAAATACAGCAGCGTCCCATGTGGAAACCACCAGTG
CTACAGAGGAACTCTATTCCTCTTCCCCAGGCTTCTCAGAGCCAACAAAAGTGATATCTCCAGTGGTCACCTCT
TCCTCTATAAGAGACAACATGGTTTCCACAACAATGCCTGGCTCCTCTGGCATTACAAGGATTGAGATAGAGTC
AATGTCATCTCTGACCCCTGGACTGAGGGAGACCAGAACCTCCCAGGACATCACCTCATCCACAGAGACAAGCA
CTGTCCTTTACAAGATGCCCTCTGGTGCCACTCCTGAGGTCTCCAGGACAGAAGTTATGCCCTCTAGCAGAACA
TCCATTCCTGGCCCTGCTCAGTCCACAATGTCACTAGACATCTCCGATGAAGTTGTCACCAGGCTGTCTACCTC
TCCCATCATGACAGAATCTGCAGAAATAACCATCACCACCCAAACAGGTTATTCTCTGGCTACATCCCAGGTTA
CCCTTCCCTTGGGCACCTCAATGACCTTTTTGTCAGGGACCCACTCAACTATGTCTCAAGGACTTTCACACTCA
GAGATGACCAATCTTATGAGCAGGGGTCCTGAAAGTCTGTCATGGACGAGCCCTCGCTTTGTGGAAACAACTAG
ATCTTCCTCTTCTCTGACATCATTACCTCTCACGACCTCACTTTCTCCTGTGTCCTCCACATTACTAGACAGTA
GCCCCTCCTCTCCTCTTCCTGTGACTTCACTTATCCTCCCAGGCCTGGTGAAGACTACAGAAGTGTTGGATACA
AGCTCAGAGCCTAAAACCAGTTCATCTCCAAATTTGAGCAGCACCTCAGTTGAAATACCGGCCACCTCTGAAAT
CATGACAGATACAGAGAAAATTCATCCTTCCTCAAACACAGCGGTGGCCAAAGTGAGGACCTCCAGTTCTGTTC
ATGAATCTCATTCCTCTGTCCTAGCTGACTCAGAAACAACCATAACCATACCTTCAATGGGTATCACCTCCGCT
GTGGAGGATACCACTGTTTTCACATCAAATCCTGCCTTCTCTGAGACTAGGAGGATTCCGACAGAGCCAACATT
CTCATTGACTCCTGGATTCAGGGAGACTAGCACCTCTGAAGAGACCACCTCAATCACAGAAACAAGTGCAGTCC
TTTTTGGAGTGCCCACTAGTGCTACTACTGAAGTCTCCATGACAGAAATAATGTCCTCTAATAGAACACACATC
CCTGACTCTGATCAGTCCACGATGTCTCCAGACATCATCACTGAAGTGATCACCAGGCTCTCTTCCTCATCCAT
GATGTCAGAATCAACACAAATGACCATCACCACCCAAAAAAGTTCTCCTGGGGCTACAGCACAGAGTACTCTTA
CCTTGGCCACAACAACAGCCCCCTTGGCAAGGACCCACTCAACTGTTCCTCCTAGATTTTTACACTCAGAGATG
ACAACTCTTATGAGTAGGAGTCCTGAAAATCCATCATGGAAGAGCTCTCCCTTTGTGGAAAAAACTAGCTCTTC
ATCTTCTCTGTTGTCCTTACCTGTCACGACCTCACCTTCTGTTTCTTCCACATTACCGCAGAGTATCCCTTCCT
CCTCTTTTTCTGTGACTTCACTCCTCACCCCAGGCATGGTGAAGACTACAGACACAAGCACAGAACCTGGAACC
AGTTTATCTCCAAATCTGAGTGGCACCTCAGTTGAAATACTGGCTGCCTCTGAAGTCACCACAGATACAGAGAA
AATTCATCCTTCTTCAAGCATGGCAGTGACCAATGTGGGAACCACCAGTTCTGGACATGAACTATATTCCTCTG
TTTCAATCCACTCGGAGCCATCCAAGGCTACATACCCAGTGGGTACTCCCTCTTCCATGGCTGAAACCTCTATT
TCCACATCAATGCCTGCTAATTTTGAGACCACAGGATTTGAGGCTGAGCCATTTTCTCATTTGACTTCTGGACT
TAGGAAGACCAACATGTCCCTGGACACCAGCTCAGTCACACCAACAAATACACCTTCTTCTCCTGGGTCCACTC
ACCTTTTACAGAGTTCCAAGACTGATTTCACCTCTTCTGCAAAAACATCATCCCCAGACTGGCCTCCAGCCTCA
CAGTATACTGAAATTCCAGTGGACATAATCACCCCCTTTAATGCTTCTCCATCTATTACGGAGTCCACTGGGAT
AACCTCCTTCCCAGAATCCAGGTTTACTATGTCTGTAACAGAAAGTACTCATCATCTGAGTACAGATTTGCTGC
CTTCAGCTGAGACTATTTCCACTGGCACAGTGATGCCTTCTCTATCAGAGGCCATGACTTCATTTGCCACCACT
GGAGTTCCACGAGCCATCTCAGGTTCAGGTAGTCCATTCTCTAGGACAGAGTCAGGCCCTGGGGATGCTACTCT
GTCCACCATTGCAGAGAGCCTGCCTTCATCCACTCCTGTGCCATTCTCCTCTTCAACCTTCACTACCACTGATT
CTTCAACCATCCCAGCCCTCCATGAGATAACTTCCTCTTCAGCTACCCCATATAGAGTGGACACCAGTCTTGGG
ACAGAGAGCAGCACTACTGAAGGACGCTTGGTTATGGTCAGTACTTTGGACACTTCAAGCCAACCAGGCAGGAC
ATCTTCATCACCCATTTTGGATACCAGAATGACAGAGAGCGTTGAGCTGGGAACAGTGACAAGTGCTTATCAAG
TTCCTTCACTCTCAACACGGTTGACAAGAGATGGCATTATGGAACACATCACAAAAATACCCAATGAAGCAGCA
CACAGAGGTACCATAAGACCAGTCAAAGGCCCTCAGACATCCACTTCGCCTGCCAGTCCTAAAGGACTACACAC
AGGAGGGACAAAAAGAATGGAGACCACCACCACAGCTCTGAAGACCACCACCACAGCTCTGAAGACCACTTCCA
GAGCCACCTTGACCACCAGTGTCTATACTCCCACTTTGGGAACACTGACTCCCCTCAATGCATCAATGCAAATG
GCCAGCACAATCCCCACAGAAATGATGATCACAACCCCATATGTTTTCCCTGATGTTCCAGAAACGACATCCTC

FIGURE 8

(cont.)

```
ATTGGCTACCAGCCTGGGAGCAGAAACCAGCACAGCTCTTCCCAGGACAACCCCATCTGTTTTCAATAGAGAAT
CAGAGACCACAGCCTCACTGGTCTCTCGTTCTGGGGCAGAGAGAAGTCCGGTTATTCAAACTCTAGATGTTTCT
TCTAGTGAGCCAGATACAACAGCTTCATGGGTTATCCATCCTGCAGAGACCATCCCAACTGTTTCCAAGACAAC
CCCCAATTTTTTCCACAGTGAATTAGACACTGTATCTTCCACAGCCACCAGTCATGGGGCAGACGTCAGCTCAG
CCATTCCAACAAATATCTCACCTAGTGAACTAGATGCACTGACCCCACTGGTCACTATTTCGGGGACAGATACT
AGTACAACATTCCCAACACTGACTAAGTCCCCACATGAAACAGAGACAAGAACCACATGGCTCACTCATCCTGC
AGAGACCAGCTCAACTATTCCCAGAACAATCCCCAATTTTTCTCATCATGAATCAGATGCCACACCTTCAATAG
CCACCAGTCCTGGGGCAGAAACCAGTTCAGCTATTCCAATTATGACTGTCTCACCTGGTGCAGAAGATCTGGTG
ACCTCACAGGTCACTAGTTCTGGCACAGACAGAAATATGACTATTCCAACTTTGACTCTTTCTCCTGGTGAACC
AAAGACCATAGCCTCATTAGTCACCCATCCTGAAGCACAGACAAGTTCGGCCATTCCAACTTCAACTATCTCGC
CTGCTGTATCACGGTTGGTGACCTCAATGGTCACCAGTTTGGCGGCAAAGACAAGTACAACTAATCGAGCTCTG
ACAAACTCCCCTGGTGAACCAGCTACAACAGTTTCATTGGTCACGCATTCTGCACAGACCAGCCCAACAGTTCC
CTGGACAACTTCCATTTTTTTCCATAGTAAATCAGACACCACACCTTCAATGACCACCAGTCATGGGGCAGAAT
CCAGTTCAGCTGTTCCAACTCCAACTGTTTCAACTGAGGTACCAGGAGTAGTGACCCCTTTGGTCACCAGTTCT
AGGGCAGTGATCAGTACAACTATTCCAATTCTGACTCTTTCTCCTGGTGAACCAGAGACCACACCTTCAATGGC
CACCAGTCATGGGGAAGAAGCCAGTTCTGCTATTCCAACTCCAACTGTTTCACCTGGGGTACCAGGAGTGGTGA
CCTCTCTGGTCACTAGTTCTAGGGCAGTGACTAGTACAACTATTCCAATTCTGACTTTTTCTCTTGGTGAACCA
GAGACCACACCTTCAATGGCCACCAGTCATGGGACAGAAGCTGGCTCAGCTGTTCCAACTGTTTTACCTGAGGT
ACCAGGAATGGTGACCTCTCTGGTTGCTAGTTCTAGGGCAGTAACCAGTACAACTCTTCCAACTCTGACTCTTT
CTCCTGGTGAACCAGAGACCACACCTTCAATGGCCACCAGTCATGGGGCAGAAGCCAGCTCAACTGTTCCAACT
GTTTCACCTGAGGTACCAGGAGTGGTGACCTCTCTGGTCACTAGTTCTAGTGGAGTAAACAGTACAAGTATTCC
AACTCTGATTCTTTCTCCTGGTGAACTAGAAACCACACCTTCAATGGCCACCAGTCATGGGGCAGAAGCCAGCT
CAGCTGTTCCAACTCCAACTGTTTCACCTGGGGTATCAGGAGTGGTGACCCCTCTGGTCACTAGTTCCAGGGCA
GTGACCAGTACAACTATTCCAATTCTAACTCTTTCTTCTAGTGAGCCAGAGACCACACCTTCAATGGCCACCAG
TCATGGGGTAGAAGCCAGCTCAGCTGTTCTAACTGTTTCACCTGAGGTACCAGGAATGGTGACCTTTCTGGTCA
CTAGTTCTAGAGCAGTAACCAGTACAACTATTCCAACTCTGACTATTTCTTCTGATGAACCAGAGACCACAACT
TCATTGGTCACCCATTCTGAGGCAAAGATGATTTCAGCCATTCCAACTTTAGGTGTCTCCCCTACTGTACAAGG
GCTGGTGACTTCACTGGTCACTAGTTCTGGGTCAGAGACCAGTGCGTTTTCAAATCTAACTGTTGCCTCAAGTC
AACCAGAGACCATAGACTCATGGGTCGCTCATCCTGGGACAGAAGCAAGTTCTGTTGTTCCAACTTTGACTGTC
TCCACTGGTGAGCCGTTTACAAATATCTCATTGGTCACCCATCCTGCAGAGAGTAGCTCAACTCTTCCCAGGAC
AACCTCAAGGTTTTCCCACAGTGAATTAGACACTATGCCTTCTACAGTCACCAGTCCTGAGGCAGAATCCAGCT
CAGCCATTTCAACAACTATTTCACCTGGTATACCAGGTGTGCTGACATCACTGGTCACTAGCTCTGGGAGAGAC
ATCAGTGCAACTTTTCCAACAGTGCCTGAGTCCCCACATGAATCAGAGGCAACAGCCTCATGGGTTACTCATCC
TGCAGTCACCAGCACAACAGTTCCCAGGACAACCCCTAATTATTCTCATAGTGAACCAGACACCACACCATCAA
TAGCCACCAGTCCTGGGGCAGAAGCCACTTCAGATTTTCCAACAATAACTGTCTCACCTGATGTACCAGATATG
GTAACCTCACAGGTCACTAGTTCTGGGACAGACACCAGTATAACTATTCCAACTCTGACTCTTTCTTCTGGTGA
GCCAGAGACCACAACCTCATTTATCACCTATTCTGAGACACATACAAGTTCAGCCATTCCAACTCTCCCTGTCT
CCCCTGATGCATCAAAGATGCTGACCTCACTGGTCATCAGTTCTGGGACAGACAGCACTACAACTTTCCCAACA
CTGACGGAGACCCCATATGAACCAGAGACAACAGCCATACAGCTCATTCATCCTGCAGAGACCAACACAATGGT
TCCCAGGACAACTCCCAAGTTTTCCCATAGTAAGTCAGACACCACACTCCCAGTAGCCATCACCAGTCCTGGGC
CAGAAGCCAGTTCAGCTGTTTCAACGACAACTATCTCACCTGATATGTCAGATCTGGTGACCTCACTGGTCCCT
AGTTCTGGGACAGACACCAGTACAACCTTCCCAACATTGAGTGAGACCCCATATGAACCAGAGACTACAGCCAC
GTGGCTCACTCATCCTGCAGAAACCAGCACAACGGTTTCTGGGACAATTCCCAACTTTTCCCATAGGGGATCAG
ACACTGCACCCTCAATGGTCACCAGTCCTGGAGTAGACACGAGGTCAGGTGTTCCAACTACAACCATCCCACCC
```

FIGURE 8

(cont.)

AGTATACCAGGGGTAGTGACCTCACAGGTCACTAGTTCTGCAACAGACACTAGTACAGCTATTCCAACTTTGAC
TCCTTCTCCTGGTGAACCAGAGACCACAGCCTCATCAGCTACCCATCCTGGGACACAGACTGGCTTCACTGTTC
CAATTCGGACTGTTCCCTCTAGTGAGCCAGATACAATGGCTTCCTGGGTCACTCATCCTCCACAGACCAGCACA
CCTGTTTCCAGAACAACCTCCAGTTTTTCCCATAGTAGTCCAGATGCCACACCTGTAATGGCCACCAGTCCTAG
GACAGAAGCCAGTTCAGCTGTACTGACAACAATCTCACCTGGTGCACCAGAGATGGTGACTTCACAGATCACTA
GTTCTGGGGCAGCAACCAGTACAACTGTTCCAACTTTGACTCATTCTCCTGGTATGCCAGAGACCACAGCCTTA
TTGAGCACCCATCCCAGAACAGAGACAAGTAAAACATTTCCTGCTTCAACTGTGTTTCCTCAAGTATCAGAGAC
CACAGCCTCACTCACCATTAGACCTGGTGCAGAGACTAGCACAGCTCTCCCAACTCAGACAACATCCTCTCTCT
TCACCCTACTTGTAACTGGAACCAGCAGAGTTGATCTAAGTCCAACTGCTTCACCTGGTGTTTCTGCAAAAACA
GCCCCACTTTCCACCCATCCAGGGACAGAAACCAGCACAATGATTCCAACTTCAACTCTTTCCCTTGGTTTACT
AGAGACTACAGGCTTACTGGCCACCAGCTCTTCAGCAGAGACCAGCACGAGTACTCTAACTCTGACTGTTTCCC
CTGCTGTCTCTGGGCTTTCCAGTGCCTCTATAACAACTGATAAGCCCCAAACTGTGACCTCCTGGAACACAGAA
ACCTCACCATCTGTAACTTCAGTTGGACCCCAGAATTTTCCAGGACTGTCACAGGCACCACTATGACCTTGAT
ACCATCAGAGATGCCAACACCACCTAAAACCAGTCATGGAGAAGGAGTGAGTCCAACCACTATCTTGAGAACTA
CAATGGTTGAAGCCACTAATTTAGCTACCACAGGTTCCAGTCCCACTGTGGCCAAGACAACAACCACCTTCAAT
ACACTGGCTGGAAGCCTCTTTACTCCTCTGACCACACCTGGGATGTCCACCTTGGCCTCTGAGAGTGTGACCTC
AAGAACAAGTTATAACCATCGGTCCTGGATCTCCACCACCAGCAGTTATAACCGTCGGTACTGGACCCCTGCCA
CCAGCACTCCAGTGACTTCTACATTCTCCCCAGGGATTTCCACATCCTCCATCCCCAGCTCCACAGCAGCCACA
GTCCCATTCATGGTGCCATTCACCCTCAACTTCACCATCACCAACCTGCAGTACGAGGAGGACATGCGGCACCC
TGGTTCAAGGAAGTTCAACGCCACAGAGAGAGAACTGCAGGGTCTGCTCAAACCCTTGTTCAGGAATAGCAGTC
TGGAATACCTCTATTCAGGCTGCAGACTAGCCTCACTCAGGCCAGAGAAGGATAGCTCAGCCACGGCAGTGGAT
GCCATCTGCACACATCGCCCTGACCCTGAAGACCTCGGACTGGACAGAGAGCGACTGTACTGGGAGCTGAGCAA
TCTGACAAATGGCATCCAGGAGCTGGGCCCTTACACCCTGGACCGGAACAGTCTCTATGTCAATGGTTTCACCC
ATCGAAGCTCTATGCCCACCACCAGCACTCCTGGGACCTCCACAGTGGATGTGGGAACCTCAGGGACTCCATCC
TCCAGCCCCAGCCCCACGACTGCTGGCCCTCTCCTGATGCCGTTCACCCTCAACTTCACCATCACCAACCTGCA
GTACGAGGAGGACATGCGTCGCACTGGCTCCAGGAAGTTCAACACCATGGAGAGTGTCCTGCAGGGTCTGCTCA
AGCCATTGTTCAAGAACACCAGTGTTGGCCCTTTGTACTCTGGCTGCAGATTGACCTTGCTCAGGCCCGAGAAA
GATGGGGCAGCCACTGGAGTGGATGCCATCTGCACCCACCGCCTTGACCCCAAAAGCCCTGGACTCAACAGGGA
GCAGCTGTACTGGGAGCTAAGCAAACTGACCAATGACATTGAAGAGCTGGGCCCCTACACCCTGGACAGGAACA
GTCTCTATGTCAATGGTTTCACCCATCAGAGCTCTGTGTCCACCACCAGCACTCCTGGGACCTCCACAGTGGAT
CTCAGAACCTCAGGGACTCCATCCTCCCTCTCCAGCCCCACAATTATGGCTGCTGGCCCTCTCCTGGTACCATT
CACCCTCAACTTCACCATCACCAACCTGCAGTATGGGGAGGACATGGGTCACCCTGGCTCCAGGAAGTTCAACA
CCACAGAGAGGGTCCTGCAGGGTCTGCTTGGTCCCATATTCAAGAACACCAGTGTTGGCCCTCTGTACTCTGGC
TGCAGACTGACCTCTCTCAGGTCCGAGAAGGATGGAGCAGCCACTGGAGTGGATGCCATCTGCATCCATCATCT
TGACCCCAAAAGCCCTGGACTCAACAGAGAGCGGCTGTACTGGGAGCTGAGCCAACTGACCAATGGCATCAAAG
AGCTGGGCCCCTACACCCTGGACAGGAACAGTCTCTATGTCAATGGTTTCACCCATCGGACCTCTGTGCCCACC
ACCAGCACTCCTGGGACCTCCACAGTGGACCTTGGAACCTCAGGGACTCCATTCTCCCTCCCAAGCCCCGCAAC
TGCTGGCCCTCTCCTGGTGCTGTTCACCCTCAACTTCACCATCACCAACCTGAAGTATGAGGAGGACATGCATC
GCCCTGGCTCCAGGAAGTTCAACACCACTGAGAGGGTCCTGCAGACCCTGGTTGGTCCTATGTTCAAGAACACC
AGTGTTGGCCTTCTGTACTCTGGCTGCAGACTGACCTTGCTCAGGTCCGAGAAGGATGGAGCAGCCACTGGAGT
GGATGCCATCTGCACCCACCGTCTTGACCCCAAAAGCCCTGGAGTGGACAGGGAGCAGCTATACTGGGAGCTGA
GCCAACTGACCAATGGCATCAAAGAGCTGGGCCCCTACACCCTGGACAGGAACAGTCTCTATGTCAATGGTTTC
ACCCATTGGATCCCTGTGCCCACCAGCAGCACCCCTGGGACCTCCACAGTGGACCTTGGGTCAGGGACTCCATC

FIGURE 8

(cont.)

```
CTCCCTCCCCAGCCCCACAAGTGCTGCTGGCCCTCTCCTGGTGCCATTCACCCTCAACTTCACCATCACCAACC
TGCAGTACGAGGAGGACATGCATCACCCAGGCTCCAGGAAGTTCAACACCACGGAGCGGGTCCTGCAGGGTCTG
CTTGGTCCTATGTTCAAGAACACCAGTGTTGGCCTTCTGTACTCTGGCTGCAGACTGACCTTGCTCAGGTCCGA
GAAGGATGGAGCAGCCACTGGAGTGGATGCCATCTGCACCCACCGTCTTGACCCCAAAAGCCCTGGAGTGGACA
GGGAGCAGCTATACTGGGAGCTGAGCCAGCTGACCAATGGCATCAAAGAGCTGGGCCCCTACACCCTGGACAGG
AACAGTCTCTATGTCAATGGTTTCACCCATTGGATCCCTGTGCCCACCAGCAGCACTCCTGGGACCTCCACAGT
GGACCTTGGGTCAGGGACTCCATCCTCCCTCCCCAGCCCCACAACTGCTGGCCCTCTCCTGGTGCCGTTCACCC
TCAACTTCACCATCACCAACCTGAAGTACGAGGAGGACATGCATTGCCCTGGCTCCAGGAAGTTCAACACCACA
GAGAGAGTCCTGCAGAGTCTGCTTGGTCCCATGTTCAAGAACACCAGTGTTGGCCCTCTGTACTCTGGCTGCAG
ACTGACCTTGCTCAGGTCCGAGAAGGATGGAGCAGCCACTGGAGTGGATGCCATCTGCACCCACCGTCTTGACC
CCAAAAGCCCTGGAGTGGACAGGGAGCAGCTATACTGGGAGCTGAGCCAGCTGACCAATGGCATCAAAGAGCTG
GGTCCCTACACCCTGGACAGAAACAGTCTCTATGTCAATGGTTTCACCCATCAGACCTCTGCGCCCAACACCAG
CACTCCTGGGACCTCCACAGTGGACCTTGGGACCTCAGGGACTCCATCCTCCCTCCCCAGCCCTACATCTGCTG
GCCCTCTCCTGGTGCCATTCACCCTCAACTTCACCATCACCAACCTGCAGTACGAGGAGGACATGCATCACCCA
GGCTCCAGGAAGTTCAACACCACGGAGCGGGTCCTGCAGGGTCTGCTTGGTCCCATGTTCAAGAACACCAGTGT
CGGCCTTCTGTACTCTGGCTGCAGACTGACCTTGCTCAGGCCTGAGAAGAATGGGGCAGCCACTGGAATGGATG
CCATCTGCAGCCACCGTCTTGACCCCAAAAGCCCTGGACTCAACAGAGAGCAGCTGTACTGGGAGCTGAGCCAG
CTGACCCATGGCATCAAAGAGCTGGGCCCCTACACCCTGGACAGGAACAGTCTCTATGTCAATGGTTTCACCCA
TCGGAGCTCTGTGGCCCCCACCAGCACTCCTGGGACCTCCACAGTGGACCTTGGGACCTCAGGGACTCCATCCT
CCCTCCCCAGCCCCACAACAGCTGTTCCTCTCCTGGTGCCGTTCACCCTCAACTTTACCATCACCAATCTGCAG
TATGGGGAGGACATGCGTCACCCTGGCTCCAGGAAGTTCAACACCACAGAGAGGGTCCTGCAGGGTCTGCTTGG
TCCCTTGTTCAAGAACTCCAGTGTCGGCCCTCTGTACTCTGGCTGCAGACTGATCTCTCTCAGGTCTGAGAAGG
ATGGGGCAGCCACTGGAGTGGATGCCATCTGCACCCACCACCTTAACCCTCAAAGCCCTGGACTGGACAGGGAG
CAGCTGTACTGGCAGCTGAGCCAGATGACCAATGGCATCAAAGAGCTGGGCCCCTACACCCTGGACCGGAACAG
TCTCTACGTCAATGGTTTCACCCATCGGAGCTCTGGGCTCACCACCAGCACTCCTTGGACTTCCACAGTTGACC
TTGGAACCTCAGGGACTCCATCCCCCGTCCCCAGCCCCACAACTGCTGGCCCTCTCCTGGTGCCATTCACCCTA
AACTTCACCATCACCAACCTGCAGTATGAGGAGGACATGCATCGCCCTGGATCTAGGAAGTTCAACGCCACAGA
GAGGGTCCTGCAGGGTCTGCTTAGTCCCATATTCAAGAACTCCAGTGTTGGCCCTCTGTACTCTGGCTGCAGAC
TGACCTCTCTCAGGCCCGAGAAGGATGGGGCAGCAACTGGAATGGATGCTGTCTGCCTCTACCACCCTAATCCC
AAAAGACCTGGGCTGGACAGAGAGCAGCTGTACTGGGAGCTAAGCCAGCTGACCCACAACATCACTGAGCTGGG
CCCCTACAGCCTGGACAGGGACAGTCTCTATGTCAATGGTTTCACCCATCAGAACTCTGTGCCCACCACCAGTA
CTCCTGGGACCTCCACAGTGTACTGGGCAACCACTGGGACTCCATCCTCCTTCCCGGCCACACAGAGCCTGGC
CCTCTCCTGATACCATTCACTTTCAACTTTACCATCACCAACCTGCATTATGAGGAAAACATGCAACACCCTGG
TTCCAGGAAGTTCAACACCACGGAGAGGGTTCTGCAGGGTCTGCTCAAGCCCTTGTTCAAGAACACCAGTGTTG
GCCCTCTGTACTCTGGCTGCAGACTGACCTTGCTCAGACCTGAGAAGCAGGAGGCAGCCACTGGAGTGGACACC
ATCTGTACCCACCGCGTTGATCCCATCGGACCTGGACTGGACAGAGAGCGGCTATACTGGGAGCTGAGCCAGCT
GACCAACAGCATCACAGAGCTGGGACCCTACACCCTGGATAGGGACAGTCTCTATGTCAATGGCTTCAACCCTT
GGAGCTCTGTGCCAACCACCAGCACTCCTGGGACCTCCACAGTGCACCTGGCAACCTCTGGGACTCCATCCTCC
CTGCCTGGCCACACAGCCCTGTCCCTCTCTTGATACCATTCACCCTCAACTTTACCATCACCAACCTGCATTA
TGAAGAAAACATGCAACACCCTGGTTCCAGGAAGTTCAACACCACGGAGAGGGTTCTGCAGGGTCTGCTCAAGC
CCTTGTTCAAGAGCACCAGCGTTGGCCCTCTGTACTCTGGCTGCAGACTGACCTTGCTCAGACCTGAGAAACAT
GGGGCAGCCACTGGAGTGGACGCCATCTGCACCCTCCGCCTTGATCCCACTGGTCCTGGACTGGACAGAGAGCG
GCTATACTGGGAGCTGAGCCAGCTGACCAACAGCGTTACAGAGCTGGGCCCCTACACCCTGGACAGGGACAGTC
TCTATGTCAATGGCTTCACCCATCGGAGCTCTGTGCCAACCACCAGTATTCCTGGGACCTCTGCAGTGCACCTG
```

FIGURE 8

(cont.)

```
GAAACCTCTGGGACTCCAGCCTCCCTCCCTGGCCACACAGCCCCTGGCCCTCTCCTGGTGCCATTCACCCTCAA
CTTCACTATCACCAACCTGCAGTATGAGGAGGACATGCGTCACCCTGGTTCCAGGAAGTTCAACACCACGGAGA
GAGTCCTGCAGGGTCTGCTCAAGCCCTTGTTCAAGAGCACCAGTGTTGGCCCTCTGTACTCTGGCTGCAGACTG
ACCTTGCTCAGGCCTGAAAAACGTGGGGCAGCCACCGGCGTGGACACCATCTGCACTCACCGCCTTGACCCTCT
AAACCCTGGACTGGACAGAGAGCAGCTATACTGGGAGCTGAGCAAACTGACCCGTGGCATCATCGAGCTGGCC
CCTACCTCCTGGACAGAGGCAGTCTCTATGTCAATGGTTTCACCCATCGGAACTTTGTGCCCATCACCAGCACT
CCTGGGACCTCCACAGTACACCTAGGAACCTCTGAAACTCCATCCTCCCTACCTAGACCCATAGTGCCTGGCCC
TCTCCTGGTGCCATTCACCCTCAACTTCACCATCACCAACTTGCAGTATGAGGAGGCCATGCGACACCCTGGCT
CCAGGAAGTTCAATACCACGGAGAGGGTCCTACAGGGTCTGCTCAGGCCCTTGTTCAAGAATACCAGTATCGGC
CCTCTGTACTCCAGCTGCAGACTGACCTTGCTCAGGCCAGAGAAGGACAAGGCAGCCACCAGAGTGGATGCCAT
CTGTACCCACCACCCTGACCCTCAAAGCCCTGGACTGAACAGAGAGCAGCTGTACTGGGAGCTGAGCCAGCTGA
CCCACGGCATCACTGAGCTGGCCCCTACACCCTGGACAGGGACAGTCTCTATGTCGATGGTTTCACTCATTGG
AGCCCCATACCAACCACCAGCACTCCTGGGACCTCCATAGTGAACCTGGGAACCTCTGGGATCCCACCTTCCCT
CCCTGAAACTACAGCCACCGGCCCTCTCCTGGTGCCATTCACACTCAACTTCACCATCACTAACCTACAGTATG
AGGAGAACATGGGTCACCCTGGCTCCAGGAAGTTCAACATCACGGAGAGTGTTCTGCAGGGTCTGCTCAAGCCC
TTGTTCAAGAGCACCAGTGTTGGCCCTCTGTATTCTGGCTGCAGACTGACCTTGCTCAGGCCTGAGAAGGACGG
AGTAGCCACCAGAGTGGACGCCATCTGCACCCACCGCCCTGACCCCAAAATCCCTGGGCTAGACAGACAGCAGC
TATACTGGGAGCTGAGCCAGCTGACCCACAGCATCACTGAGCTGGGACCCTACACCCTGGATAGGGACAGTCTC
TATGTCAATGGTTTCACCCAGCGGAGCTCTGTGCCCACCACCAGCAGTGAGTATTCTACTGATGTTCCCATGGC
CCCAATCTTACAACAAACTTAGCAGGAGCTGACCCCTATTCATAAGCCCTTATGTCCTTTCCATAAGGGAAGGA
ACATAGAGGACACAAATTATTCCCCTTCCCCACTGCCCCAGCTAATCAGAGTCCCAGCTGAAGCCCCACAGGCA
AAAATCCCCATGAATAGTCCCTCCTGCTGGCATTACNTTCCATGAGAGCACNTTGCTCCTTTCACTGTTGAGGG
CTTCTCCTCAGCTCCTGGGACTTTCACAGTACAGCCGGAAACCTCTGAGACTCCATCATCCCTCCCTGGCCCCA
CAGGTAAATACCAGTCAATGGTATTTGGAGCATGGTTGATGAGTGTAAACATCTCTGTTTATACTCTGTTAGAG
CATGGTTGATGAGTGTAAACATCTCTGTCATTATTCACTCAACTAAAGATGGAAATTCATAGTAAATGTAGTAA
CCATAGGTCAACCAACCCAGTTCATTGAGCACTGCCTCTGTATCAGGACCTGGATATACATCAGGGAACAAAAA
AAAAAAAAAAA
```

FIGURE 9

```
MGISREPGTISSTSNLLSTSHERLITLEJVDTEAMQSTHTAVINVRTSISGHESQSSVLSDSETPKATSPMGITYTMGETSVSISTSDFFETSRIQIEPISSLTSGLRETSSSERISSAEGSTVLSEVPSGATTEVSRTEVISSRGTSMSGPDQ    156
FTISPDISTEAIITRLSTSPIMTESAESAITIETGSPGATSEGTILDTSTTTFWSGITHSTASPGFSHSEMTTLMSRTPGDVPWPSLPSVEEASSVSSSLLSPAMTSTSFFSTLPESISSSPHPVTALLTLGPVKTIDMLRTSSEPETSSPPNLSST    312
SABILATSEVTKGREKIHPSSNTPVVNVGTIVIYKHLSPSSVLADLVTTKPTSPMATTSTLGNTSVSTSTPAFPETMMTQPTSSLTSGLREITSTSQETSSATENRSAASLSGMPTGATTKVSRTEALSLGRTSTPGPAQSTISPEISTETITRISTPLT    468
TTGSAEMTITPKTGHSGASSQGTIFTLDTSSRASWPGTHSAATHIRSPHSGWTTEMSRGPEDVSWPSRPSVEKTSPPSSLVSISAVTSPSPLYSTPSBESSHSSPLRVTSLFTPVWMKTIDMLDTSLEPVTTSPPSMNIITSDESLATSKATMETEAIQL    624
SENTAVTQMGTISARQEFYSSYPGLPEPSKVTSPVTTSSTIKDIVSTTIPASSEITRIEWESTSTLTPTPRETSTSQEIHSATKPSTVPYKALTSATIEDSMTQVMSSSRGPSPDQSTMSQDISTEVITRLSTSPIKTESTEMTITYQTGSPGATS    780
RGTILDTSTITFMSGTHSTASQGFSHSQMTALMSRTPGEVPWLSHPSVEASSASFSLSPVMTSSSPVSSTLPDSIHSSLLVTSLLTSGLVKTELLGISSEPETSSPPNLSSTSAEILATTEVITDEKLEMTNVVTSGYTHESPSSVLADSV    936
TTKATSSMGITYPTGDTNVLTSTPAFSDTSRIQTKSKLSLTPGLMETSISEETSSAATEKSTVLSSVPTGATTEVSRTEAISSSRTSIPGPAQSTMSSDTSMETITRISTPLTRKESTDMAITPKTGPSGATSQGTFTLDSSTASWPGTHSATTQR    1092
FPRSVVTTPMSRGPEDVSWPSLVERNSPPSSLVSSSVTSPGSSHSSPVPVTSLFTSIMMKATDMLDASLEPETTSAPNMNITSDESLAASKATTETEAIHVFENTAASHVETTSATEELYSSPGFSEPTKVISPVVTSSSIRDN    1248
MVSTIMPQSSGITRIEIESMSSLITPGLRETRISQDITSTETSTVLYKMPSGATPEVSRTEVMPSSRTSIPGPAQSTMSLDISDEVVTRLSTSPIMTESAEITITTVQTGYSLATSQVTLPLGTSMTFLSGTHSTMSQGLGHSEMINLMSRGPESLS    1404
WTSPRFVETTRSSSLTSLPLTTSLSPVSSTLLDSSPSSPLPVTSLILPGLVKTTEVLDTSSEPKTSSSPNLSSTSVEIPATSEIMDTEKIHPSSNTAVAKVRTSSSVHESHSSVLADSEITTIPSMITSAVEDTTVFTSNPAFSETRRIPTE    1560
PTFSLIPGFRETSTSEETTSIIETSAVLRGVPTSATTEVSMTELMSSNRTHIPDSDQSTMSPDIITEVIITRLSSSSMMSESTQMTITITQKSSPGATAQSTLTLATTIAPLARTHSTVPPRTIHSEMTTLMSRSPENFSWKSSPFVEKTSSSSLLS    1716
LPVTTSPSVSSTLPQSIPSSFSVTSLLTPGWKITITSTEPGTSLSPNLSGTSVEILAASEVITDTEKIHPSSMAVINVGTTSSGHELYSSVSIHSEPSKATYPVGTPSSMAFTSISTSMPANFETTGFEAEPFSHLTSGLRKTNMSLDTSSVT    1872
PNTPSSPGSTHLLQSSKTDFTSSAKTSSSPDWPPASQYTEIPVDIITPFNASPSIITESTGIITSPPESRFTMSVTESTTHLSTDLLPSAETISTGTVMPSLSEAMTSFATTGVPRAISGSGSPFSRTESGRGDATLSTIAESLPSSTPVPFSSSTPT    2028
TTDSSTIPALHEITSSATPYRVDTSLGTESSITEGRLMVVSTILDTSSQPGRTSSSPILDTRMTESVELGTVTISAYQVPSLSTRLITRDGLMEHITKIPNEAAHRGTIRPVKPVQTSTSPASPKGLHTGGTKRMETITTIALKTTTTALKTTSRATLIT    2184
TSVYTPTLGTLTPLNASMGMASTIPTEMMITTPYVFPDVPETTSSLATSLGAETSTALPRITPSVNRESETASLVSRSGAERSPVIQTLDVSSEPDTTASWVIHPAETIPTVSKTTPNFFHSELDTVSSTATSGADVSSAIPTNISPSELDA    2340
LTPLVTISGTDTSTTFPTLTKSPHETETRTTWLTHPAETSSTIPRTIPNFSHHESDATPSIATSPGAETSSAIPIMTVSPGAEDLVTSGVTSSGTDRNMTIPTLTLSPGEPKTIASLVTHPEAQTSSAIPTSTISPAVSRLVTSMVTSLAAKTSTT    2496
NRALTNSPGEPATTVSLVTHSAQTSPTVPWTTSIFFHSKDTTPSMTTSHGAESSSAVPTTVSTEVPGVTPLVTSSGVVTPLVTSSGVVNSTSIPILILSPGELETTPSMATSHGAEASSAIPTTVSPGVPGVVTSLVTSSRAVTSTTIPILLFSLGEPETTP    2652
SMATSHGTEAGSAVPTVLPEVPGWVTSLVASSAVLTVSPEVPGWTPLVTSSRAVTSTTLPTLTLTSSDEPETTSLVTHSGAESSVPTTVSTEVPGVTPLVTSSRAVTSTTIPILTLSPGEPETTPSMATSHGAEASSAIPTTVSPGVVTSLVTSSRAVTSTTIPILTLS    2808
SSEPETTPSMATSHGVEASSAVLTVSPEVPGMTLVTSPEARSSSAITSTIISPGIPGVLTSLVTSSGRDISATFPTVPESPHESEATASWVTHPAVTSTTVPRITPNYSHSEPDTTPSIATSPGAEATSDFPTITVSPDVPDMVTSQVTSSGIDTSITIPILTLSSGEPET    2964
TLPRTTSRFSHSELDTWESVTSPEARSSSAITSTTISPGIPGVLTSTITFPTLIETPYEPETTAIQLIHPAETNTMVPRITPKFSHSKSDTTLPVAITSPGPEASSAVSTTTISPDMSDLVTSLVPSSGITVISTTIFPTLSETPYEPETTATWLTHPAETSTT    3120
TTSFITYSETHTSSAIPTLPVSPDASKMLTSLVISSGTDSTITFPTLIETPYEPETTAIQLIHPAETNTMVPRITPKFSHSKSDTTLPVAITSPGPEASSAVSTTTISPDMSDLVTSLVPSSGITVISTTIFPTLSETPYEPETTATWLTHPAETSTT    3276
VSGTIPNFSHRGSDTAPSMVTSPGVDTRSGVPTTTIPPSIPGVVTSQVTPTTTIPPSIPGVVTSQVTSSAUTTSTAIPTLTPSPGEPETTASSAATHPGTIQTQGFTVPIRTVPSSEPDTMASWVTHPPQTSTPVSRTTSFSHSSPDATPVMATSPRTEASSAVLTTISPGAPEMV    3432
TSQITSSGAATSTTVPTLTHSPQMPETTALLSTHPRTEISKTFPASTVFPQVSETTASLITIRPGAETSTALPIVTSSLGLLETTGLLATSSSAEFTSTSTLILTLTVSPAV    3588
SGLSSASITITDKQTVTSWNTETSPSVTSVGPPEFSRIVGTTMTLLIPSEMPTPPKISHGEGVSPTTILRTTMEAINLATTGSSPTVAKTTITTNTLAGSLFTLPLITPGMSTLASESVTSRTSYNHESWISTTSSYNRRYWTPACTPVTSTFSP    3744
GISTSSIPSSTA    3756
```

FIGURE 9

(cont.)

SEQUENCE LISTING

```
<160> NUMBER OF SEQ ID NOS: 13

<210> SEQ ID NO 1
<211> LENGTH: 330
<212> TYPE: DNA
<213> ORGANISM: Homo sapiens
<220> FEATURE:
<221> NAME/KEY: misc_feature
<222> LOCATION: (1)..(330)
<223> OTHER INFORMATION: Section of Human CA125 Antigen

<400> SEQUENCE: 1
tactaccagt cacacctaga cctggaggat ctgcaatgac tggaacttgc cggtgcctgg      60
ggtgcctttc ccccagccag ggtccaaaga agcttggctg gggcagaaat aaaccatatt     120
ggtcggaaaa aggaaggaga atacaacgtc cagcaacagt gcccaggcta ctaccagtcc     180
cccctagacc tggaggattt gcaatgactg gaacttgccg gtgcctgggg tgcctttccc     240
ccagccaggg tccaaaaaag cttggctggg gcaaaaataa acccatattg gtcggaaaaa     300
aaaaaaaaaa aaaaaaaaaa aaaaaaaaaa                                      330

<210> SEQ ID NO 2
<211> LENGTH: 666
<212> TYPE: PRT
<213> ORGANISM: Homo sapiens
<220> FEATURE:
<221> NAME/KEY: MISC_FEATURE
<222> LOCATION: (1)..(666)
<223> OTHER INFORMATION: Deduced amino acid sequence of CA125/MUC16A
      (B4), Part One

<400> SEQUENCE: 2

Arg Val Asp Pro Ile Gly Pro Gly Leu Asp Arg Glu Arg Leu Tyr Trp
1               5                  10                  15

Glu Leu Ser Gln Leu Thr Asn Ser Ile Thr Glu Leu Gly Pro Tyr Thr
            20                  25                  30

Leu Asp Arg Asp Ser Leu Tyr Val Asn Gly Leu Phe Lys Ser Thr Ser
        35                  40                  45

Val Gly Pro Leu Tyr Ser Gly Cys Arg Leu Thr Leu Leu Arg Pro Glu
    50                  55                  60

Lys His Gly Ala Ala Thr Gly Val Asp Ala Ile Cys Thr Leu Arg Leu
65                  70                  75                  80

Asp Pro Thr Gly Pro Gly Leu Asp Arg Glu Arg Leu Tyr Trp Glu Leu
                85                  90                  95

Ser Gln Leu Thr Asn Ser Val Thr Glu Leu Gly Pro Tyr Thr Leu Asp
            100                 105                 110
```

```
Arg Asp Ser Leu Tyr Val Asn Gly Leu Phe Lys Ser Thr Ser Val Gly
            115                 120                 125

Pro Leu Tyr Ser Gly Cys Arg Leu Thr Leu Leu Arg Pro Glu Lys Arg
        130                 135                 140

Gly Ala Ala Thr Gly Val Asp Thr Ile Cys Thr His Arg Leu Asp Pro
145                 150                 155                 160

Leu Asn Pro Gly Leu Asp Arg Glu Gln Leu Tyr Trp Glu Leu Ser Lys
                165                 170                 175

Leu Thr Arg Gly Ile Ile Glu Leu Gly Pro Tyr Leu Leu Asp Arg Gly
            180                 185                 190

Ser Leu Tyr Val Asn Gly Leu Phe Lys Asn Thr Ser Ile Gly Pro Leu
        195                 200                 205

Tyr Ser Ser Cys Arg Leu Thr Leu Leu Arg Pro Glu Lys Asp Lys Ala
    210                 215                 220

Ala Thr Arg Val Asp Ala Ile Cys Thr His His Pro Asp Pro Gln Ser
225                 230                 235                 240

Pro Gly Leu Asn Arg Glu Gln Leu Tyr Trp Glu Leu Ser Gln Leu Thr
                245                 250                 255

His Gly Ile Thr Glu Leu Gly Pro Tyr Thr Leu Asp Arg Asp Ser Leu
            260                 265                 270

Tyr Val Asp Gly Leu Phe Lys Ser Thr Ser Val Gly Pro Leu Tyr Ser
        275                 280                 285

Gly Cys Arg Leu Thr Leu Leu Arg Pro Glu Lys Asp Gly Val Ala Thr
    290                 295                 300

Arg Val Asp Ala Ile Cys Thr His Arg Pro Asp Pro Lys Ile Pro Gly
305                 310                 315                 320

Leu Asp Arg Gln Gln Leu Tyr Trp Glu Leu Ser Gln Leu Thr His Ser
                325                 330                 335

Ile Thr Glu Leu Gly Pro Tyr Thr Leu Asp Arg Asp Ser Leu Tyr Val
            340                 345                 350

Asn Gly Leu Phe Lys Asn Thr Ser Val Ser Ser Leu Tyr Ser Gly Cys
        355                 360                 365

Arg Leu Thr Leu Leu Arg Pro Glu Lys Asp Gly Ala Ala Thr Arg Val
    370                 375                 380

Asp Ala Val Cys Thr His Arg Pro Asp Pro Lys Ser Pro Gly Leu Asp
385                 390                 395                 400

Arg Glu Arg Leu Tyr Trp Lys Leu Ser Gln Leu Thr His Gly Ile Thr
                405                 410                 415

Glu Leu Gly Pro Tyr Thr Leu Asp Arg His Ser Leu Tyr Val Asn Gly
            420                 425                 430

Val Phe Lys Asn Thr Ser Val Gly Pro Leu Tyr Ser Gly Cys Arg Leu
        435                 440                 445

Thr Leu Leu Arg Pro Lys Lys Asp Gly Ala Ala Thr Lys Val Asp Ala
    450                 455                 460

Ile Cys Thr Tyr Arg Pro Asp Pro Lys Ser Pro Gly Leu Asp Arg Glu
465                 470                 475                 480

Gln Leu Tyr Trp Glu Leu Ser Gln Leu Thr His Ser Ile Thr Glu Leu
                485                 490                 495

Gly Pro Tyr Thr Leu Asp Arg Asp Ser Leu Tyr Val Asn Gly Leu Phe
            500                 505                 510

Lys Ser Thr Ser Val Gly Pro Leu Tyr Ser Gly Cys Arg Leu Thr Leu
        515                 520                 525
```

-continued

```
Leu Arg Pro Glu Lys Asp Gly Thr Ala Thr Gly Val Asp Ala Ile Cys
            530                 535                 540

Thr His His Pro Asp Pro Lys Ser Pro Arg Leu Asp Arg Glu Gln Leu
545                 550                 555                 560

Tyr Trp Glu Leu Ser Gln Leu Thr His Asn Ile Thr Glu Leu Gly Pro
                565                 570                 575

Tyr Ala Leu Asp Asn Asp Ser Leu Phe Val Asn Gly Leu Phe Lys Asn
            580                 585                 590

Thr Ser Val Gly Pro Leu Tyr Ser Gly Cys Arg Leu Thr Leu Leu Arg
        595                 600                 605

Pro Glu Lys Asp Gly Glu Ala Thr Gly Val Asp Ala Ile Cys Thr His
    610                 615                 620

Arg Pro Asp Pro Thr Gly Pro Gly Leu Asp Arg Glu Gln Leu Tyr Leu
625                 630                 635                 640

Glu Leu Ser Gln Leu Thr His Ser Ile Thr Glu Leu Gly Pro Tyr Thr
                645                 650                 655

Leu Asp Arg Asp Ser Leu Tyr Val Asn Gly
            660                 665

<210> SEQ ID NO 3
<211> LENGTH: 679
<212> TYPE: PRT
<213> ORGANISM: Homo sapiens
<220> FEATURE:
<221> NAME/KEY: MISC_FEATURE
<222> LOCATION: (1)..(679)
<223> OTHER INFORMATION: Deduced amino acid sequence of CA125/MUC16A
      (B4), Part Two

<400> SEQUENCE: 3

Phe Asn Pro Trp Ser Ser Val Pro Thr Thr Ser Thr Pro Gly Thr Ser
1               5                   10                  15

Thr Val His Leu Ala Thr Ser Gly Thr Pro Ser Ser Leu Pro Gly His
            20                  25                  30

Thr Ala Pro Val Pro Leu Leu Ile Pro Phe Thr Leu Asn Phe Thr Ile
        35                  40                  45

Thr Asn Leu His Tyr Glu Glu Asn Met Gln His Pro Gly Ser Arg Lys
    50                  55                  60

Phe Asn Thr Thr Glu Arg Val Leu Gln Gly Leu Leu Lys Pro Phe Thr
65                  70                  75                  80

His Arg Ser Ser Val Pro Thr Thr Ser Ile Pro Gly Thr Ser Ala Val
                85                  90                  95

His Leu Glu Thr Ser Gly Thr Pro Ala Ser Leu Pro Gly His Thr Ala
            100                 105                 110

Pro Gly Pro Leu Leu Val Pro Phe Thr Leu Asn Phe Thr Ile Thr Asn
        115                 120                 125

Leu Gln Tyr Glu Glu Asp Met Arg His Pro Gly Ser Arg Lys Phe Asn
    130                 135                 140

Thr Thr Glu Arg Val Leu Gln Gly Leu Leu Lys Pro Phe Thr His Arg
145                 150                 155                 160

Asn Phe Val Pro Ile Thr Ser Pro Gly Thr Ser Thr Val His Leu
                165                 170                 175

Gly Thr Ser Glu Thr Pro Ser Ser Leu Pro Arg Pro Ile Val Pro Gly
            180                 185                 190

Pro Leu Leu Val Pro Phe Thr Leu Asn Phe Thr Ile Thr Asn Leu Gln
        195                 200                 205
```

-continued

```
Tyr Glu Glu Ala Met Arg His Pro Gly Ser Arg Lys Phe Asn Thr Thr
    210                 215                 220

Glu Arg Val Leu Gln Gly Leu Leu Arg Pro Phe Thr His Trp Ser Pro
225                 230                 235                 240

Ile Pro Thr Thr Ser Thr Pro Gly Thr Ser Ile Val Asn Leu Gly Thr
                245                 250                 255

Ser Gly Ile Pro Pro Ser Leu Pro Glu Thr Thr Ala Thr Gly Pro Leu
            260                 265                 270

Leu Val Pro Phe Thr Leu Asn Phe Thr Ile Thr Asn Leu Gln Tyr Glu
        275                 280                 285

Glu Asn Met Gly His Pro Gly Ser Arg Lys Phe Asn Ile Thr Glu Ser
    290                 295                 300

Val Leu Gln Gly Leu Leu Lys Pro Phe Thr Gln Arg Ser Ser Val Pro
305                 310                 315                 320

Thr Thr Ser Thr Pro Gly Thr Phe Thr Val Gln Pro Glu Thr Ser Glu
                325                 330                 335

Thr Pro Ser Ser Leu Pro Gly Pro Thr Ala Thr Gly Pro Val Leu Leu
            340                 345                 350

Pro Phe Thr Leu Asn Phe Thr Ile Ile Asn Leu Gln Tyr Glu Glu Asp
        355                 360                 365

Met His Arg Pro Gly Ser Arg Lys Phe Asn Thr Thr Glu Arg Val Leu
    370                 375                 380

Gln Gly Leu Leu Met Pro Phe Thr His Gln Ser Ser Met Thr Thr Thr
385                 390                 395                 400

Arg Thr Pro Asp Thr Ser Thr Met His Leu Ala Thr Ser Arg Thr Pro
                405                 410                 415

Ala Ser Leu Ser Gly Pro Thr Thr Ala Ser Pro Leu Leu Val Leu Phe
            420                 425                 430

Thr Ile Asn Phe Thr Ile Thr Asn Leu Arg Tyr Glu Glu Asn Met His
        435                 440                 445

His Pro Gly Ser Arg Lys Phe Asn Thr Thr Glu Arg Val Leu Gln Gly
    450                 455                 460

Leu Leu Arg Pro Phe Thr Gln Arg Ser Ser Val Pro Thr Thr Ser Ile
465                 470                 475                 480

Pro Gly Thr Pro Thr Val Asp Leu Gly Thr Ser Gly Thr Pro Val Ser
                485                 490                 495

Lys Pro Gly Pro Ser Ala Ala Ser Pro Leu Leu Val Leu Phe Thr Leu
            500                 505                 510

Asn Phe Thr Ile Thr Asn Leu Arg Tyr Glu Glu Asn Met Gln His Pro
        515                 520                 525

Gly Ser Arg Lys Phe Asn Thr Thr Glu Arg Val Leu Gln Gly Leu Leu
    530                 535                 540

Arg Ser Phe Thr His Arg Ser Ser Val Ser Thr Thr Ser Thr Pro Gly
545                 550                 555                 560

Thr Pro Thr Val Tyr Leu Gly Ala Ser Lys Thr Pro Ala Ser Ile Phe
                565                 570                 575

Gly Pro Ser Ala Ala Ser His Leu Leu Ile Leu Phe Thr Leu Asn Phe
            580                 585                 590

Thr Ile Thr Asn Leu Arg Tyr Glu Glu Asn Met Trp Pro Gly Ser Arg
        595                 600                 605

Lys Phe Asn Thr Thr Glu Arg Val Leu Gln Gly Leu Leu Arg Pro Phe
610                 615                 620
```

```
Thr His Arg Ser Ser Val Pro Thr Thr Ser Thr Gly Val Val Ser Glu
625                 630                 635                 640

Glu Pro Phe Thr Leu Asn Phe Thr Ile Asn Asn Leu Arg Tyr Met Ala
                645                 650                 655

Asp Met Gly Gln Pro Gly Ser Leu Lys Phe Asn Ile Thr Asp Asn Val
            660                 665                 670

Met Gln His Leu Leu Ser Pro
        675

<210> SEQ ID NO 4
<211> LENGTH: 545
<212> TYPE: PRT
<213> ORGANISM: Homo sapiens
<220> FEATURE:
<221> NAME/KEY: MISC_FEATURE
<222> LOCATION: (1)..(545)
<223> OTHER INFORMATION: Deduced amino acid sequence of CA125/MUC16A
      (B4), Part Three

<400> SEQUENCE: 4

Leu Phe Gln Arg Ser Ser Leu Gly Ala Arg Tyr Thr Gly Cys Arg Val
1               5                   10                  15

Ile Ala Leu Arg Ser Val Lys Asn Gly Ala Glu Thr Arg Val Asp Leu
                20                  25                  30

Leu Cys Thr Tyr Leu Gln Pro Leu Ser Gly Pro Gly Leu Pro Ile Lys
            35                  40                  45

Gln Val Phe His Glu Leu Ser Gln Gln Thr His Gly Ile Thr Arg Leu
        50                  55                  60

Gly Pro Tyr Ser Leu Asp Lys Asp Ser Leu Tyr Leu Asn Gly Tyr Asn
65                  70                  75                  80

Glu Pro Gly Leu Asp Glu Pro Pro Thr Thr Pro Lys Pro Ala Thr Thr
                85                  90                  95

Phe Leu Pro Pro Leu Ser Glu Ala Thr Thr Ala Met Gly Tyr His Leu
            100                 105                 110

Lys Thr Leu Thr Leu Asn Phe Thr Ile Ser Asn Leu Gln Tyr Ser Pro
        115                 120                 125

Asp Met Gly Lys Gly Ser Ala Thr Phe Asn Ser Thr Glu Gly Val Leu
130                 135                 140

Gln His Leu Leu Arg Pro Leu Phe Gln Lys Ser Ser Met Gly Pro Phe
145                 150                 155                 160

Tyr Leu Gly Cys Gln Leu Ile Ser Leu Arg Pro Glu Lys Asp Gly Ala
                165                 170                 175

Ala Thr Gly Val Asp Thr Thr Cys Thr Tyr His Pro Asp Pro Val Gly
            180                 185                 190

Pro Gly Leu Asp Ile Gln Gln Leu Tyr Trp Glu Leu Ser Gln Leu Thr
        195                 200                 205

His Gly Val Thr Gln Leu Gly Phe Tyr Val Leu Asp Arg Asp Ser Leu
    210                 215                 220

Phe Ile Asn Gly Tyr Ala Pro Gln Asn Leu Ser Ile Arg Gly Glu Tyr
225                 230                 235                 240

Gln Ile Asn Phe His Ile Val Asn Trp Asn Leu Ser Asn Pro Asp Pro
                245                 250                 255

Thr Ser Ser Glu Tyr Ile Thr Leu Leu Arg Asp Ile Gln Asp Lys Val
            260                 265                 270

Thr Thr Leu Tyr Lys Gly Ser Gln Leu His Asp Thr Phe Arg Phe Cys
        275                 280                 285
```

```
Leu Val Thr Asn Leu Thr Met Asp Ser Val Leu Val Thr Val Lys Ala
    290                 295                 300

Leu Phe Ser Ser Asn Leu Asp Pro Ser Leu Val Glu Gln Val Phe Leu
305                 310                 315                 320

Asp Lys Thr Leu Asn Ala Ser Phe His Trp Leu Gly Ser Thr Tyr Gln
                325                 330                 335

Leu Val Asp Ile His Val Thr Glu Met Glu Ser Ser Val Tyr Gln Pro
            340                 345                 350

Thr Ser Ser Ser Ser Thr Gln His Phe Tyr Pro Asn Phe Thr Ile Thr
        355                 360                 365

Asn Leu Pro Tyr Ser Gln Asp Lys Ala Gln Pro Gly Thr Thr Asn Tyr
370                 375                 380

Gln Arg Asn Lys Arg Asn Ile Glu Asp Ala Leu Asn Gln Leu Phe Arg
385                 390                 395                 400

Asn Ser Ser Ile Lys Ser Tyr Phe Ser Asp Cys Gln Val Ser Thr Phe
                405                 410                 415

Arg Ser Val Pro Asn Arg His His Thr Gly Val Asp Ser Leu Cys Asn
            420                 425                 430

Phe Ser Pro Leu Ala Arg Arg Val Asp Arg Val Ala Ile Tyr Glu Glu
        435                 440                 445

Phe Leu Arg Met Thr Arg Asn Gly Thr Gln Leu Gln Asn Phe Thr Leu
450                 455                 460

Asp Arg Ser Ser Val Leu Val Asp Gly Tyr Ser Pro Asn Arg Asn Glu
465                 470                 475                 480

Pro Leu Thr Gly Asn Ser Asp Leu Pro Phe Trp Ala Val Ile Phe Ile
                485                 490                 495

Gly Leu Ala Gly Leu Leu Gly Leu Ile Thr Cys Leu Ile Cys Gly Val
            500                 505                 510

Leu Val Thr Thr Arg Arg Arg Lys Lys Glu Gly Glu Tyr Asn Val Gln
        515                 520                 525

Gln Gln Cys Pro Gly Tyr Tyr Gln Ser His Leu Asp Leu Glu Asp Leu
530                 535                 540

Gln
545

<210> SEQ ID NO 5
<211> LENGTH: 5965
<212> TYPE: DNA
<213> ORGANISM: Homo sapiens
<220> FEATURE:
<221> NAME/KEY: misc_feature
<222> LOCATION: (1)..(5965)
<223> OTHER INFORMATION: Nucleotide sequence of B4 polynucleotide
      (CA125/MUC16A)

<400> SEQUENCE: 5
cgcgttgatc ccatcggacc tggactggac agagagcggc tatactggga gctgagccag      60
ctgaccaaca gcatcacaga gctgggaccc tacaccctgg atagggacag tctctatgtc     120
aatggcttca acccttggag ctctgtgcca accaccagca ctcctgggac ctccacagtg     180
cacctggcaa cctctgggac tccatcctcc ctgcctggcc acacagcccc tgtccctctc     240
ttgataccat tcaccctcaa ctttaccatc accaacctgc attatgaaga aacatgcaa      300 caccctggtt ccaggaagtt caacaccacg agagggttc tgcagggtct gctcaagccc      360
ttgttcaaga gcaccagcgt tggccctctg tactctggct gcagactgac cttgctcaga      420
cctgagaaac atgggcagc cactggagtg gacgccatct gcaccctccg ccttgatccc      480
```

-continued

```
actggtcctg gactggacag agagcggcta tactgggagc tgagccagct gaccaacagc    540
gttacagagc tgggcccctá caccctggac agggacagtc tctatgtcaa tggcttcacc    600
catcggagct ctgtgccaac caccagtatt cctgggacct ctgcagtgca cctggaaacc    660
tctgggactc cagcctccct ccctggccac acagccctg ccctctcct ggtgccattc     720 accctcaact tcactatcac caacctgcag tatgaggagg acatgcgtca ccctggttcc    780
aggaagttca acaccacgga gagagtcctg cagggtctgc tcaagccctt gttcaagagc    840
accagtgttg ccctctgta ctctggctgc agactgacct tgctcaggcc tgaaaaacgt     900
ggggcagcca ccgcgtgga caccatctgc actaccgcc ttgaccctct aaaccctgga      960
ctggacagag agcagctata ctgggagctg agcaaactga cccgtggcat catcgagctg   1020
ggcccctacc tcctggacag aggcagtctc tatgtcaatg gtttcaccca tcggaacttt   1080
gtgcccatca ccagcactcc tgggacctcc acagtacacc taggaaccctc tgaaactcca  1140 tcctccctac ctagacccat agtgcctggc cctctcctgg tgccattcac cctcaacttc   1200
accatcacca acttgcagta tgaggaggcc atgcgacacc ctggctccag gaagttcaat   1260
accacggaga gggtcctaca gggtctgctc aggcccttgt tcaagaatac cagtatcggc   1320
cctctgtact ccagctgcag actgaccttg ctcaggccag agaaggacaa ggcagccacc   1380
agagtggatg ccatctgtac ccaccaccct gaccctcaaa gccctggact gaacagagag   1440
cagctgtact gggagctgag ccagctgacc cacggcatca ctgagctggg ccctacacc   1500 ctggacaggg acagtctcta tgtcgatggt ttcactcatt ggagccccat accaaccacc   1560
agcactcctg ggacctccat agtgaacctg ggaacctctg ggatcccacc ttccctccct   1620
gaaactacag ccaccggccc tctcctggtg ccattcacac tcaacttcac catcactaac   1680
ctacagtatg aggagaacat gggtcaccct ggctccagga agttcaacat cacggagagt   1740
gttctgcagg gtctgctcaa gcccttgttc aagagcacca gtgttggccc tctgtattct   1800
ggctgcagac tgaccttgct caggcctgag aaggacggag tagccaccag agtggacgcc   1860
atctgcaccc accgccctga ccccaaaatc cctgggctag acagacagca gctatactgg   1920
gagctgagcc agctgaccca cagcatcact gagctgggac cctacaccct ggatagggac   1980
agtctctatg tcaatggttt cacccagcgg agctctgtgc ccaccaccag cactcctggg   2040
actttcacag tacagccgga aacctctgag actccatcat ccctccctgg ccccacagcc   2100
actggccctg tcctgctgcc attcaccctc aattttacca tcattaacct gcagtatgag   2160
gaggacatgc atcgccctgg ctccaggaag ttcaacacca cggagagggt ccttcagggt   2220
ctgcttatgc ccttgttcaa gaacaccagt gtcagctctc tgtactctgg ttgcagactg   2280
accttgctca ggcctgagaa ggatggggca gccaccagag tggatgctgt ctgcacccat   2340
cgtcctgacc ccaaaagccc tggactggac agagagcggc tgtactggaa gctgagccag   2400
ctgacccacg catcactga gctgggcccc tacaccctgg acaggacag tctctatgtc    2460 aatggtttca cccatcagag ctctatgacg accaccagaa ctcctgatac ctccacaatg   2520
cacctggcaa cctcgagaac tccagcctcc ctgtctggac tacgaccgc cagccctctc   2580 ctggtgctat tcacaattaa cttcaccatc actaacctgc ggtatgagga gaacatgcat   2640 cacccctggct ctagaaagtt taacaccacg agagagtcc ttcagggtct gctcaggcct   2700
gtgttcaaga acaccagtgt tggccctctg tactctggct gcagactgac cttgctcagg   2760
cccaagaagg atggggcagc caccaaagtg atgccatct gcacctaccg ccctgatccc   2820
aaaagccctg gactggacag agagcagcta tactgggagc tgagccagct aacccacagc   2880
```

-continued

```
atcactgagc tgggccccta caccctggac agggacagtc tctatgtcaa tggtttcaca    2940
cagcggagct ctgtgcccac cactagcatt cctgggaccc ccacagtgga cctgggaaca    3000
tctgggactc cagtttctaa acctggtccc tcggctgcca gccctctcct ggtgctattc    3060
actctcaact tcaccatcac caacctgcgg tatgaggaga acatgcagca ccctggctcc    3120
aggaagttca acaccacgga gagggtcctt cagggcctgc tcaggtccct gttcaagagc    3180
accagtgttg gccctctgta ctctggctgc agactgactt tgctcaggcc tgaaaaggat    3240
gggacagcca ctggagtgga tgccatctgc acccaccacc ctgacccaa aagccctagg     3300 ctggacagag agcagctgta ttgggagctg agccagctga cccacaatat cactgagctg    3360
ggcccctatg ccctggacaa cgacagcctc tttgtcaatg gtttcactca tcggagctct    3420
gtgtccacca ccagcactcc tgggaccccc acagtgtatc tgggagcatc taagactcca    3480
gcctcgatat ttggcccttc agctgccagc catctcctga tactattcac cctcaacttc    3540
accatcacta acctgcggta tgaggagaac atgtggcctg ctccaggaa gttcaacact     3600 acagagaggg tccttcaggg cctgctaagg cccttgttca agaacaccag tgttggccct    3660
ctgtactctg gctgcaggct gaccttgctc aggccagaga agatggggga agccaccgga    3720
gtggatgcca tctgcaccca ccgccctgac cccacaggcc ctgggctgga cagagagcag    3780
ctgtatttgg agctgagcca gctgacccac agcatcactg agctgggccc ctacacactg    3840
gacagggaca gtctctatgt caatggtttc acccatcgga gctctgtacc caccaccagc    3900
accggggtgg tcagcgagga gccattcaca ctgaacttca ccatcaacaa cctgcgctac    3960
atggcggaca tgggccaacc cggctccctc aagttcaaca tcacagacaa cgtcatgcag    4020
cacctgctca gtcctttgtt ccagaggagc agcctgggtg cacggtacac aggctgcagg    4080
gtcatcgcac taaggtctgt gaagaacggt gctgagacac gggtggacct cctctgcacc    4140
tacctgcagc ccctcagcgg cccaggtctg cctataagc aggtgttcca tgagctgagc     4200
cagcagaccc atggcatcac ccggctgggc ccctactctc tggacaaaga cagcctctac    4260
cttaacggtt acaatgaacc tggtccagat gagcctccta caactcccaa gccagccacc    4320
acattcctgc ctcctctgtc agaagccaca acagccatgg ggtaccacct gaagaccctc    4380
acactcaact tcaccatctc caatctccag tattcaccag atatgggcaa gggctcagct    4440
acattcaact ccaccgaggg ggtccttcag cacctgctca gaccccttgtt ccagaagagc    4500 agcatgggcc ccttctactt gggttgccaa ctgatctccc tcaggcctga gaaggatggg    4560
gcagccactg gtgtggacac cacctgcacc taccaccctg accctgtggg ccccgggctg    4620
gacatacagc agcttactg ggagctgagt cagctgaccc atggtgtcac ccaactgggc     4680
ttctatgtcc tggacaggga tagcctcttc atcaatggct atgcacccca gaatttatca    4740
atccggggcg agtaccagat aaatttccac attgtcaact ggaacctcag taatccagac    4800
cccacatcct cagagtacat caccctgctg agggacatcc aggacaaggt caccacactc    4860
tacaaaggca gtcaactaca tgacacattc cgcttctgcc tggtcaccaa cttgacgatg    4920
gactccgtgt tggtcactgt caaggcattg ttctcctcca atttggaccc cagcctggtg    4980
gagcaagtct ttctagataa gaccctgaat gcctcattcc attggctggg ctccacctac    5040
cagttggtgg acatccatgt gacagaaatg gagtcatcag tttatcaacc aacaagcagc    5100
tccagcaccc agcacttcta cccgaatttc accatcacca acctaccata ttcccaggac    5160
aaagcccagc aggcaccac caattaccag aggaacaaaa ggaatattga ggatgcgctc    5220
aaccaactct tccgaaacag cagcatcaag agttatttttt ctgactgtca gtttcaaca    5280
```

```
ttcaggtctg tccccaacag gcaccacacc ggggtggact ccctgtgtaa cttctcgcca    5340
ctggctcgga gagtagacag agttgccatc tatgaggaat ttctgcggat gacccggaat    5400
ggtacccagc tgcagaactt caccctggac aggagcagtg tccttgtgga tgggtattct    5460
cccaacagaa atgagccctt aactgggaat tctgaccttc ccttctgggc tgtcatcttc    5520
atcggcttgg caggactcct gggactcatc acatgcctga tctgcggtgt cctggtgacc    5580
acccgccggc ggaagaagga aggagaatac aacgtccagc aacagtgccc aggctactac    5640
cagtcacacc tagacctgga ggatctgcaa tgactggaac ttgccggtgc ctggggtgcc    5700
tttcccccag ccagggtcca agaagcttg gctggggcag aaataaacca tattggtcgg    5760
aaaaaggaag gagaatacaa cgtccagcaa cagtgcccag gctactacca gtcccccta    5820 gacctggagg atttgcaatg actggaactt gccggtgcct ggggtgcctt tcccccagcc    5880
agggtccaaa aaagcttggc tggggcaaaa ataaaccata ttggtcggaa aaaaaaaa    5940 aaaaaaaaaa aaaaaaaaaa aaaaa                                          5965
```

<210> SEQ ID NO 6
<211> LENGTH: 558
<212> TYPE: DNA
<213> ORGANISM: Homo sapiens
<220> FEATURE:
<221> NAME/KEY: misc_feature
<222> LOCATION: (1)..(558)
<223> OTHER INFORMATION: 3' Sequence of Clone B30
<220> FEATURE:
<221> NAME/KEY: misc_feature
<222> LOCATION: (212)..(212)
<223> OTHER INFORMATION: n can be a, c, g, or t
<220> FEATURE:
<221> NAME/KEY: misc_feature
<222> LOCATION: (227)..(227)
<223> OTHER INFORMATION: n can be a, c, g, or t

<400> SEQUENCE: 6

```
tgagtattct actgatgttc ccatggcccc aatcttacaa caaacttagc aggagctgac      60
ccctattcat aagcccttat gtcctttcca taagggaagg aacatagagg acacaaatta     120 ttcccttcc ccactgcccc agctaatcag agtcccagct gaagcccac aggcaaaaat     180 ccccatgaat agtccctcct gctggcatta cnttccatga gagcacnttg ctcctttcac     240
tgttgagggc ttctcctcag ctcctgggac tttcacagta cagccggaaa cctctgagac     300
tccatcatcc ctccctggcc ccacaggtaa ataccagtca atggtatttg gagcatggtt     360
gatgagtgta aacatctctg tttatactct gttagagcat ggttgatgag tgtaaacatc     420
tctgtcatta ttcactcaac taagatggaa aattcatagt aaatgtagta accataggtc     480
aaccaaccca gttcattgag cactgcctct gtatcaggac ctggatatac atcagggaac     540
aaaaaaaaaa aaaaaaaa                                                    558
```

<210> SEQ ID NO 7
<211> LENGTH: 18364
<212> TYPE: DNA
<213> ORGANISM: Homo sapiens
<220> FEATURE:
<221> NAME/KEY: misc_feature
<222> LOCATION: (1)..(18364)
<223> OTHER INFORMATION: Nucleotide sequence of MUC16B
<220> FEATURE:
<221> NAME/KEY: misc_feature
<222> LOCATION: (18019)..(18019)
<223> OTHER INFORMATION: n can be a, c, g, or t
<220> FEATURE:
<221> NAME/KEY: misc_feature
<222> LOCATION: (18034)..(18034)
<223> OTHER INFORMATION: n can be a, c, g, or t

<400> SEQUENCE: 7

| | |
|---|---|
| cctgtgactt ctcttctcac ccctggcctg gtgataacca cagacaggat gggcataagc | 60 |
| agagaacctg gaaccagttc cacttcaaat ttgagcagca cctcccatga gagactgacc | 120 |
| actttggaag acactgtaga tacagaagcc atgcagcctt ccacacacac agcagtgacc | 180 |
| aacgtgagga cctccatttc tggacatgaa tcacaatctt ctgtcctatc tgactcagag | 240 |
| acacccaaag ccacatctcc aatgggtacc acctacacca tgggggaaac gagtgtttcc | 300 |
| atatccactt ctgacttctt tgagaccagc agaattcaga tagaaccaac atcctccctg | 360 |
| acttctggat tgagggagac cagcagctct gagaggatca gctcagccac agagggaagc | 420 |
| actgtccttt ctgaagtgcc cagtggtgct accactgagg tctccaggac agaagtgata | 480 |
| tcctctaggg gaacatccat gtcagggcct gatcagttca ccatatcacc agacatctct | 540 |
| actgaagcga tcaccaggct ttctacttcc cccattatga cagaatcagc agaaagtgcc | 600 |
| atcactattg agacaggttc tcctggggct acatcagagg gtaccctcac cttggacacc | 660 |
| tcaacaacaa ccttttggtc agggacccac tcaactgcat ctccaggatt ttcacactca | 720 |
| gagatgacca ctcttatgag tagaactcct ggagatgtgc catggccgag ccttccctct | 780 |
| gtggaagaag ccagctctgt ctcttcctca ctgtcttcac ctgccatgac ctcaacttct | 840 |
| tttttctcca cattaccaga gagcatctcc tcctctcctc atcctgtgac tgcacttctc | 900 |
| acccttggcc cagtgaagac cacagacatg ttgcgcacaa gctcagaacc tgaaaccagt | 960 |
| tcacctccaa atttgagcag cacctcagct gaaatattag ccacgtctga agtcaccaaa | 1020 |
| gatagagaga aaattcatcc ctcctcaaac acacctgtag tcaatgtagg gactgtgatt | 1080 |
| tataaacatc tatcccctt ctctgtttg gctgacttag tgacaacaaa acccacatct | 1140 |
| ccaatggcta ccacctccac tctggggaat acaagtgttt ccacatcaac tcctgccttc | 1200 |
| ccagaaacta tgatgacaca gccaacttcc tccctgactt ctggattaag ggagatcagt | 1260 |
| acctctcaag agaccagctc agcaacagag agaagtgctt ctctttctgg aatgcccact | 1320 |
| ggtgctacta ctaaggtctc cagaacagaa gccctctcct taggcagaac atccaccca | 1380 |
| ggtcctgctc aatccacaat atcaccagaa atctccacgg aaaccatcac tagaatttct | 1440 |
| actcccctca ccacgacagg atcagcagaa atgaccatca cccccaaaac aggtcattct | 1500 |
| ggggcatcct cacaaggtac ctttaccttg gacacatcaa gcagagcctc ctggccagga | 1560 |
| actcactcag ctgcaactca cagatctcca cactcaggga tgaccactcc tatgagcaga | 1620 |
| ggtcctgagg atgtgtcatg gccaagccgc ccatcagtgg aaaaaactag ccctccatct | 1680 |
| tccctggtgt ctttatctgc agtaacctca ccttcgccac tttattccac accatctgag | 1740 |
| agtagccact cgtctcctct ccgggtgact tctcttttca ccccctgtcat gatgaagacc | 1800 |
| acagacatgt tggacacaag cttggaacct gtgaccactt cacctcccag tatgaatatc | 1860 |
| acctcagatg agagtctggc cacttctaaa gccaccatgg agacagaggc aattcagctt | 1920 |
| tcagaaaaca cagctgtgac tcagatgggc accatcagtg ctagacaaga attctattcc | 1980 |
| tcttatccag gcctcccaga gccatccaaa gtgacatctc cagtggtcac ctcttccacc | 2040 |
| ataaaagaca ttgtttctac aaccatacct gcttcctctg agataacaag aattgagatg | 2100 |
| gagtcaacat ccaccctgac ccccacacca agggagacca gcacctccca ggagatccac | 2160 |

```
tcagccacaa agccaagcac tgttccttac aaggcactca ctagtgccac gattgaggac    2220
tccatgacac aagtcatgtc ctctagcaga ggacctagcc ctgatcagtc cacaatgtca    2280
caagacatat ccactgaagt gatcaccagg ctctctacct cccccatcaa gacagaatct    2340
acagaaatga ccattaccac ccaaacaggt tctcctgggg ctacatcaag gggtacccct    2400
accttggaca cttcaacaac ttttatgtca gggacccatt caactgcatc tcaaggattt    2460
tcacactcac agatgaccgc tcttatgagt agaactcctg gagaggtgcc atggctaagc    2520
catccctctg tggaagaagc cagctctgcc tctttctcac tgtcttcacc tgtcatgacc    2580
tcatcttctc ccgtttcttc cacattacca gacagcatcc actcttcttc gcttcctgtg    2640
acatcacttc tcacctcagg gctggtgaag accacagagc tgttgggcac aagctcagaa    2700
cctgaaacca gttcaccccc aaatttgagc agcacctcag ctgaaatact ggccaccact    2760
gaagtcacta cagatacaga gaaactggag atgaccaatg tggtaacctc aggttataca    2820
catgaatctc cttcctctgt cctagctgac tcagtgacaa caaaggccac atcttcaatg    2880
ggtatcacct accccacagg agatacaaat gttctcacat caaccccctgc cttctctgac    2940
accagtagga ttcaaacaaa gtcaaagctc tcactgactc ctgggttgat ggagaccagc    3000
atctctgaag agaccagctc tgccacagaa aaaagcactg tcctttctag tgtgcccact    3060
ggtgctacta ctgaggtctc caggacagaa gccatctctt ctagcagaac atccatccca    3120
ggccctgctc aatccacaat gtcatcagac acctccatgg aaaccatcac tagaatttct    3180
accccccctca aaggaaaga atcaacagac atggccatca cccccaaaac aggtccttct    3240
ggggctacct cgcagggtac ctttaccttg gactcatcaa gcacagcctc ctggccagga    3300
actcactcag ctacaactca gagatttcca cggtcagtgg tgacaactcc tatgagcaga    3360
ggtcctgagg atgtgtcatg gccaagcccg ctgtctgtgg aaaaaaacag ccctccatct    3420
tccctggtat cttcatcttc agtaacctca ccttcgccac tttattccac accatctggg    3480
agtagccact cctctcctgt ccctgtcact tctcttttca cctctatcat gatgaaggcc    3540
acagacatgt tggatgcaag tttggaacct gagaccactt cagctcccaa tatgaatatc    3600
acctcagatg agagtctggc cgcttctaaa gccaccacgg agacagaggc aattcacgtt    3660
tttgaaaata cagcagcgtc ccatgtggaa accaccagtg ctacagagga actctattcc    3720
tcttccccag gcttctcaga gccaacaaaa gtgatatctc cagtggtcac ctcttcctct    3780
ataagagaca acatggtttt cacaacaatg cctggctcct ctggcattac aaggattgag    3840
atagagtcaa tgtcatctct gaccccctgga ctgagggaga ccagaacctc ccaggacatc    3900
acctcatcca cagagacaag cactgtcctt tacaagatgc cctctggtgc cactcctgag    3960
gtctccagga cagaagttat gccctctagc agaaacatcca ttcctggccc tgctcagtcc    4020
acaatgtcac tagacatctc cgatgaagtt gtcaccaggc tgtctacctc tcccatcatg    4080
acagaatctg cagaaataac catcaccacc caaacaggtt attctctggc tacatcccag    4140
gttacccttc ccttgggcac ctcaatgacc ttttttgtcag ggacccactc aactatgtct    4200
caaggacttt cacactcaga gatgaccaat cttatgagca ggggtcctga agtctgtca    4260
tggacgagcc ctcgctttgt ggaaacaact agatcttcct cttctctgac atcattacct    4320
ctcacgacct cactttctcc tgtgtcctcc acattactag acagtagccc ctcctctcct    4380
cttcctgtga cttcacttat cctcccaggc ctggtgaaga ctacagaagt gttggataca    4440
agctcagagc ctaaaaccag ttcatctcca aatttgagca gcacctcagt tgaaataccg    4500
gccacctctg aaatcatgac agatacagag aaaattcatc cttcctcaaa cacagcggtg    4560
```

```
gccaaagtga ggacctccag ttctgttcat gaatctcatt cctctgtcct agctgactca  4620
gaaacaacca taaccatacc ttcaatgggt atcacctccg ctgtggagga taccactgtt  4680
ttcacatcaa atcctgcctt ctctgagact aggaggattc cgacagagcc aacattctca  4740
ttgactcctg gattcaggga gactagcacc tctgaagaga ccacctcaat cacagaaaca  4800
agtgcagtcc tttttggagt gcccactagt gctactactg aagtctccat gacagaaata  4860
atgtcctcta atagaacaca catccctgac tctgatcagt ccacgatgtc tccagacatc  4920
atcactgaag tgatcaccag gctctcttcc tcatccatga tgtcagaatc aacacaaatg  4980
accatcacca cccaaaaaag ttctcctggg gctacagcac agagtactct taccttggcc  5040
acaacaacag cccccttggc aaggacccac tcaactgttc ctcctagatt tttacactca  5100
gagatgacaa ctcttatgag taggagtcct gaaaatccat catggaagag ctctccctt t  5160 gtggaaaaaa ctagctcttc atcttctctg ttgtccttac ctgtcacgac ctcaccttct  5220
gtttcttcca cattaccgca gagtatccct tcctcctctt tttctgtgac ttcactcctc  5280
accccaggca tggtgaagac tacagacaca agcacagaac ctggaaccag tttatctcca  5340
aatctgagtg gcacctcagt tgaaatactg gctgcctctg aagtcaccac agatacagag  5400
aaaattcatc cttcttcaag catggcagtg accaatgtgg aaccaccag ttctggacat  5460 gaactatatt cctctgtttc aatccactcg gagccatcca aggctacata cccagtgggt  5520
actccctctt ccatggctga aacctctatt tccacatcaa tgcctgctaa ttttgagacc  5580
acaggatttg aggctgagcc attttctcat ttgacttctg gacttaggaa gaccaacatg  5640
tccctggaca ccagctcagt cacaccaaca aatacacctt cttctcctgg gtccactcac  5700
cttttacaga gttccaagac tgatttcacc tcttctgcaa aaacatcatc cccagactgg  5760
cctccagcct cacagtatac tgaaattcca gtggacataa tcaccccctt taatgcttct  5820
ccatctatta cggagtccac tgggataacc tccttcccag aatccaggtt tactatgtct  5880
gtaacagaaa gtactcatca tctgagtaca gatttgctgc cttcagctga gactatttcc  5940
actggcacag tgatgccttc tctatcagag gccatgactt catttgccac cactggagtt  6000
ccacgagcca tctcaggttc aggtagtcca ttctctagga cagagtcagg ccctggggat  6060
gctactctgt ccaccattgc agagagcctg ccttcatcca ctcctgtgcc attctcctct  6120
tcaaccttca ctaccactga ttcttcaacc atcccagccc tccatgagat aacttcctct  6180
tcagctaccc catatagagt ggacaccagt cttgggacag agagcagcac tactgaagga  6240
cgcttggtta tggtcagtac tttggacact tcaagccaac caggcaggac atcttcatca  6300
cccattttgg ataccagaat gacagagagc gttgagctgg gaacagtgac aagtgcttat  6360
caagttcctt cactctcaac acggttgaca agagatggca ttatgaaaca catcacaaaa  6420
atacccaatg aagcagcaca cagaggtacc ataagaccag tcaaaggccc tcagacatcc  6480
acttcgcctg ccagtcctaa aggactacac acaggaggga caaaaagaat ggagaccacc  6540
accacagctc tgaagaccac caccacagct ctgaagacca cttccagagc caccttgacc  6600
accagtgtct atactcccac tttgggaaca ctgactcccc tcaatgcatc aatgcaaatg  6660
gccagcacaa tccccacaga aatgatgatc acaaccccat atgttttccc tgatgttcca  6720
gaaacgacat cctcattggc taccagcctg ggagcagaaa ccagcacagc tcttcccagg  6780
acaaccccat ctgttttcaa tagagaatca gagaccacag cctcactggt ctctcgttct  6840 gggcagaga gaagtccggt tattcaaact ctagatgttt cttctagtga gccagataca  6900
acagcttcat gggttatcca tcctgcagag accatcccaa ctgtttccaa gacaaccccc  6960
```

```
aatttttcc acagtgaatt agacactgta tcttccacag ccaccagtca tggggcagac    7020
gtcagctcag ccattccaac aaatatctca cctagtgaac tagatgcact gaccccactg    7080
gtcactattt cggggacaga tactagtaca acattcccaa cactgactaa gtccccacat    7140
gaaacagaga caagaaccac atggctcact catcctgcag agaccagctc aactattccc    7200
agaacaatcc ccaattttc tcatcatgaa tcagatgcca caccttcaat agccaccagt    7260
cctggggcag aaaccagttc agctattcca attatgactg tctcacctgg tgcagaagat    7320
ctggtgacct cacaggtcac tagttctggc acagacagaa atatgactat tccaactttg    7380
actctttctc ctggtgaacc aaagaccata gcctcattag tcacccatcc tgaagcacag    7440
acaagttcgg ccattccaac ttcaactatc tcgcctgctg tatcacggtt ggtgacctca    7500
atggtcacca gtttggcggc aaagacaagt acaactaatc gagctctgac aaactcccct    7560
ggtgaaccag ctacaacagt tcattggtc acgcattctg cacagaccag cccaacagtt    7620
ccctggacaa cttccatttt tttccatagt aaatcagaca ccacccttc aatgaccacc    7680 agtcatgggg cagaatccag ttcagctgtt ccaactccaa ctgtttcaac tgaggtacca    7740
ggagtagtga ccccttttggt caccagttct agggcagtga tcagtacaac tattccaatt    7800
ctgactcttt ctcctggtga accagagacc acaccttcaa tggccaccag tcatggggaa    7860
gaagccagtt ctgctattcc aactccaact gtttcacctg ggtaccagg agtggtgacc    7920 tctctggtca ctagttctag ggcagtgact agtacaacta ttccaattct gacttttct    7980 cttggtgaac cagagaccac accttcaatg ccaccagtc atgggacaga agctggctca    8040
gctgttccaa ctgttttacc tgaggtacca ggaatggtga cctctctggt tgctagttct    8100
agggcagtaa ccagtacaac tcttccaact ctgactcttt ctcctggtga accagagacc    8160 acccttcaa tggccaccag tcatggggca gaagccagct caactgttcc aactgtttca    8220
cctgaggtac caggagtggt gacctctctg tcactagtt ctagtggagt aaacagtaca    8280
agtattccaa ctctgattct ttctcctggt gaactagaaa ccacaccttc aatggccacc    8340
agtcatgggg cagaagccag ctcagctgtt ccaactccaa ctgtttcacc tggggtatca    8400
ggagtggtga cccctctggt cactagttcc agggcagtga ccagtacaac tattccaatt    8460
ctaactcttt cttctagtga gccagagacc acaccttcaa tggccaccag tcatgggta    8520 gaagccagct cagctgttct aactgtttca cctgaggtac caggaatggt gacctttctg    8580
gtcactagtt ctagagcagt aaccagtaca actattccaa ctctgactat ttcttctgat    8640
gaaccagaga ccacaacttc attggtcacc cattctgagg caaagatgat ttcagccatt    8700
ccaactttag gtgtctcccc tactgtacaa gggctggtga cttcactggt cactagttct    8760
gggtcagaga ccagtgcgtt ttcaaatcta actgttgcct caagtcaacc agagaccata    8820
gactcatggg tcgctcatcc tgggacagaa gcaagttctg ttgttccaac tttgactgtc    8880
tccactggtg agccgtttac aaatatctca ttggtcaccc atcctgcaga gagtagctca    8940
actcttccca ggacaacctc aaggttttcc cacagtgaat tagacactat gccttctaca    9000
gtcaccagtc ctgaggcaga atccagctca gccatttcaa caactatttc acctggtata    9060
ccaggtgtgc tgacatcact ggtcactagc tctgggagag acatcagtgc aacttttcca    9120
acagtgcctg agtccccaca tgaatcagag gcaacagcct catgggttac tcatcctgca    9180
gtcaccagca aaacagttcc caggacaacc cctaattatt ctcatagtga accagacacc    9240
acaccatcaa tagccaccag tcctgggcca gaagccactt cagattttcc aacaataact    9300
gtctcacctg atgtaccaga tatggtaacc tcacaggtca ctagttctgg gacagacacc    9360
```

```
agtataacta ttccaactct gactctttct tctggtgagc cagagaccac aacctcattt   9420
atcacctatt ctgagacaca tacaagttca gccattccaa ctctccctgt ctcccctgat   9480
gcatcaaaga tgctgacctc actggtcatc agttctggga cagacagcac tacaactttc   9540
ccaacactga cggagacccc atatgaacca gagacaacag ccatacagct cattcatcct   9600
gcagagacca acacaatggt tcccaggaca actcccaagt tttcccatag taagtcagac   9660
accacactcc cagtagccat caccagtcct gggccagaag ccagttcagc tgtttcaacg   9720
acaactatct cacctgatat gtcagatctg gtgacctcac tggtccctag ttctgggaca   9780
gacaccagta caaccttccc aacattgagt gagacccccat atgaaccaga gactacagcc   9840
acgtggctca ctcatcctgc agaaaccagc acaacggttt ctgggacaat tcccaacttt   9900
tcccataggg gatcagacac tgcaccctca atggtcacca gtcctggagt agacacgagg   9960
tcaggtgttc caactacaac catcccaccc agtataccag gggtagtgac ctcacaggtc  10020
actagttctg caacagacac tagtacagct attccaactt tgactccttc tcctggtgaa  10080
ccagagacca cagcctcatc agctacccat cctgggacac agactggctt cactgttcca  10140
attcggactt tccctctag tgagccagat acaatggctt cctgggtcac tcatcctcca  10200
cagaccagca cacctgtttc cagaacaacc tccagttttt cccatagtag tccagatgcc  10260
acacctgtaa tggccaccag tcctaggaca gaagccagtt cagctgtact gacaacaatc  10320
tcacctggtg caccagagat ggtgacttca cagatcacta gttctggggc agcaaccagt  10380
acaactgttc caactttgac tcattctcct ggtatgccag agaccacagc cttattgagc  10440
acccatccca gaacagagac aagtaaaaca tttcctgctt caactgtgtt tcctcaagta  10500
tcagagacca cagcctcact caccattaga cctggtgcag agactagcac agctctccca  10560
actcagacaa catcctctct cttcacccta cttgtaactg gaaccagcag agttgatcta  10620
agtccaactg cttcacctgg tgtttctgca aaaacagccc cactttccac ccatccaggg  10680
acagaaacca gcacaatgat tccaacttca actctttccc ttggtttact agagactaca  10740
ggcttactgg ccaccagctc ttcagcagag accagcacga gtactctaac tctgactgtt  10800
tcccctgctg tctctgggct ttccagtgcc tctataacaa ctgataagcc ccaaactgtg  10860
acctcctgga acacagaaac ctcaccatct gtaacttcag ttggaccccc agaattttcc  10920
aggactgtca caggcaccac tatgaccttg ataccatcag agatgccaac accacctaaa  10980
accagtcatg gagaaggagt gagtccaacc actatcttga gaactacaat ggttgaagcc  11040
actaatttag ctaccacagg ttccagtccc actgtggcca agacaacaac caccttcaat  11100
acactggctg gaagcctctt tactcctctg accacacctg ggatgtccac cttggcctct  11160
gagagtgtga cctcaagaac aagttataac catcggtcct ggatctccac caccagcagt  11220
tataaccgtc ggtactggac ccctgccacc agcactccag tgacttctac attctcccca  11280
gggatttcca catcctccat ccccagctcc acagcagcca cagtcccatt catggtgcca  11340 ttcacccctca acttcaccat caccaacctg cagtacgagg aggacatgcg gcaccctggt  11400
tcaaggaagt tcaacgccac agagagagaa ctgcagggtc tgctcaaacc cttgttcagg  11460
aatagcagtc tggaataacct ctattcaggc tgcagactag cctcactcag gccagagaag  11520
gatagctcag ccacggcagt ggatgccatc tgcacacatc gccctgaccc tgaagacctc  11580
ggactggaca gagagcgact gtactgggag ctgagcaatc tgacaaatgg catccaggag  11640
ctgggccctt acaccctgga ccggaacagt ctctatgtca atggtttcac ccatcgaagc  11700
tctatgccca ccaccagcac tcctgggacc tccacagtgg atgtgggaac ctcagggact  11760
```

```
ccatcctcca gccccagccc cacgactgct ggccctctcc tgatgccgtt caccctcaac    11820
ttcaccatca ccaacctgca gtacgaggag gacatgcgtc gcactggctc caggaagttc    11880
aacaccatgg agagtgtcct gcagggtctg ctcaagccat tgttcaagaa caccagtgtt    11940
ggccctttgt actctggctg cagattgacc ttgctcaggc ccgagaaaga tggggcagcc    12000
actggagtgg atgccatctg cacccaccgc ctttgacccca aaagccctgg actcaacagg    12060
gagcagctgt actgggagct aagcaaactg accaatgaca ttgaagagct gggcccctac    12120
accctggaca ggaacagtct ctatgtcaat ggtttcaccc atcagagctc tgtgtccacc    12180
accagcactc ctgggacctc cacagtggat ctcagaacct cagggactcc atcctccctc    12240
tccagcccca caattatggc tgctggccct ctcctggtac cattcaccct caacttcacc    12300
atcaccaacc tgcagtatgg ggaggacatg ggtcaccctg gctccaggaa gttcaacacc    12360
acagagaggg tcctgcaggg tctgcttggt cccatattca agaacaccag tgttggccct    12420
ctgtactctg gctgcagact gacctctctc aggtccgaga aggatggagc agccactgga    12480
gtggatgcca tctgcatcca tcatcttgac cccaaaagcc ctggactcaa cagagagcgg    12540
ctgtactggg agctgagcca actgaccaat ggcatcaaag agctgggccc ctacaccctg    12600
gacaggaaca gtctctatgt caatggtttc acccatcgga cctctgtgcc caccaccagc    12660
actcctggga cctccacagt ggaccttgga acctcaggga ctccattctc cctcccaagc    12720
cccgcaactg ctggccctct cctggtgctg ttcaccctca acttcaccat caccaacctg    12780
aagtatgagg aggacatgca tcgccctggc tccaggaagt tcaacaccac tgagagggtc    12840
ctgcagaccc tggttggtcc tatgttcaag aacaccagtg ttggccttct gtactctggc    12900
tgcagactga ccttgctcag gtccgagaag gatggagcag ccactggagt ggatgccatc    12960
tgcacccacc gtcttgaccc caaaagccct ggagtggaca gggagcagct atactgggag    13020
ctgagccaac tgaccaatgg catcaaagag ctgggcccct acaccctgga caggaacagt    13080
ctctatgtca atggtttcac ccattggatc cctgtgccca ccagcagcac ccctgggacc    13140
tccacagtgg accttgggtc agggactcca tcctccctcc ccagccccac aagtgctgct    13200
ggccctctcc tggtgccatt caccctcaac ttcaccatca ccaacctgca gtacgaggag    13260
gacatgcatc acccaggctc caggaagttc aacaccacgg agcgggtcct gcagggtctg    13320
cttggtccta tgttcaagaa caccagtgtt ggccttctgt actctggctg cagactgacc    13380
ttgctcaggt ccgagaagga tggagcagca ctggagtgga tgccatctg cacccaccgt    13440 cttgacccca aaagccctgg agtggacagg gagcagctat actgggagct gagccagctg    13500
accaatggca tcaaagagct gggcccctac accctggaca ggaacagtct ctatgtcaat    13560
ggtttcaccc attggatccc tgtgcccacc agcagcactc ctgggacctc cacagtggac    13620
cttgggtcag ggactccatc ctccctcccc agccccacaa ctgctggccc tcctggtgtg    13680
ccgttcaccc tcaacttcac catcaccaac ctgaagtacg aggaggacat gcattgccct    13740
ggctccagga agttcaacac cacagagaga gtcctgcaga gtctgcttgg tcccatgttc    13800
aagaacacca gtgttggccc tctgtactct ggctgcagac tgaccttgct caggtccgag    13860
aaggatggag cagccactgg agtggatgcc atctgcaccc accgtcttga ccccaaaagc    13920
cctggagtgg acagggagca gctatactgg gagctgagcc agctgaccaa tggcatcaaa    13980
gagctgggtc cctacaccct ggacagaaac agtctctatg tcaatggttt cacccatcag    14040
acctctgcgc caacaccag cactcctggg acctccacag tggaccttgg gacctcaggg    14100
actccatcct ccctccccag ccctacatct gctggccctc tcctggtgcc attcaccctc    14160
```

-continued

```
aacttcacca tcaccaacct gcagtacgag gaggacatgc atcacccagg ctccaggaag    14220
ttcaacacca cggagcgggt cctgcagggt ctgcttggtc ccatgttcaa gaacaccagt    14280
gtcggccttc tgtactctgg ctgcagactg accttgctca ggcctgagaa gaatggggca    14340
gccactggaa tggatgccat ctgcagccac cgtcttgacc ccaaaagccc tggactcaac    14400
agagagcagc tgtactggga gctgagccag ctgacccatg gcatcaaaga gctgggcccc    14460
tacaccctgg acaggaacag tctctatgtc aatggtttca cccatcggag ctctgtggcc    14520
cccaccagca ctcctgggac ctccacagtg gaccttggga cctcaggggac tccatcctcc    14580 ctccccagcc ccacaacagc tgttcctctc ctggtgccgt tcaccctcaa ctttaccatc    14640
accaatctgc agtatgggga ggacatgcgt caccctggct ccaggaagtt caacaccaca    14700
gagagggtcc tgcagggtct gcttggtccc ttgttcaaga actccagtgt cggccctctg    14760
tactctggct gcagactgat ctctctcagg tctgagaagg atggggcagc cactggagtg    14820
gatgccatct gcacccacca ccttaaccct caaagccctg actggacag ggagcagctg    14880 tactggcagc tgagccagat gaccaatggc atcaaagagc tgggccccta caccctggac    14940
cggaacagtc tctacgtcaa tggtttcacc catcggagct ctgggctcac caccagcact    15000
ccttggactt ccacagttga ccttggaacc tcagggactc catccccgt ccccagcccc    15060 acaactgctg gccctctcct ggtgccattc accctaaact tcaccatcac caacctgcag    15120
tatgaggagg acatgcatcg ccctggatct aggaagttca cgccacaga gagggtcctg    15180 cagggtctgc ttagtcccat attcaagaac tccagtgttg ccctctgta ctctggctgc    15240 agactgacct ctctcaggcc cgagaaggat ggggcagcaa ctggaatgga tgctgtctgc    15300
ctctaccacc ctaatcccaa aagacctggg ctggacagag agcagctgta ctggagcta    15360 agccagctga cccacaacat cactgagctg gcccctaca gcctggacag gacagtctc    15420 tatgtcaatg gtttcaccca tcagaactct gtgcccacca ccagtactcc tgggacctcc    15480
acagtgtact gggcaaccac tgggactcca tcctccttcc ccggccacac agagcctggc    15540
cctctcctga taccattcac tttcaacttt accatcacca acctgcatta tgaggaaaac    15600
atgcaacacc ctggttccag gaagttcaac accacggaga gggttctgca gggtctgctc    15660
aagcccttgt tcaagaacac cagtgttggc cctctgtact ctggctgcag actgaccttg    15720
ctcagacctg agaagcagga ggcagccact ggagtggaca ccatctgtac ccaccgcgtt    15780
gatcccatcg gacctggact ggacagagag cggctatact gggagctgag ccagctgacc    15840
aacagcatca cagagctggg accctacacc ctggataggg acagtctcta tgtcaatggc    15900 ttcaacccctt ggagctctgt gccaaccacc agcactcctg ggacctccac agtgcacctg    15960
gcaacctctg ggactccatc ctccctgcct ggccacacag cccctgtccc tctcttgata    16020
ccattcaccc tcaactttac catcaccaac ctgcattatg aagaaaacat gcaacaccct    16080
ggttccagga agttcaacac cacggagagg gttctgcagg gtctgctcaa gcccttgttc    16140
aagagcacca gcgttggccc tctgtactct ggctgcagac tgaccttgct cagacctgag    16200
aaacatgggg cagccactgg agtggacgcc atctgcaccc tccgccttga tcccactggt    16260
cctggactgg acagagagcg gctatactgg gagctgagcc agctgaccaa cagcgttaca    16320
gagctgggcc cctacacccct ggacagggac agtctctatg tcaatggctt cacccatcgg    16380
agctctgtgc caaccaccag tattcctggg acctctgcag tgcacctgga aacctctggg    16440
actccagcct ccctccctgg ccacacagcc cctggccctc tcctggtgcc attcacccte    16500 aacttcacta tcaccaacct gcagtatgag gaggacatgc gtcaccctgg ttccaggaag    16560
```

```
ttcaacacca cggagagagt cctgcagggt ctgctcaagc ccttgttcaa gagcaccagt    16620
gttggccctc tgtactctgg ctgcagactg accttgctca ggcctgaaaa acgtggggca    16680
gccaccggcg tggacaccat ctgcactcac cgccttgacc ctctaaaccc tggactggac    16740
agagagcagc tatactggga gctgagcaaa ctgacccgtg catcatcga gctgggcccc     16800 tacctcctgg acagaggcag tctctatgtc aatggtttca cccatcggaa ctttgtgccc    16860
atcaccagca ctcctgggac ctccacagta cacctaggaa cctctgaaac tccatcctcc    16920
ctacctagac ccatagtgcc tggccctctc ctggtgccat tcaccctcaa cttcaccatc    16980
accaacttgc agtatgagga ggccatgcga caccctggct ccaggaagtt caataccacg    17040
gagagggtcc tacagggtct gctcaggccc ttgttcaaga ataccagtat cggccctctg    17100
tactccagct gcagactgac cttgctcagg ccagagaagg acaaggcagc caccagagtg    17160
gatgccatct gtacccacca ccctgaccct caaagccctg gactgaacag agagcagctg    17220
tactgggagc tgagccagct gacccacggc atcactgagc tgggccccta cccctggac     17280 agggacagtc tctatgtcga tggtttcact cattggagcc ccataccaac caccagcact    17340
cctgggacct ccatagtgaa cctgggaacc tctgggatcc caccttccct ccctgaaact    17400
acagccaccg gccctctcct ggtgccattc acactcaact tcaccatcac taacctacag    17460
tatgaggaga acatgggtca ccctggctcc aggaagttca acatcacgga gagtgttctg    17520
cagggtctgc tcaagccctt gttcaagagc accagtgttg ccctctgta ttctggctgc      17580 agactgacct tgctcaggcc tgagaaggac ggagtagcca ccagagtgga cgccatctgc    17640
acccaccgcc ctgaccccaa atccctgggg ctagacagac agcagctata ctgggagctg    17700
agccagctga cccacagcat cactgagctg gaccctaca ccctggatag ggacagtctc      17760
tatgtcaatg gtttcaccca gcggagctct gtgcccacca ccagcagtga gtattctact    17820
gatgttccca tggccccaat cttacaacaa acttagcagg agctgacccc tattcataag    17880
cccttatgtc ctttccataa gggaaggaac atagaggaca caaattattc cccttcccca    17940
ctgccccagc taatcagagt cccagctgaa gccccacagg caaaaatccc catgaatagt    18000
ccctcctgct ggcattacnt tccatgagag cacnttgctc ctttcactgt tgagggcttc    18060
tcctcagctc ctgggacttt cacagtacag ccggaaacct ctgagactcc atcatccctc    18120
cctggcccca caggtaaata ccagtcaatg gtatttggag catggttgat gagtgtaaac    18180
atctctgttt atactctgtt agagcatggt tgatgagtgt aaacatctct gtcattattc      18240
actcaactaa agatggaaat tcatagtaaa tgtagtaacc ataggtcaac caacccagtt    18300
cattgagcac tgcctctgta tcaggacctg gatatacatc agggaacaaa aaaaaaaaa     18360 aaaa                                                                   18364
```

<210> SEQ ID NO 8
<211> LENGTH: 5935
<212> TYPE: PRT
<213> ORGANISM: Homo sapiens
<220> FEATURE:
<221> NAME/KEY: MISC_FEATURE
<222> LOCATION: (1)..(5935)
<223> OTHER INFORMATION: Amino acid sequence of MUC16B

<400> SEQUENCE: 8

Met Gly Ile Ser Arg Glu Pro Gly Thr Ser Thr Ser Asn Leu Ser
1               5                   10                  15

Ser Thr Ser His Glu Arg Leu Thr Thr Leu Glu Asp Thr Val Asp Thr
            20                  25                  30

```
Glu Ala Met Gln Pro Ser Thr His Thr Ala Val Thr Asn Val Arg Thr
            35                  40                  45

Ser Ile Ser Gly His Glu Ser Gln Ser Ser Val Leu Ser Asp Ser Glu
        50                  55                  60

Thr Pro Lys Ala Thr Ser Pro Met Gly Thr Thr Tyr Thr Met Gly Glu
 65                  70                  75                  80

Thr Ser Val Ser Ile Ser Thr Ser Asp Phe Phe Glu Thr Ser Arg Ile
                85                  90                  95

Gln Ile Glu Pro Thr Ser Ser Leu Thr Ser Gly Leu Arg Glu Thr Ser
            100                 105                 110

Ser Ser Glu Arg Ile Ser Ser Ala Thr Glu Gly Ser Thr Val Leu Ser
            115                 120                 125

Glu Val Pro Ser Gly Ala Thr Glu Val Ser Arg Thr Glu Val Ile
            130                 135                 140

Ser Ser Arg Gly Thr Ser Met Ser Gly Pro Asp Gln Phe Thr Ile Ser
145                 150                 155                 160

Pro Asp Ile Ser Thr Glu Ala Ile Thr Arg Leu Ser Thr Ser Pro Ile
                165                 170                 175

Met Thr Glu Ser Ala Glu Ser Ala Ile Thr Ile Glu Thr Gly Ser Pro
            180                 185                 190

Gly Ala Thr Ser Glu Gly Thr Leu Thr Leu Asp Thr Ser Thr Thr Thr
            195                 200                 205

Phe Trp Ser Gly Thr His Ser Thr Ala Ser Pro Gly Phe Ser His Ser
            210                 215                 220

Glu Met Thr Thr Leu Met Ser Arg Thr Pro Gly Asp Val Pro Trp Pro
225                 230                 235                 240

Ser Leu Pro Ser Val Glu Glu Ala Ser Ser Val Ser Ser Ser Leu Ser
                245                 250                 255

Ser Pro Ala Met Thr Ser Thr Ser Phe Phe Ser Thr Leu Pro Glu Ser
            260                 265                 270

Ile Ser Ser Ser Pro His Pro Val Thr Ala Leu Leu Thr Leu Gly Pro
            275                 280                 285

Val Lys Thr Thr Asp Met Leu Arg Thr Ser Ser Glu Pro Glu Thr Ser
            290                 295                 300

Ser Pro Pro Asn Leu Ser Ser Thr Ser Ala Glu Ile Leu Ala Thr Ser
305                 310                 315                 320

Glu Val Thr Lys Asp Arg Glu Lys Ile His Pro Ser Ser Asn Thr Pro
            325                 330                 335

Val Val Asn Val Gly Thr Val Ile Tyr Lys His Leu Ser Pro Ser Ser
            340                 345                 350

Val Leu Ala Asp Leu Val Thr Thr Lys Pro Thr Ser Pro Met Ala Thr
            355                 360                 365

Thr Ser Thr Leu Gly Asn Thr Ser Val Ser Thr Ser Thr Pro Ala Phe
            370                 375                 380

Pro Glu Thr Met Met Thr Gln Pro Thr Ser Ser Leu Thr Ser Gly Leu
385                 390                 395                 400

Arg Glu Ile Ser Thr Ser Gln Glu Thr Ser Ser Ala Thr Glu Arg Ser
            405                 410                 415

Ala Ser Leu Ser Gly Met Pro Thr Gly Ala Thr Thr Lys Val Ser Arg
            420                 425                 430

Thr Glu Ala Leu Ser Leu Gly Arg Thr Ser Thr Pro Gly Pro Ala Gln
            435                 440                 445
```

```
Ser Thr Ile Ser Pro Glu Ile Ser Thr Glu Thr Ile Thr Arg Ile Ser
    450                 455                 460

Thr Pro Leu Thr Thr Thr Gly Ser Ala Glu Met Thr Ile Thr Pro Lys
465                 470                 475                 480

Thr Gly His Ser Gly Ala Ser Ser Gln Gly Thr Phe Thr Leu Asp Thr
                485                 490                 495

Ser Ser Arg Ala Ser Trp Pro Gly Thr His Ser Ala Ala Thr His Arg
            500                 505                 510

Ser Pro His Ser Gly Met Thr Thr Pro Met Ser Arg Gly Pro Glu Asp
        515                 520                 525

Val Ser Trp Pro Ser Arg Pro Ser Val Glu Lys Thr Ser Pro Pro Ser
    530                 535                 540

Ser Leu Val Ser Leu Ser Ala Val Thr Ser Pro Ser Pro Leu Tyr Ser
545                 550                 555                 560

Thr Pro Ser Glu Ser Ser His Ser Ser Pro Leu Arg Val Thr Ser Leu
                565                 570                 575

Phe Thr Pro Val Met Met Lys Thr Thr Asp Met Leu Asp Thr Ser Leu
            580                 585                 590

Glu Pro Val Thr Thr Ser Pro Pro Ser Met Asn Ile Thr Ser Asp Glu
        595                 600                 605

Ser Leu Ala Thr Ser Lys Ala Thr Met Glu Thr Glu Ala Ile Gln Leu
    610                 615                 620

Ser Glu Asn Thr Ala Val Thr Gln Met Gly Thr Ile Ser Ala Arg Gln
625                 630                 635                 640

Glu Phe Tyr Ser Ser Tyr Pro Gly Leu Pro Glu Pro Ser Lys Val Thr
                645                 650                 655

Ser Pro Val Val Thr Ser Ser Thr Ile Lys Asp Ile Val Ser Thr Thr
            660                 665                 670

Ile Pro Ala Ser Ser Glu Ile Thr Arg Ile Glu Met Glu Ser Thr Ser
        675                 680                 685

Thr Leu Thr Pro Thr Pro Arg Glu Thr Ser Thr Ser Gln Glu Ile His
    690                 695                 700

Ser Ala Thr Lys Pro Ser Thr Val Pro Tyr Lys Ala Leu Thr Ser Ala
705                 710                 715                 720

Thr Ile Glu Asp Ser Met Thr Gln Val Met Ser Ser Arg Gly Pro
                725                 730                 735

Ser Pro Asp Gln Ser Thr Met Ser Gln Asp Ile Ser Thr Glu Val Ile
            740                 745                 750

Thr Arg Leu Ser Thr Ser Pro Ile Lys Thr Glu Ser Thr Glu Met Thr
        755                 760                 765

Ile Thr Thr Gln Thr Gly Ser Pro Gly Ala Thr Ser Arg Gly Thr Leu
    770                 775                 780

Thr Leu Asp Thr Ser Thr Thr Phe Met Ser Gly Thr His Ser Thr Ala
785                 790                 795                 800

Ser Gln Gly Phe Ser His Ser Gln Met Thr Ala Leu Met Ser Arg Thr
                805                 810                 815

Pro Gly Glu Val Pro Trp Leu Ser His Pro Ser Val Glu Glu Ala Ser
            820                 825                 830

Ser Ala Ser Phe Ser Leu Ser Ser Pro Val Met Thr Ser Ser Ser Pro
        835                 840                 845

Val Ser Ser Thr Leu Pro Asp Ser Ile His Ser Ser Ser Leu Pro Val
    850                 855                 860
```

-continued

```
Thr Ser Leu Leu Thr Ser Gly Leu Val Lys Thr Thr Glu Leu Leu Gly
865                 870                 875                 880

Thr Ser Ser Glu Pro Glu Thr Ser Ser Pro Pro Asn Leu Ser Ser Thr
                885                 890                 895

Ser Ala Glu Ile Leu Ala Thr Thr Glu Val Thr Thr Asp Thr Glu Lys
            900                 905                 910

Leu Glu Met Thr Asn Val Val Thr Ser Gly Tyr Thr His Glu Ser Pro
        915                 920                 925

Ser Ser Val Leu Ala Asp Ser Val Thr Thr Lys Ala Thr Ser Ser Met
    930                 935                 940

Gly Ile Thr Tyr Pro Thr Gly Asp Thr Asn Val Leu Thr Ser Thr Pro
945                 950                 955                 960

Ala Phe Ser Asp Thr Ser Arg Ile Gln Thr Lys Ser Lys Leu Ser Leu
                965                 970                 975

Thr Pro Gly Leu Met Glu Thr Ser Ile Ser Glu Glu Thr Ser Ser Ala
            980                 985                 990

Thr Glu Lys Ser Thr Val Leu Ser  Ser Val Pro Thr Gly  Ala Thr Thr
        995                 1000                1005

Glu Val  Ser Arg Thr Glu Ala  Ile Ser Ser Ser Arg  Thr Ser Ile
1010                1015                1020

Pro Gly  Pro Ala Gln Ser Thr  Met Ser Ser Asp Thr  Ser Met Glu
1025                1030                1035

Thr Ile  Thr Arg Ile Ser Thr  Pro Leu Thr Arg Lys  Glu Ser Thr
1040                1045                1050

Asp Met  Ala Ile Thr Pro Lys  Thr Gly Pro Ser Gly  Ala Thr Ser
1055                1060                1065

Gln Gly  Thr Phe Thr Leu Asp  Ser Ser Ser Thr Ala  Ser Trp Pro
1070                1075                1080

Gly Thr  His Ser Ala Thr Thr  Gln Arg Phe Pro Arg  Ser Val Val
1085                1090                1095

Thr Thr  Pro Met Ser Arg Gly  Pro Glu Asp Val Ser  Trp Pro Ser
1100                1105                1110

Pro Leu  Ser Val Glu Lys Asn  Ser Pro Pro Ser Ser  Leu Val Ser
1115                1120                1125

Ser Ser  Ser Val Thr Ser Pro  Ser Pro Leu Tyr Ser  Thr Pro Ser
1130                1135                1140

Gly Ser  Ser His Ser Ser Pro  Val Pro Val Thr Ser  Leu Phe Thr
1145                1150                1155

Ser Ile  Met Met Lys Ala Thr  Asp Met Leu Asp Ala  Ser Leu Glu
1160                1165                1170

Pro Glu  Thr Thr Ser Ala Pro  Asn Met Asn Ile Thr  Ser Asp Glu
1175                1180                1185

Ser Leu  Ala Ala Ser Lys Ala  Thr Thr Glu Thr Glu  Ala Ile His
1190                1195                1200

Val Phe  Glu Asn Thr Ala Ala  Ser His Val Glu Thr  Thr Ser Ala
1205                1210                1215

Thr Glu  Glu Leu Tyr Ser Ser  Ser Pro Gly Phe Ser  Glu Pro Thr
1220                1225                1230

Lys Val  Ile Ser Pro Val Val  Thr Ser Ser Ser Ile  Arg Asp Asn
1235                1240                1245

Met Val  Ser Thr Thr Met Pro  Gly Ser Ser Gly Ile  Thr Arg Ile
1250                1255                1260
```

-continued

```
Glu Ile Glu Ser Met Ser Ser Leu Thr Pro Gly Leu Arg Glu Thr
1265                1270                1275

Arg Thr Ser Gln Asp Ile Thr Ser Ser Thr Glu Thr Ser Thr Val
1280                1285                1290

Leu Tyr Lys Met Pro Ser Gly Ala Thr Pro Glu Val Ser Arg Thr
1295                1300                1305

Glu Val Met Pro Ser Ser Arg Thr Ser Ile Pro Gly Pro Ala Gln
1310                1315                1320

Ser Thr Met Ser Leu Asp Ile Ser Asp Glu Val Val Thr Arg Leu
1325                1330                1335

Ser Thr Ser Pro Ile Met Thr Glu Ser Ala Glu Ile Thr Ile Thr
1340                1345                1350

Thr Gln Thr Gly Tyr Ser Leu Ala Thr Ser Gln Val Thr Leu Pro
1355                1360                1365

Leu Gly Thr Ser Met Thr Phe Leu Ser Gly Thr His Ser Thr Met
1370                1375                1380

Ser Gln Gly Leu Ser His Ser Glu Met Thr Asn Leu Met Ser Arg
1385                1390                1395

Gly Pro Glu Ser Leu Ser Trp Thr Ser Pro Arg Phe Val Glu Thr
1400                1405                1410

Thr Arg Ser Ser Ser Ser Leu Thr Ser Leu Pro Leu Thr Thr Ser
1415                1420                1425

Leu Ser Pro Val Ser Ser Thr Leu Leu Asp Ser Ser Pro Ser Ser
1430                1435                1440

Pro Leu Pro Val Thr Ser Leu Ile Leu Pro Gly Leu Val Lys Thr
1445                1450                1455

Thr Glu Val Leu Asp Thr Ser Ser Glu Pro Lys Thr Ser Ser Ser
1460                1465                1470

Pro Asn Leu Ser Ser Thr Ser Val Glu Ile Pro Ala Thr Ser Glu
1475                1480                1485

Ile Met Thr Asp Thr Glu Lys Ile His Pro Ser Ser Asn Thr Ala
1490                1495                1500

Val Ala Lys Val Arg Thr Ser Ser Ser Val His Glu Ser His Ser
1505                1510                1515

Ser Val Leu Ala Asp Ser Glu Thr Thr Ile Thr Ile Pro Ser Met
1520                1525                1530

Gly Ile Thr Ser Ala Val Glu Asp Thr Thr Val Phe Thr Ser Asn
1535                1540                1545

Pro Ala Phe Ser Glu Thr Arg Arg Ile Pro Thr Glu Pro Thr Phe
1550                1555                1560

Ser Leu Thr Pro Gly Phe Arg Glu Thr Ser Thr Glu Glu Thr
1565                1570                1575

Thr Ser Ile Thr Glu Thr Ser Ala Val Leu Phe Gly Val Pro Thr
1580                1585                1590

Ser Ala Thr Thr Glu Val Ser Met Thr Glu Ile Met Ser Ser Asn
1595                1600                1605

Arg Thr His Ile Pro Asp Ser Asp Gln Ser Thr Met Ser Pro Asp
1610                1615                1620

Ile Ile Thr Glu Val Ile Thr Arg Leu Ser Ser Ser Ser Met Met
1625                1630                1635

Ser Glu Ser Thr Gln Met Thr Ile Thr Thr Gln Lys Ser Ser Pro
1640                1645                1650
```

```
Gly Ala Thr Ala Gln Ser Thr Leu Thr Leu Ala Thr Thr Thr Ala
1655                1660                1665

Pro Leu Ala Arg Thr His Ser Thr Val Pro Arg Phe Leu His
1670                1675                1680

Ser Glu Met Thr Thr Leu Met Ser Arg Ser Pro Glu Asn Pro Ser
1685                1690                1695

Trp Lys Ser Ser Pro Phe Val Glu Lys Thr Ser Ser Ser Ser Ser
1700                1705                1710

Leu Leu Ser Leu Pro Val Thr Thr Ser Pro Ser Val Ser Ser Thr
1715                1720                1725

Leu Pro Gln Ser Ile Pro Ser Ser Ser Phe Ser Val Thr Ser Leu
1730                1735                1740

Leu Thr Pro Gly Met Val Lys Thr Thr Asp Thr Ser Thr Glu Pro
1745                1750                1755

Gly Thr Ser Leu Ser Pro Asn Leu Ser Gly Thr Ser Val Glu Ile
1760                1765                1770

Leu Ala Ala Ser Glu Val Thr Thr Asp Thr Glu Lys Ile His Pro
1775                1780                1785

Ser Ser Ser Met Ala Val Thr Asn Val Gly Thr Thr Ser Ser Gly
1790                1795                1800

His Glu Leu Tyr Ser Ser Val Ser Ile His Ser Glu Pro Ser Lys
1805                1810                1815

Ala Thr Tyr Pro Val Gly Thr Pro Ser Ser Met Ala Glu Thr Ser
1820                1825                1830

Ile Ser Thr Ser Met Pro Ala Asn Phe Glu Thr Thr Gly Phe Glu
1835                1840                1845

Ala Glu Pro Phe Ser His Leu Thr Ser Gly Leu Arg Lys Thr Asn
1850                1855                1860

Met Ser Leu Asp Thr Ser Ser Val Thr Pro Thr Asn Thr Pro Ser
1865                1870                1875

Ser Pro Gly Ser Thr His Leu Leu Gln Ser Ser Lys Thr Asp Phe
1880                1885                1890

Thr Ser Ser Ala Lys Thr Ser Ser Pro Asp Trp Pro Pro Ala Ser
1895                1900                1905

Gln Tyr Thr Glu Ile Pro Val Asp Ile Ile Thr Pro Phe Asn Ala
1910                1915                1920

Ser Pro Ser Ile Thr Glu Ser Thr Gly Ile Thr Ser Phe Pro Glu
1925                1930                1935

Ser Arg Phe Thr Met Ser Val Thr Glu Ser Thr His His Leu Ser
1940                1945                1950

Thr Asp Leu Leu Pro Ser Ala Glu Thr Ile Ser Thr Gly Thr Val
1955                1960                1965

Met Pro Ser Leu Ser Glu Ala Met Thr Ser Phe Ala Thr Thr Gly
1970                1975                1980

Val Pro Arg Ala Ile Ser Gly Ser Gly Ser Pro Phe Ser Arg Thr
1985                1990                1995

Glu Ser Gly Pro Gly Asp Ala Thr Leu Ser Thr Ile Ala Glu Ser
2000                2005                2010

Leu Pro Ser Ser Thr Pro Val Pro Phe Ser Ser Ser Thr Phe Thr
2015                2020                2025

Thr Thr Asp Ser Ser Thr Ile Pro Ala Leu His Glu Ile Thr Ser
2030                2035                2040
```

```
Ser Ser Ala Thr Pro Tyr Arg Val Asp Thr Ser Leu Gly Thr Glu
2045                2050                2055

Ser Ser Thr Thr Glu Gly Arg Leu Val Met Val Ser Thr Leu Asp
2060                2065                2070

Thr Ser Ser Gln Pro Gly Arg Thr Ser Ser Pro Ile Leu Asp
2075                2080                2085

Thr Arg Met Thr Glu Ser Val Glu Leu Gly Thr Val Thr Ser Ala
2090                2095                2100

Tyr Gln Val Pro Ser Leu Ser Thr Arg Leu Thr Arg Asp Gly Ile
2105                2110                2115

Met Glu His Ile Thr Lys Ile Pro Asn Glu Ala Ala His Arg Gly
2120                2125                2130

Thr Ile Arg Pro Val Lys Gly Pro Gln Thr Ser Thr Ser Pro Ala
2135                2140                2145

Ser Pro Lys Gly Leu His Thr Gly Gly Thr Lys Arg Met Glu Thr
2150                2155                2160

Thr Thr Thr Ala Leu Lys Thr Thr Thr Ala Leu Lys Thr Thr
2165                2170                2175

Ser Arg Ala Thr Leu Thr Thr Ser Val Tyr Thr Pro Thr Leu Gly
2180                2185                2190

Thr Leu Thr Pro Leu Asn Ala Ser Met Gln Met Ala Ser Thr Ile
2195                2200                2205

Pro Thr Glu Met Met Ile Thr Thr Pro Tyr Val Phe Pro Asp Val
2210                2215                2220

Pro Glu Thr Thr Ser Ser Leu Ala Thr Ser Leu Gly Ala Glu Thr
2225                2230                2235

Ser Thr Ala Leu Pro Arg Thr Thr Pro Ser Val Phe Asn Arg Glu
2240                2245                2250

Ser Glu Thr Thr Ala Ser Leu Val Ser Arg Ser Gly Ala Glu Arg
2255                2260                2265

Ser Pro Val Ile Gln Thr Leu Asp Val Ser Ser Ser Glu Pro Asp
2270                2275                2280

Thr Thr Ala Ser Trp Val Ile His Pro Ala Glu Thr Ile Pro Thr
2285                2290                2295

Val Ser Lys Thr Thr Pro Asn Phe Phe His Ser Glu Leu Asp Thr
2300                2305                2310

Val Ser Ser Thr Ala Thr Ser His Gly Ala Asp Val Ser Ser Ala
2315                2320                2325

Ile Pro Thr Asn Ile Ser Pro Ser Glu Leu Asp Ala Leu Thr Pro
2330                2335                2340

Leu Val Thr Ile Ser Gly Thr Asp Thr Ser Thr Thr Phe Pro Thr
2345                2350                2355

Leu Thr Lys Ser Pro His Glu Thr Glu Thr Arg Thr Thr Trp Leu
2360                2365                2370

Thr His Pro Ala Glu Thr Ser Thr Ile Pro Arg Thr Ile Pro
2375                2380                2385

Asn Phe Ser His His Glu Ser Asp Ala Thr Pro Ser Ile Ala Thr
2390                2395                2400

Ser Pro Gly Ala Glu Thr Ser Ser Ala Ile Pro Ile Met Thr Val
2405                2410                2415

Ser Pro Gly Ala Glu Asp Leu Val Thr Ser Gln Val Thr Ser Ser
2420                2425                2430
```

-continued

```
Gly Thr Asp Arg Asn Met Thr Ile Pro Thr Leu Thr Leu Ser Pro
2435                2440            2445

Gly Glu Pro Lys Thr Ile Ala Ser Leu Val Thr His Pro Glu Ala
2450                2455            2460

Gln Thr Ser Ser Ala Ile Pro Thr Ser Thr Ile Ser Pro Ala Val
2465                2470            2475

Ser Arg Leu Val Thr Ser Met Val Thr Ser Leu Ala Ala Lys Thr
2480                2485            2490

Ser Thr Thr Asn Arg Ala Leu Thr Asn Ser Pro Gly Glu Pro Ala
2495                2500            2505

Thr Thr Val Ser Leu Val Thr His Ser Ala Gln Thr Ser Pro Thr
2510                2515            2520

Val Pro Trp Thr Thr Ser Ile Phe Phe His Ser Lys Ser Asp Thr
2525                2530            2535

Thr Pro Ser Met Thr Thr Ser His Gly Ala Glu Ser Ser Ser Ala
2540                2545            2550

Val Pro Thr Pro Thr Val Ser Thr Glu Val Pro Gly Val Val Thr
2555                2560            2565

Pro Leu Val Thr Ser Ser Arg Ala Val Ile Ser Thr Thr Ile Pro
2570                2575            2580

Ile Leu Thr Leu Ser Pro Gly Glu Pro Glu Thr Thr Pro Ser Met
2585                2590            2595

Ala Thr Ser His Gly Glu Glu Ala Ser Ser Ala Ile Pro Thr Pro
2600                2605            2610

Thr Val Ser Pro Gly Val Pro Gly Val Val Thr Ser Leu Val Thr
2615                2620            2625

Ser Ser Arg Ala Val Thr Ser Thr Thr Ile Pro Ile Leu Thr Phe
2630                2635            2640

Ser Leu Gly Glu Pro Glu Thr Thr Pro Ser Met Ala Thr Ser His
2645                2650            2655

Gly Thr Glu Ala Gly Ser Ala Val Pro Thr Val Leu Pro Glu Val
2660                2665            2670

Pro Gly Met Val Thr Ser Leu Val Ala Ser Ser Arg Ala Val Thr
2675                2680            2685

Ser Thr Thr Leu Pro Thr Leu Thr Leu Ser Pro Gly Glu Pro Glu
2690                2695            2700

Thr Thr Pro Ser Met Ala Thr Ser His Gly Ala Glu Ala Ser Ser
2705                2710            2715

Thr Val Pro Thr Val Ser Pro Glu Val Pro Gly Val Val Thr Ser
2720                2725            2730

Leu Val Thr Ser Ser Ser Gly Val Asn Ser Thr Ser Ile Pro Thr
2735                2740            2745

Leu Ile Leu Ser Pro Gly Glu Leu Glu Thr Thr Pro Ser Met Ala
2750                2755            2760

Thr Ser His Gly Ala Glu Ala Ser Ser Ala Val Pro Thr Pro Thr
2765                2770            2775

Val Ser Pro Gly Val Ser Gly Val Val Thr Pro Leu Val Thr Ser
2780                2785            2790

Ser Arg Ala Val Thr Ser Thr Ile Pro Ile Leu Thr Leu Ser
2795                2800            2805

Ser Ser Glu Pro Glu Thr Thr Pro Ser Met Ala Thr Ser His Gly
2810                2815            2820
```

-continued

| | | | | | | | | | | |
|---|---|---|---|---|---|---|---|---|---|---|
| Val | Glu | Ala | Ser | Ser | Ala | Val | Leu | Thr | Val | Ser | Pro | Glu | Val | Pro |
| 2825 | | | | 2830 | | | | | 2835 | | | | |

Val Glu Ala Ser Ser Ala Val Leu Thr Val Ser Pro Glu Val Pro
    2825                2830                2835

Gly Met Val Thr Phe Leu Val Thr Ser Ser Arg Ala Val Thr Ser
    2840                2845                2850

Thr Thr Ile Pro Thr Leu Thr Ile Ser Ser Asp Glu Pro Glu Thr
    2855                2860                2865

Thr Thr Ser Leu Val Thr His Ser Glu Ala Lys Met Ile Ser Ala
    2870                2875                2880

Ile Pro Thr Leu Gly Val Ser Pro Thr Val Gln Gly Leu Val Thr
    2885                2890                2895

Ser Leu Val Thr Ser Ser Gly Ser Glu Thr Ser Ala Phe Ser Asn
    2900                2905                2910

Leu Thr Val Ala Ser Ser Gln Pro Glu Thr Ile Asp Ser Trp Val
    2915                2920                2925

Ala His Pro Gly Thr Glu Ala Ser Ser Val Val Pro Thr Leu Thr
    2930                2935                2940

Val Ser Thr Gly Glu Pro Phe Thr Asn Ile Ser Leu Val Thr His
    2945                2950                2955

Pro Ala Glu Ser Ser Ser Thr Leu Pro Arg Thr Thr Ser Arg Phe
    2960                2965                2970

Ser His Ser Glu Leu Asp Thr Met Pro Ser Thr Val Thr Ser Pro
    2975                2980                2985

Glu Ala Glu Ser Ser Ser Ala Ile Ser Thr Thr Ile Ser Pro Gly
    2990                2995                3000

Ile Pro Gly Val Leu Thr Ser Leu Val Thr Ser Ser Gly Arg Asp
    3005                3010                3015

Ile Ser Ala Thr Phe Pro Thr Val Pro Glu Ser Pro His Glu Ser
    3020                3025                3030

Glu Ala Thr Ala Ser Trp Val Thr His Pro Ala Val Thr Ser Thr
    3035                3040                3045

Thr Val Pro Arg Thr Thr Pro Asn Tyr Ser His Ser Glu Pro Asp
    3050                3055                3060

Thr Thr Pro Ser Ile Ala Thr Ser Pro Gly Ala Glu Ala Thr Ser
    3065                3070                3075

Asp Phe Pro Thr Ile Thr Val Ser Pro Asp Val Pro Asp Met Val
    3080                3085                3090

Thr Ser Gln Val Thr Ser Ser Gly Thr Asp Thr Ser Ile Thr Ile
    3095                3100                3105

Pro Thr Leu Thr Leu Ser Ser Gly Glu Pro Glu Thr Thr Thr Ser
    3110                3115                3120

Phe Ile Thr Tyr Ser Glu Thr His Thr Ser Ser Ala Ile Pro Thr
    3125                3130                3135

Leu Pro Val Ser Pro Asp Ala Ser Lys Met Leu Thr Ser Leu Val
    3140                3145                3150

Ile Ser Ser Gly Thr Asp Ser Thr Thr Thr Phe Pro Thr Leu Thr
    3155                3160                3165

Glu Thr Pro Tyr Glu Pro Glu Thr Thr Ala Ile Gln Leu Ile His
    3170                3175                3180

Pro Ala Glu Thr Asn Thr Met Val Pro Arg Thr Thr Pro Lys Phe
    3185                3190                3195

Ser His Ser Lys Ser Asp Thr Thr Leu Pro Val Ala Ile Thr Ser
    3200                3205                3210

-continued

```
Pro Gly Pro Glu Ala Ser Ser Ala Val Ser Thr Thr Thr Ile Ser
3215             3220                 3225

Pro Asp Met Ser Asp Leu Val Thr Ser Leu Val Pro Ser Ser Gly
3230             3235                 3240

Thr Asp Thr Ser Thr Thr Phe Pro Thr Leu Ser Glu Thr Pro Tyr
3245             3250                 3255

Glu Pro Glu Thr Thr Ala Thr Trp Leu Thr His Pro Ala Glu Thr
3260             3265                 3270

Ser Thr Thr Val Ser Gly Thr Ile Pro Asn Phe Ser His Arg Gly
3275             3280                 3285

Ser Asp Thr Ala Pro Ser Met Val Thr Ser Pro Gly Val Asp Thr
3290             3295                 3300

Arg Ser Gly Val Pro Thr Thr Thr Ile Pro Pro Ser Ile Pro Gly
3305             3310                 3315

Val Val Thr Ser Gln Val Thr Ser Ser Ala Thr Asp Thr Ser Thr
3320             3325                 3330

Ala Ile Pro Thr Leu Thr Pro Ser Pro Gly Glu Pro Glu Thr Thr
3335             3340                 3345

Ala Ser Ser Ala Thr His Pro Gly Thr Gln Thr Gly Phe Thr Val
3350             3355                 3360

Pro Ile Arg Thr Val Pro Ser Ser Glu Pro Asp Thr Met Ala Ser
3365             3370                 3375

Trp Val Thr His Pro Pro Gln Thr Ser Thr Pro Val Ser Arg Thr
3380             3385                 3390

Thr Ser Ser Phe Ser His Ser Ser Pro Asp Ala Thr Pro Val Met
3395             3400                 3405

Ala Thr Ser Pro Arg Thr Glu Ala Ser Ser Ala Val Leu Thr Thr
3410             3415                 3420

Ile Ser Pro Gly Ala Pro Glu Met Val Thr Ser Gln Ile Thr Ser
3425             3430                 3435

Ser Gly Ala Ala Thr Ser Thr Thr Val Pro Thr Leu Thr His Ser
3440             3445                 3450

Pro Gly Met Pro Glu Thr Thr Ala Leu Leu Ser Thr His Pro Arg
3455             3460                 3465

Thr Glu Thr Ser Lys Thr Phe Pro Ala Ser Thr Val Phe Pro Gln
3470             3475                 3480

Val Ser Glu Thr Thr Ala Ser Leu Thr Ile Arg Pro Gly Ala Glu
3485             3490                 3495

Thr Ser Thr Ala Leu Pro Thr Gln Thr Thr Ser Ser Leu Phe Thr
3500             3505                 3510

Leu Leu Val Thr Gly Thr Ser Arg Val Asp Leu Ser Pro Thr Ala
3515             3520                 3525

Ser Pro Gly Val Ser Ala Lys Thr Ala Pro Leu Ser Thr His Pro
3530             3535                 3540

Gly Thr Glu Thr Ser Thr Met Ile Pro Thr Ser Thr Leu Ser Leu
3545             3550                 3555

Gly Leu Leu Glu Thr Thr Gly Leu Leu Ala Thr Ser Ser Ser Ala
3560             3565                 3570

Glu Thr Ser Thr Ser Thr Leu Thr Leu Thr Val Ser Pro Ala Val
3575             3580                 3585

Ser Gly Leu Ser Ser Ala Ser Ile Thr Thr Asp Lys Pro Gln Thr
3590             3595                 3600
```

-continued

| | | | | | | | | | |
|---|---|---|---|---|---|---|---|---|---|
| Val | Thr | Ser | Trp | Asn | Thr | Glu | Thr | Ser | Pro | Ser | Val | Thr | Ser | Val |
| 3605 | | | | | 3610 | | | | | 3615 | | | | |
| Gly | Pro | Pro | Glu | Phe | Ser | Arg | Thr | Val | Thr | Gly | Thr | Thr | Met | Thr |
| 3620 | | | | | 3625 | | | | | 3630 | | | | |
| Leu | Ile | Pro | Ser | Glu | Met | Pro | Thr | Pro | Pro | Lys | Thr | Ser | His | Gly |
| 3635 | | | | | 3640 | | | | | 3645 | | | | |
| Glu | Gly | Val | Ser | Pro | Thr | Thr | Ile | Leu | Arg | Thr | Thr | Met | Val | Glu |
| 3650 | | | | | 3655 | | | | | 3660 | | | | |
| Ala | Thr | Asn | Leu | Ala | Thr | Thr | Gly | Ser | Ser | Pro | Thr | Val | Ala | Lys |
| 3665 | | | | | 3670 | | | | | 3675 | | | | |
| Thr | Thr | Thr | Thr | Phe | Asn | Thr | Leu | Ala | Gly | Ser | Leu | Phe | Thr | Pro |
| 3680 | | | | | 3685 | | | | | 3690 | | | | |
| Leu | Thr | Thr | Pro | Gly | Met | Ser | Thr | Leu | Ala | Ser | Glu | Ser | Val | Thr |
| 3695 | | | | | 3700 | | | | | 3705 | | | | |
| Ser | Arg | Thr | Ser | Tyr | Asn | His | Arg | Ser | Trp | Ile | Ser | Thr | Thr | Ser |
| 3710 | | | | | 3715 | | | | | 3720 | | | | |
| Ser | Tyr | Asn | Arg | Arg | Tyr | Trp | Thr | Pro | Ala | Thr | Ser | Thr | Pro | Val |
| 3725 | | | | | 3730 | | | | | 3735 | | | | |
| Thr | Ser | Thr | Phe | Ser | Pro | Gly | Ile | Ser | Thr | Ser | Ser | Ile | Pro | Ser |
| 3740 | | | | | 3745 | | | | | 3750 | | | | |
| Ser | Thr | Ala | Ala | Thr | Val | Pro | Phe | Met | Val | Pro | Phe | Thr | Leu | Asn |
| 3755 | | | | | 3760 | | | | | 3765 | | | | |
| Phe | Thr | Ile | Thr | Asn | Leu | Gln | Tyr | Glu | Glu | Asp | Met | Arg | His | Pro |
| 3770 | | | | | 3775 | | | | | 3780 | | | | |
| Gly | Ser | Arg | Lys | Phe | Asn | Ala | Thr | Glu | Arg | Glu | Leu | Gln | Gly | Leu |
| 3785 | | | | | 3790 | | | | | 3795 | | | | |
| Leu | Lys | Pro | Leu | Phe | Arg | Asn | Ser | Ser | Leu | Glu | Tyr | Leu | Tyr | Ser |
| 3800 | | | | | 3805 | | | | | 3810 | | | | |
| Gly | Cys | Arg | Leu | Ala | Ser | Leu | Arg | Pro | Glu | Lys | Asp | Ser | Ser | Ala |
| 3815 | | | | | 3820 | | | | | 3825 | | | | |
| Thr | Ala | Val | Asp | Ala | Ile | Cys | Thr | His | Arg | Pro | Asp | Pro | Glu | Asp |
| 3830 | | | | | 3835 | | | | | 3840 | | | | |
| Leu | Gly | Leu | Asp | Arg | Glu | Arg | Leu | Tyr | Trp | Glu | Leu | Ser | Asn | Leu |
| 3845 | | | | | 3850 | | | | | 3855 | | | | |
| Thr | Asn | Gly | Ile | Gln | Glu | Leu | Gly | Pro | Tyr | Thr | Leu | Asp | Arg | Asn |
| 3860 | | | | | 3865 | | | | | 3870 | | | | |
| Ser | Leu | Tyr | Val | Asn | Gly | Phe | Thr | His | Arg | Ser | Ser | Met | Pro | Thr |
| 3875 | | | | | 3880 | | | | | 3885 | | | | |
| Thr | Ser | Thr | Pro | Gly | Thr | Ser | Thr | Val | Asp | Val | Gly | Thr | Ser | Gly |
| 3890 | | | | | 3895 | | | | | 3900 | | | | |
| Thr | Pro | Ser | Ser | Ser | Pro | Ser | Pro | Thr | Thr | Ala | Gly | Pro | Leu | Leu |
| 3905 | | | | | 3910 | | | | | 3915 | | | | |
| Met | Pro | Phe | Thr | Leu | Asn | Phe | Thr | Ile | Thr | Asn | Leu | Gln | Tyr | Glu |
| 3920 | | | | | 3925 | | | | | 3930 | | | | |
| Glu | Asp | Met | Arg | Arg | Thr | Gly | Ser | Arg | Lys | Phe | Asn | Thr | Met | Glu |
| 3935 | | | | | 3940 | | | | | 3945 | | | | |
| Ser | Val | Leu | Gln | Gly | Leu | Leu | Lys | Pro | Leu | Phe | Lys | Asn | Thr | Ser |
| 3950 | | | | | 3955 | | | | | 3960 | | | | |
| Val | Gly | Pro | Leu | Tyr | Ser | Gly | Cys | Arg | Leu | Thr | Leu | Leu | Arg | Pro |
| 3965 | | | | | 3970 | | | | | 3975 | | | | |
| Glu | Lys | Asp | Gly | Ala | Ala | Thr | Gly | Val | Asp | Ala | Ile | Cys | Thr | His |
| 3980 | | | | | 3985 | | | | | 3990 | | | | |

-continued

| | | | | | | | | | | |
|---|---|---|---|---|---|---|---|---|---|---|
| Arg | Leu | Asp | Pro | Lys | Ser | Pro | Gly | Leu | Asn | Arg | Glu | Gln | Leu | Tyr |
| | 3995 | | | | 4000 | | | | 4005 | |

Arg Leu Asp Pro Lys Ser Pro Gly Leu Asn Arg Glu Gln Leu Tyr
     3995                4000                4005

Trp Glu Leu Ser Lys Leu Thr Asn Asp Ile Glu Glu Leu Gly Pro
     4010                4015                4020

Tyr Thr Leu Asp Arg Asn Ser Leu Tyr Val Asn Gly Phe Thr His
     4025                4030                4035

Gln Ser Ser Val Ser Thr Thr Ser Thr Pro Gly Thr Ser Thr Val
     4040                4045                4050

Asp Leu Arg Thr Ser Gly Thr Pro Ser Ser Leu Ser Ser Pro Thr
     4055                4060                4065

Ile Met Ala Ala Gly Pro Leu Leu Val Pro Phe Thr Leu Asn Phe
     4070                4075                4080

Thr Ile Thr Asn Leu Gln Tyr Gly Glu Asp Met Gly His Pro Gly
     4085                4090                4095

Ser Arg Lys Phe Asn Thr Thr Glu Arg Val Leu Gln Gly Leu Leu
     4100                4105                4110

Gly Pro Ile Phe Lys Asn Thr Ser Val Gly Pro Leu Tyr Ser Gly
     4115                4120                4125

Cys Arg Leu Thr Ser Leu Arg Ser Glu Lys Asp Gly Ala Ala Thr
     4130                4135                4140

Gly Val Asp Ala Ile Cys Ile His His Leu Asp Pro Lys Ser Pro
     4145                4150                4155

Gly Leu Asn Arg Glu Arg Leu Tyr Trp Glu Leu Ser Gln Leu Thr
     4160                4165                4170

Asn Gly Ile Lys Glu Leu Gly Pro Tyr Thr Leu Asp Arg Asn Ser
     4175                4180                4185

Leu Tyr Val Asn Gly Phe Thr His Arg Thr Ser Val Pro Thr Thr
     4190                4195                4200

Ser Thr Pro Gly Thr Ser Thr Val Asp Leu Gly Thr Ser Gly Thr
     4205                4210                4215

Pro Phe Ser Leu Pro Ser Pro Ala Thr Ala Gly Pro Leu Leu Val
     4220                4225                4230

Leu Phe Thr Leu Asn Phe Thr Ile Thr Asn Leu Lys Tyr Glu Glu
     4235                4240                4245

Asp Met His Arg Pro Gly Ser Arg Lys Phe Asn Thr Thr Glu Arg
     4250                4255                4260

Val Leu Gln Thr Leu Val Gly Pro Met Phe Lys Asn Thr Ser Val
     4265                4270                4275

Gly Leu Leu Tyr Ser Gly Cys Arg Leu Thr Leu Leu Arg Ser Glu
     4280                4285                4290

Lys Asp Gly Ala Ala Thr Gly Val Asp Ala Ile Cys Thr His Arg
     4295                4300                4305

Leu Asp Pro Lys Ser Pro Gly Val Asp Arg Glu Gln Leu Tyr Trp
     4310                4315                4320

Glu Leu Ser Gln Leu Thr Asn Gly Ile Lys Glu Leu Gly Pro Tyr
     4325                4330                4335

Thr Leu Asp Arg Asn Ser Leu Tyr Val Asn Gly Phe Thr His Trp
     4340                4345                4350

Ile Pro Val Pro Thr Ser Ser Thr Pro Gly Thr Ser Thr Val Asp
     4355                4360                4365

Leu Gly Ser Gly Thr Pro Ser Ser Leu Pro Ser Pro Thr Ser Ala
     4370                4375                4380

-continued

Ala Gly Pro Leu Leu Val Pro Phe Thr Leu Asn Phe Thr Ile Thr
4385                4390                4395

Asn Leu Gln Tyr Glu Glu Asp Met His His Pro Gly Ser Arg Lys
4400                4405                4410

Phe Asn Thr Thr Glu Arg Val Leu Gln Gly Leu Leu Gly Pro Met
4415                4420                4425

Phe Lys Asn Thr Ser Val Gly Leu Leu Tyr Ser Gly Cys Arg Leu
4430                4435                4440

Thr Leu Leu Arg Ser Glu Lys Asp Gly Ala Ala Thr Gly Val Asp
4445                4450                4455

Ala Ile Cys Thr His Arg Leu Asp Pro Lys Ser Pro Gly Val Asp
4460                4465                4470

Arg Glu Gln Leu Tyr Trp Glu Leu Ser Gln Leu Thr Asn Gly Ile
4475                4480                4485

Lys Glu Leu Gly Pro Tyr Thr Leu Asp Arg Asn Ser Leu Tyr Val
4490                4495                4500

Asn Gly Phe Thr His Trp Ile Pro Val Pro Thr Ser Ser Thr Pro
4505                4510                4515

Gly Thr Ser Thr Val Asp Leu Gly Ser Gly Thr Pro Ser Ser Leu
4520                4525                4530

Pro Ser Pro Thr Thr Ala Gly Pro Leu Leu Val Pro Phe Thr Leu
4535                4540                4545

Asn Phe Thr Ile Thr Asn Leu Lys Tyr Glu Glu Asp Met His Cys
4550                4555                4560

Pro Gly Ser Arg Lys Phe Asn Thr Thr Glu Arg Val Leu Gln Ser
4565                4570                4575

Leu Leu Gly Pro Met Phe Lys Asn Thr Ser Val Gly Pro Leu Tyr
4580                4585                4590

Ser Gly Cys Arg Leu Thr Leu Leu Arg Ser Glu Lys Asp Gly Ala
4595                4600                4605

Ala Thr Gly Val Asp Ala Ile Cys Thr His Arg Leu Asp Pro Lys
4610                4615                4620

Ser Pro Gly Val Asp Arg Glu Gln Leu Tyr Trp Glu Leu Ser Gln
4625                4630                4635

Leu Thr Asn Gly Ile Lys Glu Leu Gly Pro Tyr Thr Leu Asp Arg
4640                4645                4650

Asn Ser Leu Tyr Val Asn Gly Phe Thr His Gln Thr Ser Ala Pro
4655                4660                4665

Asn Thr Ser Thr Pro Gly Thr Ser Thr Val Asp Leu Gly Thr Ser
4670                4675                4680

Gly Thr Pro Ser Ser Leu Pro Ser Pro Thr Ser Ala Gly Pro Leu
4685                4690                4695

Leu Val Pro Phe Thr Leu Asn Phe Thr Ile Thr Asn Leu Gln Tyr
4700                4705                4710

Glu Glu Asp Met His His Pro Gly Ser Arg Lys Phe Asn Thr Thr
4715                4720                4725

Glu Arg Val Leu Gln Gly Leu Leu Gly Pro Met Phe Lys Asn Thr
4730                4735                4740

Ser Val Gly Leu Leu Tyr Ser Gly Cys Arg Leu Thr Leu Leu Arg
4745                4750                4755

Pro Glu Lys Asn Gly Ala Ala Thr Gly Met Asp Ala Ile Cys Ser
4760                4765                4770

```
His Arg Leu Asp Pro Lys Ser Pro Gly Leu Asn Arg Glu Gln Leu
4775            4780                4785

Tyr Trp Glu Leu Ser Gln Leu Thr His Gly Ile Lys Glu Leu Gly
4790            4795                4800

Pro Tyr Thr Leu Asp Arg Asn Ser Leu Tyr Val Asn Gly Phe Thr
4805            4810                4815

His Arg Ser Ser Val Ala Pro Thr Ser Thr Pro Gly Thr Ser Thr
4820            4825                4830

Val Asp Leu Gly Thr Ser Gly Thr Pro Ser Ser Leu Pro Ser Pro
4835            4840                4845

Thr Thr Ala Val Pro Leu Leu Val Pro Phe Thr Leu Asn Phe Thr
4850            4855                4860

Ile Thr Asn Leu Gln Tyr Gly Glu Asp Met Arg His Pro Gly Ser
4865            4870                4875

Arg Lys Phe Asn Thr Thr Glu Arg Val Leu Gln Gly Leu Leu Gly
4880            4885                4890

Pro Leu Phe Lys Asn Ser Ser Val Gly Pro Leu Tyr Ser Gly Cys
4895            4900                4905

Arg Leu Ile Ser Leu Arg Ser Glu Lys Asp Gly Ala Ala Thr Gly
4910            4915                4920

Val Asp Ala Ile Cys Thr His His Leu Asn Pro Gln Ser Pro Gly
4925            4930                4935

Leu Asp Arg Glu Gln Leu Tyr Trp Gln Leu Ser Gln Met Thr Asn
4940            4945                4950

Gly Ile Lys Glu Leu Gly Pro Tyr Thr Leu Asp Arg Asn Ser Leu
4955            4960                4965

Tyr Val Asn Gly Phe Thr His Arg Ser Ser Gly Leu Thr Thr Ser
4970            4975                4980

Thr Pro Trp Thr Ser Thr Val Asp Leu Gly Thr Ser Gly Thr Pro
4985            4990                4995

Ser Pro Val Pro Ser Pro Thr Thr Ala Gly Pro Leu Leu Val Pro
5000            5005                5010

Phe Thr Leu Asn Phe Thr Ile Thr Asn Leu Gln Tyr Glu Glu Asp
5015            5020                5025

Met His Arg Pro Gly Ser Arg Lys Phe Asn Ala Thr Glu Arg Val
5030            5035                5040

Leu Gln Gly Leu Leu Ser Pro Ile Phe Lys Asn Ser Ser Val Gly
5045            5050                5055

Pro Leu Tyr Ser Gly Cys Arg Leu Thr Ser Leu Arg Pro Glu Lys
5060            5065                5070

Asp Gly Ala Ala Thr Gly Met Asp Ala Val Cys Leu Tyr His Pro
5075            5080                5085

Asn Pro Lys Arg Pro Gly Leu Asp Arg Glu Gln Leu Tyr Trp Glu
5090            5095                5100

Leu Ser Gln Leu Thr His Asn Ile Thr Glu Leu Gly Pro Tyr Ser
5105            5110                5115

Leu Asp Arg Asp Ser Leu Tyr Val Asn Gly Phe Thr His Gln Asn
5120            5125                5130

Ser Val Pro Thr Thr Ser Thr Pro Gly Thr Ser Thr Val Tyr Trp
5135            5140                5145

Ala Thr Thr Gly Thr Pro Ser Ser Phe Pro Gly His Thr Glu Pro
5150            5155                5160
```

-continued

Gly Pro Leu Leu Ile Pro Phe Thr Phe Asn Phe Thr Ile Thr Asn
5165                5170                5175

Leu His Tyr Glu Glu Asn Met Gln His Pro Gly Ser Arg Lys Phe
5180                5185                5190

Asn Thr Thr Glu Arg Val Leu Gln Gly Leu Leu Lys Pro Leu Phe
5195                5200                5205

Lys Asn Thr Ser Val Gly Pro Leu Tyr Ser Gly Cys Arg Leu Thr
5210                5215                5220

Leu Leu Arg Pro Glu Lys Gln Glu Ala Ala Thr Gly Val Asp Thr
5225                5230                5235

Ile Cys Thr His Arg Val Asp Pro Ile Gly Pro Gly Leu Asp Arg
5240                5245                5250

Glu Arg Leu Tyr Trp Glu Leu Ser Gln Leu Thr Asn Ser Ile Thr
5255                5260                5265

Glu Leu Gly Pro Tyr Thr Leu Asp Arg Asp Ser Leu Tyr Val Asn
5270                5275                5280

Gly Phe Asn Pro Trp Ser Ser Val Pro Thr Thr Ser Thr Pro Gly
5285                5290                5295

Thr Ser Thr Val His Leu Ala Thr Ser Gly Thr Pro Ser Ser Leu
5300                5305                5310

Pro Gly His Thr Ala Pro Val Pro Leu Leu Ile Pro Phe Thr Leu
5315                5320                5325

Asn Phe Thr Ile Thr Asn Leu His Tyr Glu Glu Asn Met Gln His
5330                5335                5340

Pro Gly Ser Arg Lys Phe Asn Thr Thr Glu Arg Val Leu Gln Gly
5345                5350                5355

Leu Leu Lys Pro Leu Phe Lys Ser Thr Ser Val Gly Pro Leu Tyr
5360                5365                5370

Ser Gly Cys Arg Leu Thr Leu Arg Pro Glu Lys His Gly Ala
5375                5380                5385

Ala Thr Gly Val Asp Ala Ile Cys Thr Leu Arg Leu Asp Pro Thr
5390                5395                5400

Gly Pro Gly Leu Asp Arg Glu Arg Leu Tyr Trp Glu Leu Ser Gln
5405                5410                5415

Leu Thr Asn Ser Val Thr Glu Leu Gly Pro Tyr Thr Leu Asp Arg
5420                5425                5430

Asp Ser Leu Tyr Val Asn Gly Phe Thr His Arg Ser Ser Val Pro
5435                5440                5445

Thr Thr Ser Ile Pro Gly Thr Ser Ala Val His Leu Glu Thr Ser
5450                5455                5460

Gly Thr Pro Ala Ser Leu Pro Gly His Thr Ala Pro Gly Pro Leu
5465                5470                5475

Leu Val Pro Phe Thr Leu Asn Phe Thr Ile Thr Asn Leu Gln Tyr
5480                5485                5490

Glu Glu Asp Met Arg His Pro Gly Ser Arg Lys Phe Asn Thr Thr
5495                5500                5505

Glu Arg Val Leu Gln Gly Leu Leu Lys Pro Leu Phe Lys Ser Thr
5510                5515                5520

Ser Val Gly Pro Leu Tyr Ser Gly Cys Arg Leu Thr Leu Leu Arg
5525                5530                5535

Pro Glu Lys Arg Gly Ala Ala Thr Gly Val Asp Thr Ile Cys Thr
5540                5545                5550

```
His Arg Leu Asp Pro Leu Asn Pro Gly Leu Asp Arg Glu Gln Leu
5555                5560                5565

Tyr Trp Glu Leu Ser Lys Leu Thr Arg Gly Ile Ile Glu Leu Gly
5570                5575                5580

Pro Tyr Leu Leu Asp Arg Gly Ser Leu Tyr Val Asn Gly Phe Thr
5585                5590                5595

His Arg Asn Phe Val Pro Ile Thr Ser Thr Pro Gly Thr Ser Thr
5600                5605                5610

Val His Leu Gly Thr Ser Glu Thr Pro Ser Ser Leu Pro Arg Pro
5615                5620                5625

Ile Val Pro Gly Pro Leu Leu Val Pro Phe Thr Leu Asn Phe Thr
5630                5635                5640

Ile Thr Asn Leu Gln Tyr Glu Glu Ala Met Arg His Pro Gly Ser
5645                5650                5655

Arg Lys Phe Asn Thr Thr Glu Arg Val Leu Gln Gly Leu Leu Arg
5660                5665                5670

Pro Leu Phe Lys Asn Thr Ser Ile Gly Pro Leu Tyr Ser Ser Cys
5675                5680                5685

Arg Leu Thr Leu Leu Arg Pro Glu Lys Asp Lys Ala Ala Thr Arg
5690                5695                5700

Val Asp Ala Ile Cys Thr His His Pro Asp Pro Gln Ser Pro Gly
5705                5710                5715

Leu Asn Arg Glu Gln Leu Tyr Trp Glu Leu Ser Gln Leu Thr His
5720                5725                5730

Gly Ile Thr Glu Leu Gly Pro Tyr Thr Leu Asp Arg Asp Ser Leu
5735                5740                5745

Tyr Val Asp Gly Phe Thr His Trp Ser Pro Ile Pro Thr Thr Ser
5750                5755                5760

Thr Pro Gly Thr Ser Ile Val Asn Leu Gly Thr Ser Gly Ile Pro
5765                5770                5775

Pro Ser Leu Pro Glu Thr Thr Ala Thr Gly Pro Leu Leu Val Pro
5780                5785                5790

Phe Thr Leu Asn Phe Thr Ile Thr Asn Leu Gln Tyr Glu Glu Asn
5795                5800                5805

Met Gly His Pro Gly Ser Arg Lys Phe Asn Ile Thr Glu Ser Val
5810                5815                5820

Leu Gln Gly Leu Leu Lys Pro Leu Phe Lys Ser Thr Ser Val Gly
5825                5830                5835

Pro Leu Tyr Ser Gly Cys Arg Leu Thr Leu Leu Arg Pro Glu Lys
5840                5845                5850

Asp Gly Val Ala Thr Arg Val Asp Ala Ile Cys Thr His Arg Pro
5855                5860                5865

Asp Pro Lys Ile Pro Gly Leu Asp Arg Gln Gln Leu Tyr Trp Glu
5870                5875                5880

Leu Ser Gln Leu Thr His Ser Ile Thr Glu Leu Gly Pro Tyr Thr
5885                5890                5895

Leu Asp Arg Asp Ser Leu Tyr Val Asn Gly Phe Thr Gln Arg Ser
5900                5905                5910

Ser Val Pro Thr Thr Ser Ser Glu Tyr Ser Thr Asp Val Pro Met
5915                5920                5925

Ala Pro Ile Leu Gln Gln Thr
5930                5935
```

```
<210> SEQ ID NO 9
<211> LENGTH: 21
<212> TYPE: DNA
<213> ORGANISM: Artificial
<220> FEATURE:
<223> OTHER INFORMATION: Outer gene-specific primer for 5' RACE
<220> FEATURE:
<221> NAME/KEY: misc_feature
<222> LOCATION: (1)..(21)
<223> OTHER INFORMATION: Outer gene-specific primer for 5' RACE

<400> SEQUENCE: 9
tcacagtccc tacattgact a                                              21

<210> SEQ ID NO 10
<211> LENGTH: 18
<212> TYPE: DNA
<213> ORGANISM: Artificial
<220> FEATURE:
<223> OTHER INFORMATION: Inner gene-specific primer for 5' RACE
<220> FEATURE:
<221> NAME/KEY: misc_feature
<222> LOCATION: (1)..(18)
<223> OTHER INFORMATION: Inner gene-specific primer for 5' RACE

<400> SEQUENCE: 10
catggcacat ctccagga                                                  18

<210> SEQ ID NO 11
<211> LENGTH: 21
<212> TYPE: PRT
<213> ORGANISM: Homo sapiens
<220> FEATURE:
<221> NAME/KEY: PEPTIDE
<222> LOCATION: (1)..(21)

<400> SEQUENCE: 11

Ser Ser Val Pro Thr Thr Ser Thr Pro Ser Ser Val Ser Thr Thr Ser
1               5                  10                  15

Thr Thr Ser Thr Pro
            20

<210> SEQ ID NO 12
<211> LENGTH: 52
<212> TYPE: PRT
<213> ORGANISM: Homo sapiens
<220> FEATURE:
<221> NAME/KEY: PEPTIDE
<222> LOCATION: (1)..(52)

<400> SEQUENCE: 12

Ala Gln Pro Gly Thr Thr Asn Tyr Gln Arg Asn Lys Ser Pro Arg Leu
1               5                  10                  15

Asp Arg Pro Leu Phe Lys Pro Gly Leu Lys Ala Gln Pro Gly Thr Thr
            20                  25                  30

Asn Tyr Gln Arg Asn Arg Thr Pro Asp Thr Ser Thr Met His Leu Ala
        35                  40                  45

Thr Ser Arg Thr
    50

<210> SEQ ID NO 13
<211> LENGTH: 38
<212> TYPE: PRT
<213> ORGANISM: Homo sapiens
<220> FEATURE:
<221> NAME/KEY: PEPTIDE
<222> LOCATION: (1)..(38)
```

```
-continued

<220> FEATURE:
<221> NAME/KEY: misc_feature
<222> LOCATION: (27)..(27)
<223> OTHER INFORMATION: Xaa can be any naturally occurring amino acid
<220> FEATURE:
<221> NAME/KEY: misc_feature
<222> LOCATION: (37)..(37)
<223> OTHER INFORMATION: Xaa can be any naturally occurring amino acid

<400> SEQUENCE: 13

Gly Pro Leu Tyr Ser Cys Arg Leu Thr Leu Leu Arg Glu Leu Gly Pro
1               5                   10                  15

Tyr Thr Leu Phe Thr Leu Asn Phe Thr Ile Xaa Asn Leu Pro Gly Ser
            20                  25                  30

Arg Lys Phe Asn Xaa Thr
        35
```

NUCLEIC ACID SEQUENCE ENCODING OVARIAN ANTIGEN, CA125, AND USES THEREOF

This application is a continuation-in-part of U.S. Ser. No. 10/142,515, filed on 09 May 2002, now abandoned, and is a continuation-in-part of International Application No. PCT/US02/14768, filed on 09 May 2002, which claim benefit of U.S. Ser. No. 60/290,480, filed on 11 May 2001, now abandoned, the contents of which are incorporated here into this application.

The invention disclosed herein was made with government support under NIH Grants No. CA52477 and CA08748, from the United States Department of Health and Human Services. Accordingly, the U.S. Government has certain rights in this invention.

Throughout this application, various references are referred to. Disclosures of these publications in their entireties are hereby incorporated by reference into this application to more fully describe the state of the art to which this invention pertains.

BACKGROUND OF THE INVENTION

CA125 antigen is a serum marker that is used routinely in gynecologic practice to monitor patients with ovarian cancer. It is a mullerian duct differentiation antigen that is overexpressed in epithelial ovarian cancer cells and secreted into the blood, although its expression is not entirely confined to ovarian cancer. CA125 was first identified by Bast and Knapp (1) in 1981 by a monoclonal antibody (OC125) that had been developed from mice immunized with an ovarian cancer cell line. These investigators subsequently developed a radio-immunoassay for the antigen and showed that serum CA125 levels are elevated in about 80% of patients with epithelial ovarian cancer (EOC)[1] but in less than 1% of healthy women (2). Numerous studies since that time have confirmed the usefulness of CA125 levels in monitoring the progress of patients with EOC (3–6). Most reports indicate that a rise in CA125 levels precedes clinical detection by about 3 months. During chemotherapy, changes in serum CA125 levels correlate with the course of the disease. CA125 is being used in the inventors' Medical Center, and elsewhere, as a surrogate marker for clinical response in phase II trials of new drugs. On the other hand, CA125 is not useful in the initial diagnosis of EOC because of its elevation in a number of benign conditions (3, 7). Despite this limitation, CA125 is considered to be one of the best available cancer serum markers, however more information on its molecular nature is needed to fully explore its potential.

Although CA125 antigen was first detected over 20 years ago, very little is known about its biochemistry and genetics. Most biochemical studies have concluded that CA125 is a high molecular weight glycoprotein, although estimates of its size range from 200 to 2000 kDa with smaller "subunits" being described by some investigators (8–13). Most studies have shown that CA125 is a mucin-type molecule, but others have claimed that it is a typical glycoprotein with asparagine-linked sugar chains (14). Another study claimed that CA125 is a glycosyl-phosphoinositol-linked glycoprotein (11). Thus, no consensus emerged from these studies concerning the biochemical nature of this antigen. Recently, however, our studies have strongly indicated that CA125 is a typical mucin molecule with a high carbohydrate content and a preponderance of serine and threonine-linked (O-linked) glycan chains (15, 16). Possibly because of the mucinous nature of CA125 its peptide moiety has been very difficult to clone. The only published study on this topic (17) described the isolation of a novel cDNA, later termed NBR-1 (18), but this species does not seem to have any of the biochemical characteristics expected for CA125 and may, in fact, be a transcription factor. Using a rabbit antiserum to purified CA125 we have now cloned, by expression cloning, a long partial cDNA sequence corresponding to a new mucin species (designated CA125/MUC16A) that is a strong candidate for being the peptide core of the CA125 antigen.

SUMMARY OF THE INVENTION

The invention disclosed herein provides an isolated nucleic acid molecule comprising sequences encoding the CA125 protein or a portion thereof. This invention also provides the gene encoding the CA125 protein.

In addition, this invention provides a vaccine for cancer which expresses CA125 protein comprising an appropriate amount of the isolated nucleic acid molecules which, when expressed, are capable of producing a product which induces an immune response to CA125 protein. This invention also provides a vaccine for cancer which expresses CA125 protein comprising an appropriate amount of a substance which induces an immune response to CA125 protein. This invention also provides a method for the diagnosis of a cancer which expresses CA125 by detecting CA125-expressing cells in the blood or other fluids of patients based on the nucleic acid sequence which encodes CA125. Furthermore, this invention provides a method for monitoring the therapy of a cancer which expresses CA125 by measuring the expression of CA125-expressing cells in the blood or other fluids of patients based on the nucleic acid sequence which encodes CA125, a decrease of either the number of CA125-expressing cells or level of protein expression in the cell, indicating the success of the therapy.

In addition, this invention provides a method of producing CA125 protein comprising steps of: a) constructing a vector adapted for expression in a cell which comprises the regulatory elements necessary for expression of nucleic acid in the cell operatively linked to the nucleic acid encoding the CA125 protein so as to permit expression thereof; b) placing the cells of step (a) under conditions allowing the expression of the CA125 protein; and c) recovering the CA125 protein so expressed.

Finally, this invention provides a nonhuman organism, wherein the expression of CA125 is inhibited.

DETAILED DESCRIPTION OF THE FIGURES

First Series of Experiments

FIG. 1. SDS-PAGE analysis of purified CA125 sample. The gel (3% stacking gel and 5% separating gel) was run under reducing conditions and stained with silver reagent. The arrowhead indicates the interface between the stacking and separating gels. The migration positions of molecular weight markers (in kDa) are shown on the right hand side. The bracket indicates the region of the gel used to immunize a rabbit to produce the polyclonal anti-CA125 serum.

FIG. 2. Nucleotide sequence at 3' end of the B4 clone of CA125/MUC16A (SEQ. ID NO. 1). The nucleotide and amino acid sequence for the B4 (CA125/MUC16A) have been deposited in the GenBank™ under accession number AF361486. * indicates a stop codon. A ployadenylation signal sequence is underlined.

FIG. 3. Deduced amino acid sequence of CA125/MUC16A (B4) organized to indicate the regions of homology in the tandem repeats (SEQ. ID NO. 2, 3 and 4,). Clustered serine and threonine residues are highlighted in white/shade and conserved cysteine residues in bold/shade. Potential N-linked glycosylation sites (Asn) are indicated in bold type. The possible transmembrane region is underlined and the consensus tyrosine phosphrylation motif is indicated in regular/shade. * indicates residues that are perfectly conserved, except in the last repeat sequence.—indicates gaps introduced to preserve the best homology in the repeats.

Figure 4:
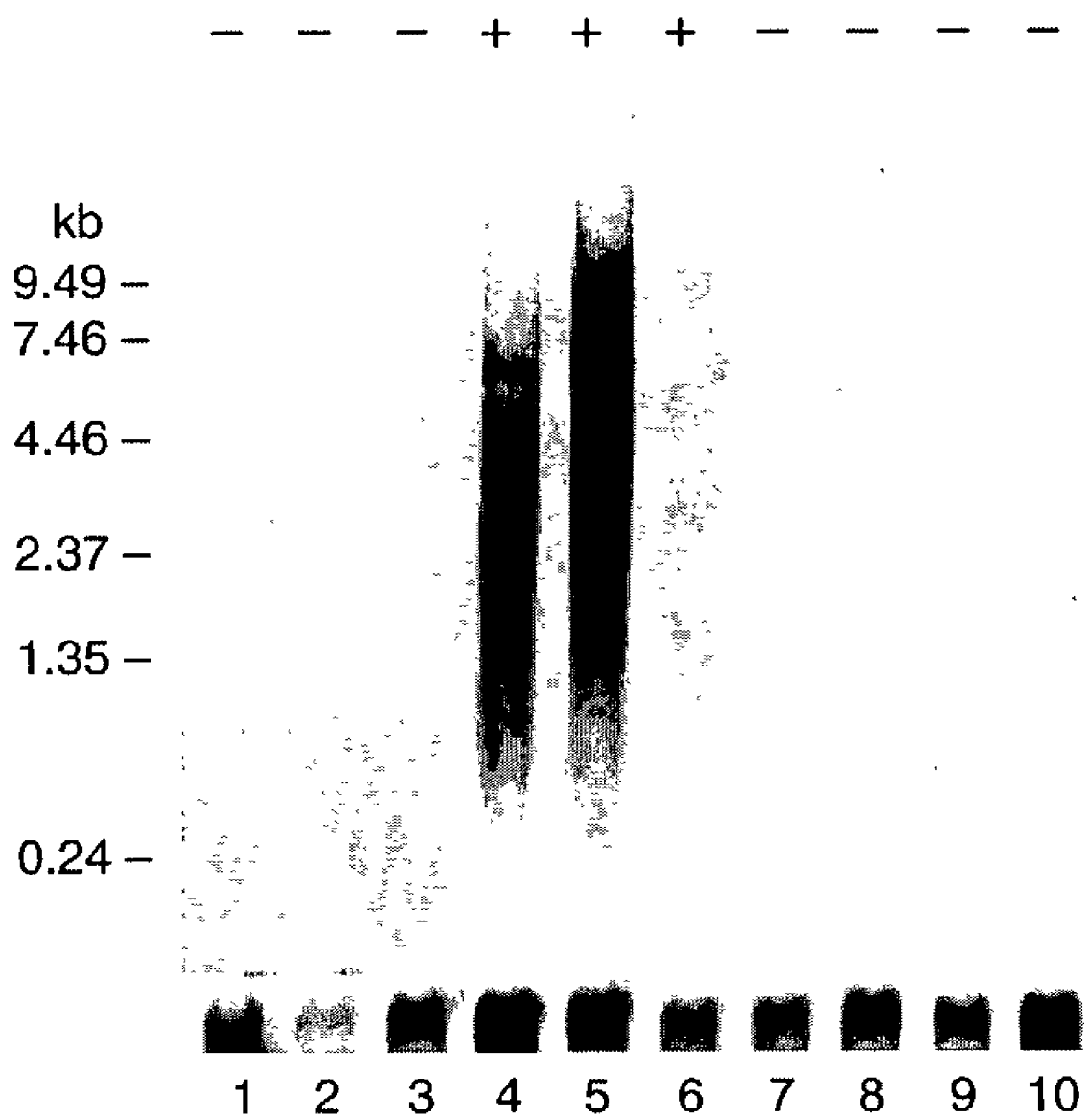

FIG. 4. Northern blot analysis of expression of CA125/MUC16A in cancer cell lines. The blot was probed with a biotin-labeled probe (B53) from the tandem repeat region. 1: SW626 (ovarian cancer); 2: 2774 (ovarian cancer); 3: SK-OV-3 (ovarian cancer); 4: SK-OV-8 (ovarian cancer); 5: OVCAR-3 (ovarian cancer); 6: COLO316 (ovarian cancer); 7: MCF-7 (breast cancer); 8: IMR-3 (neuroblastoma); 9: MKN45 (gastric cancer); 10: MCA (sarcoma). Indicated on the top of the figure (+ or −) is the expression of CA125 in the cell line as determined by reactivity with anti-CA125 antibodies. The end-point titers for these cell lines with mAb OC125 were 1—<1:500; 2—<1:500; 3−<1:500; 4—1: 128, 000; 5—>1: 256,000; 6—1:4000; 7—<1:500; 8—<1:500; 9—<1:500; 10—<1:500. Screening with mAb VK-8 gave similar results. The result of probing the blot with a β-actin probe is shown in the lower half of the figure. Size standards are indicated on the left side of the gel.

FIG. 5. Nucleotide sequence of B4 polynucleotide (CA125/MUC16A) (SEQ. ID NO. 5).

Figure 6:
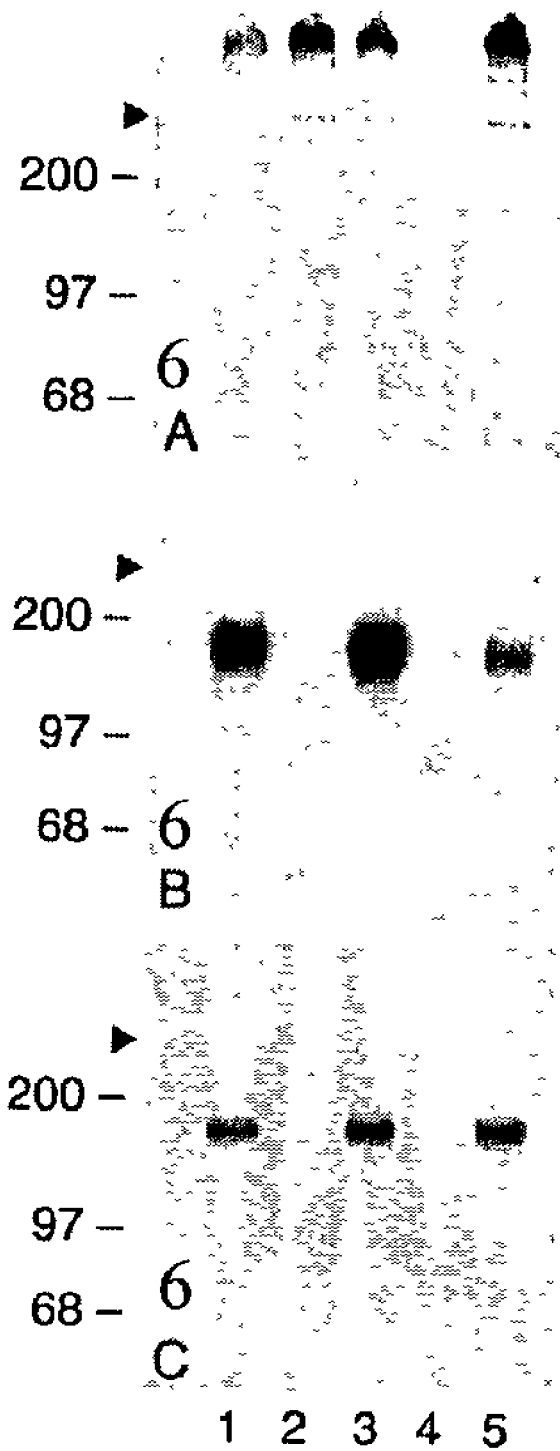

FIG. 6. Radioimmunoprecipitation analysis of reactivity of mouse and rabbit antibodies with culture supernatants of transfected cells. A: OVCAR 3 cells; B: SW626/B53 transfectant; C: SK-OV-3/B53 transfectant. 1: mAb OC125; 2: mAb M11; 3: mAb VK-8; 4: normal mouse serum; 5: rabbit anti-CA125 serum. Autoradiograms of SDS-PAGE gels are shown. The arrow head indicates the interface between the stacking (3%) and separating (7.5%) gels. Molecular masses of standard proteins are indicated on the right hand side. Exposure times for films were: A: 23 days; B: 1 day; C: 21 days. Reexposure of gel B for 6 days showed a faint band in lane 2 also.

Second Series of Experiments

FIG. 7. 3' sequence of clone B30. (SEQ. ID NO. 6). The sequence of the primer used for 3' RACE is underlined. The stop codon in the nucleotide sequence is indicated in bold type.

FIG. 8. Nucleotide sequence of MUC18B (SEQ. ID NO. 7).

Figure 9:
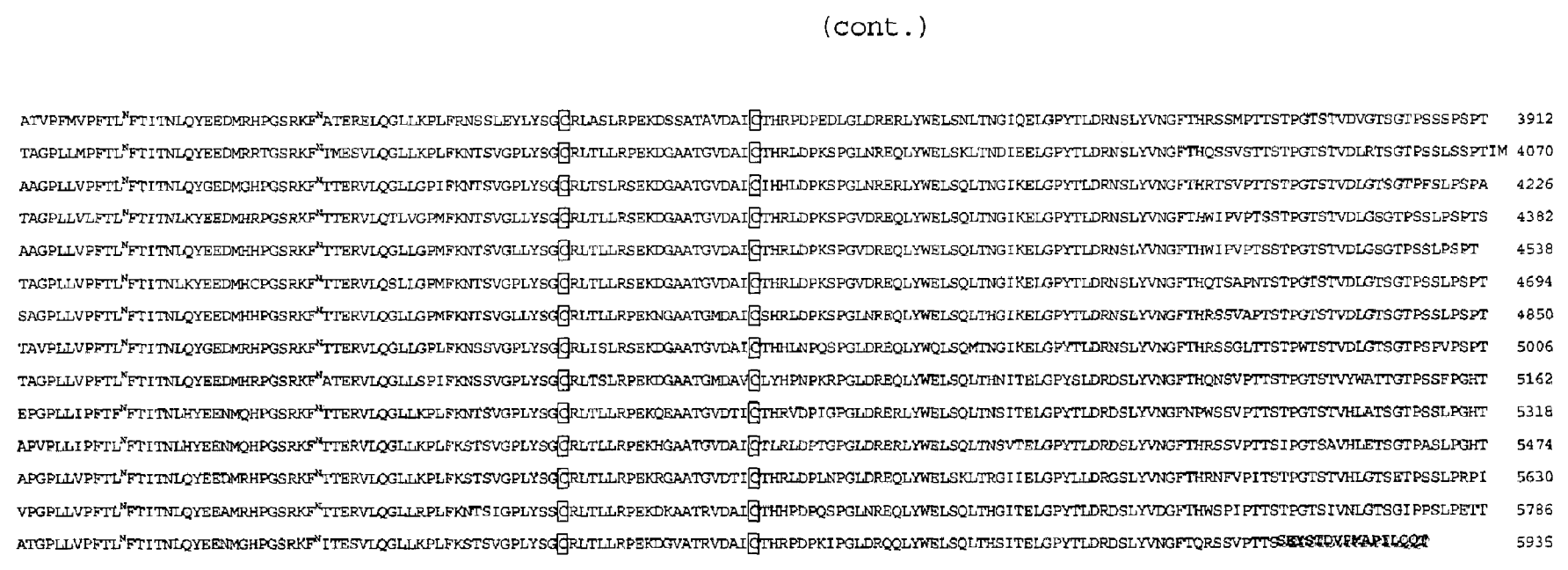

FIG. 9. Amino acid sequence of MUC16B (SEQ. ID NO. 8). The first four methionines (M) are underlined, and indicate possible start sites. The first 3756 aa indicate a non TR region of the protein S/T/P rich. From aa 3757 to 5920 the sequence is arranged to highlight the homology between the nearly 14 TR. The putative N-glycosylation sites are indicated in superscript. The conserved cysteine residues possibly delineating peptide loop structures are indicated by boxes In blue is indicated the region coded by the initial B30 clone. This region overlaps partially with the region coded by the B4 clone (indicated by any underline). Embossed are the last 16 aa of the MUC16B protein that do not belong to a TR regional and do not share homology with the MUC16A protein.

Figure 10:
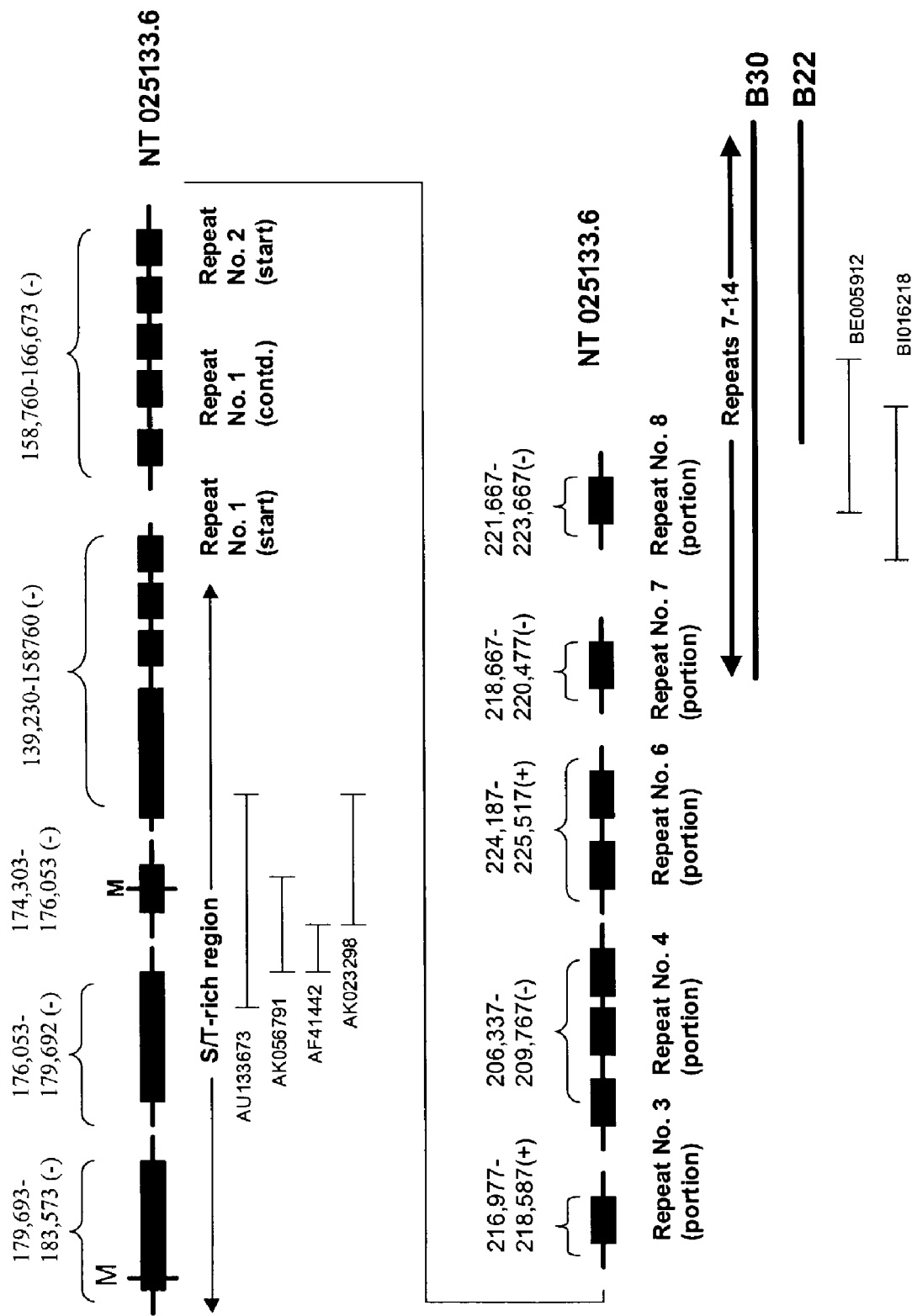

FIG. 10. Schematic showing relationship of NCBI gene sequence NT 025133.6 to clone B30 and various expressed sequence tags and the use of this information in determining the sequence of MUC16B. Exons are shown as filled boxes and the orientation of the reading frames (+ or −) are indicated for each exon.

Figure 11:
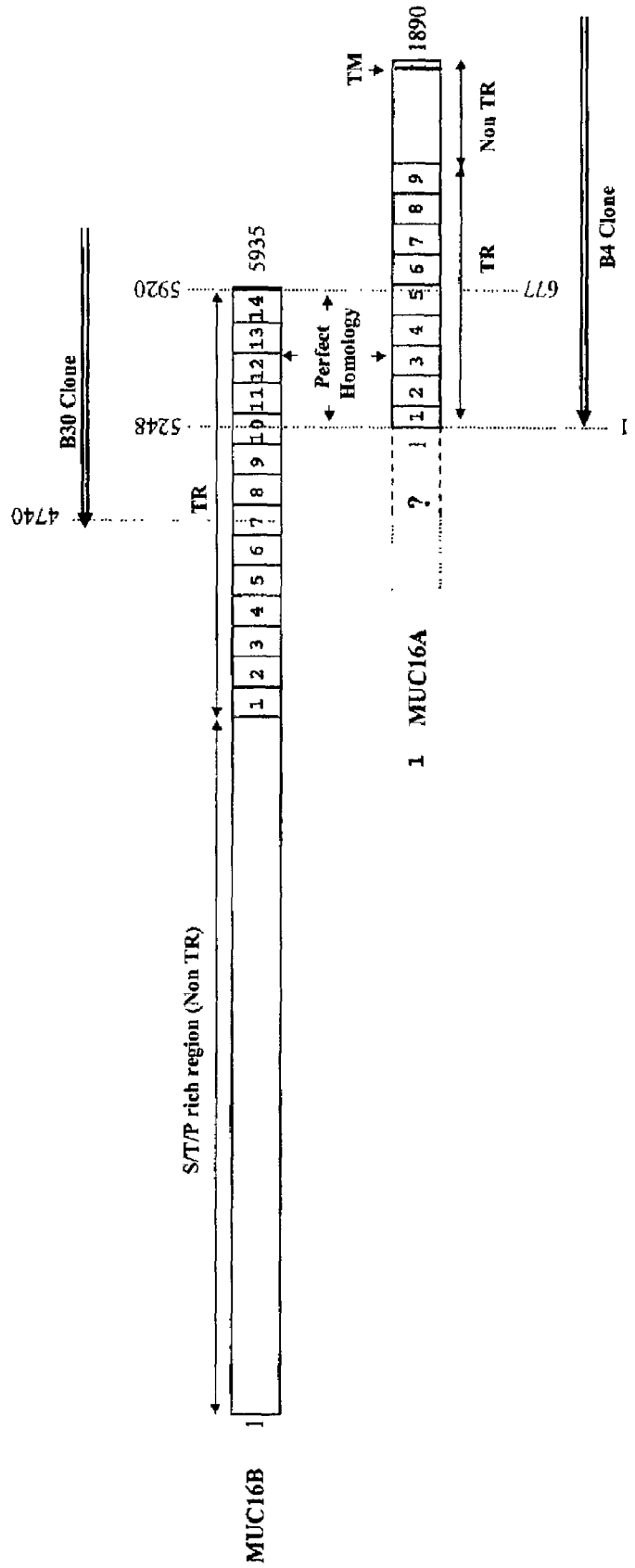

FIG. 11. Schematic showing the relationship between MUC16A and MUC16B proteins. For MUC16B the complete aa sequence is shown, with a N-ter region rich in serines, threonines and prolines (S/T/P rich region) and a C-ter containing 14 tandem repeats (TR). For MUC16A the N-ter is not yet elucidated (indicated by a "?" sign). Indicated are the 4.4 TR for which MUC16A and MUC16B coincide perfectly in the aa and nucleotide sequence. To the C-ter of this homology region, MUC16B has a non-TR region of 16 aa completely different to MUC16A, they constitute the end of the protein. After the region of homology to MUC16B, MUC16A has around 4.5 more TR (677aa–1345aa) to the C-ter followed by a non-TR region, a single putative transmembrane domain (TM) and a short intracytoplasmic tail.

DETAILED DESCRIPTION OF THE INVENTION

The invention disclosed herein provides an isolated nucleic acid molecule comprising sequences encoding the CA125 protein or a portion thereof. This invention also provides the gene encoding the CA125 protein. This invention further comprises the 5' untranslated sequence of the CA125 gene. In addition, this invention comprises the 3' untranslated sequence of the CA125 gene.

In addition, this invention provides the above isolated nucleic acid molecule comprising sequence set forth in FIG. 5, or a portion thereof, and the corresponding CA125 protein comprising sequence set forth in FIG. 3, or a portion thereof. In an embodiment, the nucleic acid comprises sequence set forth in FIG. 8, or a portion thereof. In another embodiment, the nucleic acid encoding protein comprises at least a portion of the amino acid sequence set forth in FIG. 9, or a portion thereof.

This invention also provides the above gene comprising sequence set forth in FIG. 7, or a portion thereof.

The invention furthermore provides the above isolated nucleic acid molecules, wherein the nucleic acid is RNA, cDNA, genomic DNA, or synthetic DNA. This invention also provides a vector comprising the above nucleic acid molecule. In an embodiment, the vector is designated as pBK-CMV-B4 comprising sequence set forth in FIG. 5, or a portion thereof, and the corresponding CA125 protein comprising sequence set forth in FIG. 3, or a portion thereof. In yet another embodiment, the vector is designated as pCMV-Tag-B4 comprising sequence set forth in FIG. 5, or a portion thereof, and the corresponding CA125 protein comprising sequence set forth in FIG. 3, or a portion thereof.

This invention provides an expression system comprising the above vector. In an embodiment, the system is a eukaryotic or prokaryotic system. This invention further provides a method for producing CA125 protein comprising the above expression system.

This invention further provides an isolated nucleic acid molecule comprising sequence capable of specifically hybridizing to the sequences above. In an embodiment, the nucleic acid molecule is capable of inhibiting the expression of the CA125 protein. A method of inhibiting expression of CA125 inside a cell by vector-directed expression of a short RNA which short RNA can fold in itself and create a double strand RNA, which sequence has CA125 mRNA sequence identity, able to trigger posttranscriptional gene silencing, or RNA interference (RNAi), of the CA125 gene inside said cell. A method of inhibiting expression of CA125 inside a cell by delivering inside said cell a short double strand RNA, which sequence has CA125 mRNA sequence identity, able to trigger posttranscriptional gene silencing, or RNAi, of the CA125 gene inside said cell. In another embodiment, the nucleic acid molecule is at least a 7 mer. In another embodiment, it is at least a 10 mer. In a separate embodiment, the nucleic acid molecule is at least a 20 mer. In a further embodiment, the sequence is unique.

This invention further provides a method to detect ovarian cancer in a subject comprising steps of: a) contacting the above isolated nucleic acid molecule with RNA from a sample from the subject under conditions permitting the formation of a hybrid complex, and b) detecting the hybrid complex, wherein a positive detection indicates the expression of the antigen and presence of cancer.

Furthermore, this invention provides a method of monitoring ovarian cancer therapy in a subject comprising steps of: a) contacting the above isolated nucleic acid molecule with RNA from a sample from the subject under conditions permitting the formation of a hybrid complex, and b) measuring the amount of the hybrid complex, wherein a decrease in the hybrid complex indicates the success of therapy.

This invention also provides a method for inhibiting the expression of the CA125 protein comprising contacting an appropriate amount of the above nucleic acid molecule so that hybridization of the gene or transcript encoding the CA125 protein will occur, thereby inhibiting the expression of the protein. This invention further provides a composition comprising the above isolated nucleic acid molecule.

In addition, this invention provides a vaccine for a cancer which expresses CA125 protein comprising an appropriate amount of the above isolated nucleic acid molecules.

In a separate embodiment, this invention provides a vaccine for a cancer which expresses CA125 protein comprising an appropriate amount of the isolated nucleic acid molecules which, when expressed, are capable of producing a product which induces an immune response to CA125 protein. In an embodiment, the nucleic acid molecule comprises sequences encoding human CA125 protein or a portion thereof.

In another embodiment, the expressed human sequence is linked to a carrier. It is known that a carrier can booster immune response. The said carrier may be a protein carrier.

In yet another embodiment, the nucleic acid molecule comprises a nonhuman sequence. In a further embodiment, the nucleic acid molecule comprises a primate sequence. In an additional embodiment, the nucleic acid molecule comprises a murine sequence. In a further embodiment, it comprises a rat or mouse sequence. In yet another embodiment, the nucleic acid molecule comprises a synthetic sequence, which, when expressed, is capable of producing a product which induces an immune response to CA125 protein.

In addition, this invention provides the vaccine wherein the sequence hybridizes with or is homologous to the sequences encoding human CA125 protein. In an embodiment, the vaccine further comprising a suitable adjuvant. In an embodiment, the adjuvant is an alum. In another embodiment, the cancer is an ovarian, pancreatic, breast, endometrial, or lung carcinoma.

This invention also provides a method to treat a cancer which expresses CA125 in a subject comprising administering to the subject an appropriate amount of the above vaccine.

This invention also provides the above method, wherein the cancer is an ovarian, pancreatic, breast, endometrial, or lung carcinoma.

This invention further provides a vaccine for a cancer which expresses CA125 comprising an appropriate amount of the expressed CA125 protein corresponding to the above sequence.

This invention also provides a vaccine for a cancer which expresses CA125 protein comprising an appropriate amount of a substance which induces an immune response to CA125 protein. In an embodiment, the substance is a polypeptide or a peptide. In a separate embodiment, the polypeptide comprises sequences encoding human CA125 protein or a portion thereof. In yet another embodiment, the expressed human sequence is linked to a carrier. In a further embodiment, the polypeptide comprises a nonhuman sequence. In a separate embodiment, the polypeptide comprises a primate sequence. In another embodiment, the polypeptide comprises a murine sequence. In yet another embodiment, the polypeptide comprises a synthetic sequence, which, when expressed, is capable of producing a product which induces an immune response to CA125 protein. The production of a synthetic sequence or a hybrid of synthetic and natural sequences is well-known in this field. In separate embodiment, the vaccine further comprising a suitable adjuvant. In an embodiment, the adjuvant is an alum.

This invention provides the above vaccine, wherein the expressed protein is conjugated to a protein carrier to increase the immunogenicity. Furthermore, this invention provides the above vaccine, wherein the cancer is an ovarian, pancreatic, breast, endometrial, or lung carcinoma.

Furthermore, this invention provides a method to treat a cancer which expresses CA125 in a subject comprising administering to the subject an appropriate amount of the above vaccine.

This invention also provides a method to prevent a cancer which expresses CA125 in a subject comprising administering to the subject an appropriate amount of the above vaccine. In an embodiment, the cancer is an ovarian, pancreatic, breast, endometrial, or lung carcinoma.

In addition, this invention provides a method for the diagnosis of a cancer which expresses CA125 by detecting CA125-expressing cells in the blood or other fluids of patients based on the nucleic acid sequence which encodes CA125.

This invention also provides a method for monitoring the therapy of a cancer which expresses CA125 by measuring the expression of CA125-expressing cells in the blood or other fluids of patients based on the nucleic acid sequence which encodes CA125, a decrease of either the number of CA125-expressing cells or level of protein expression in the cell, indicating the success of the therapy. In an embodiment, the detection is based on polymerase chain reaction with appropriate primers.

This invention further provides a method of producing CA125 protein comprising steps of: a) constructing a vector adapted for expression in a cell which comprises the regulatory elements necessary for expression of nucleic acid in the cell operatively linked to the nucleic acid encoding the CA125 protein so as to permit expression thereof; b) placing the cells of step (a) under conditions allowing the expression of the CA125 protein; and c) recovering the CA125 protein so expressed. In an embodiment, the cell type is selected from the group consisting of bacterial cells, yeast cells, insect cells, and mammalian cells.

This invention also provides the CA125 protein expressed by the above method. This invention also provides a method for production of antibodies against CA125 protein using the protein. This invention also provides the antibodies produced by the above method. This invention also provides a method of diagnosis of cancer which expresses CA125 using the antibodies above. A method for monitoring the therapy of cancer which expresses CA125 using the above antibodies.

This invention further provides a method for determining the immunoreactive part of CA125 comprising contacting antibodies which are known to be reactive to CA125 with the protein above. Furthermore, this invention provides a transgenic nonhuman organism comprising the above isolated nucleic acid molecule. In an embodiment, the organism is a transgenic nonhuman mammal.

This invention also provides a nonhuman organism, wherein the expression of CA125 is inhibited. In an embodiment, the organism is a nonhuman mammal. In a separate embodiment, the mammal is a mouse.

Finally, this invention further provides a method for screening a compound for treatment of cancer which expresses CA125 protein comprising administering the compound to the transgenic nonhuman organism above, a decrease in expression of CA125 protein indicating that the compound may be useful for treatment of the cancer. In an embodiment, the cancer is an ovarian, pancreatic, breast, endometrial, or lung carcinoma.

The invention will be better understood by reference to the Experimental Details which follow, but those skilled in the art will readily appreciate that the specific experiments detailed are only illustrative, and are not meant to limit the invention as described herein, which is defined by the claims which follow thereafter.

CA125 is an ovarian cancer antigen that is basis for a widely-used serum assay for the monitoring of patients with ovarian cancer, however detailed information on its biochemical and molecular nature is lacking. The inventors now report the isolation of a long, but partial, cDNA that corresponds to the CA125 antigen. A rabbit polyclonal antibody produced to purified CA125 antigen was used to screen a λZAP cDNA library from OVCAR-3 cells in *Escherichia coli*. The longest insert from the 53 positive isolated clones had a 5965 b.p. sequence containing a stop codon and a poly A sequence but no clear 5' initiation sequence. The deduced amino acid sequence has many of the attributes of a mucin molecule and was designated CA125/MUC16. These features include a high serine, threonine, and proline content in an N-terminal region of close to nine partially conserved tandem repeats (156 amino acids each) and a C-terminal region non-tandem repeat sequence containing a possible transmembrane region and a potential tyrosine phosphorylation site. Northern blotting showed that the level of MUC16 mRNA correlated with the expression of CA125 in a panel of cell lines. The molecular cloning of CA125/MUC16 antigen will lead to a better understanding of its role in ovarian cancer.

Experimental Details

First Series of Experiments

Materials and Methods

NIH:OVCAR3 cell line was obtained from the American Type Culture Collection (Rockville, Md.). Anti-CA125 antibody mAb OC125 was a generous gift from Dr. R. Bast, Jr. mAb VK-8, developed in the inventors' Laboratory by immunization of mice with human ovarian cancer cell line OVCAR-3, also identifies CA125 but reacts with a different epitope(s) than OC125 (15). Tumor cell lines were from the Sloan-Kettering Institute Cell Bank.

Purification of CA125 Antigen

CA125 was purified from the culture supernatant of NIH:OVCAR-3 cells in a simple two-step procedure (15). Briefly, the cells were cultured as a monolayer in a synthetic medium (ITS, Life Technologies, Grand Island, N.Y.) in RPMI medium containing 1% fetal bovine serum (FBS) and the culture medium was harvested every 7 days. Medium from 31 liters of supernatant medium was concentrated 10 fold and precipitated with perchloric acid (0.6 M final concentration). After centrifuging, the neutralized supernatant was passed through a column of normal mouse Ig-agarose (30 ml; 1.0 mg/ml) and then through a column of VK-8 mAb (80 ml; 2.0 mg/ml). The antibodies were linked to Actigel ALD gel according to the manufacturer's directions (Sterogene Bioseparations, Inc., Carlsbad, Calif.). The VK-8 column was washed at 4° with PBS, then with 1M NaCl in PBS, and finally eluted with 3M $MgCl_2$. Fractions (6.0 ml) were collected and assayed for CA125 antigen by ELISA with mAb VK-8 as described (15). Fractions from the $MgCl_2$ eluate containing CA125 reactivity were pooled and used in subsequent studies. Analysis by SDS-PAGE and silver staining (FIG. 1) showed that the sample consisted of very high molecular weight components migrating in the stacking gel and in a region just below the gel interface; all these species were reactive with mAb OC125 (data not shown). The sample also contained a lower molecular weight species originating from the FBS used in the cell cultures. The amino acid content of the sample was determined as described previously (15).

Production of a Rabbit Antiserum to CA125 Antigen

The CA125 sample was further purified by preparative SDS-PAGE and the high molecular weight region of the gel indicated in FIG. 1 was excised. After homogenization in incomplete Freund's adjuvant the gel was used to immunize a rabbit (NZB white, female) by 3 subcutaneous injections, 1 week apart, in 8 sites. Serum was obtained from the rabbit 10 days after the final immunization. An aliquot (3.0 ml) of the serum was absorbed with a pellet of melanoma cells (SK-MEL-28, -23, -30 and -33; 6.7 ml) that had been treated with 0.2% NP40 and 0.1% protease inhibitor cocktail (Sigma Co., St. Louis, Mo.) and the absorbed serum was used to screen a cDNA library.

Screening of OVCAR-3 cDNA Library

A cDNA library was constructed from OVCAR-3 mRNA in the λZAP Express vector in *E. coli* as described by the manufacturer (Stratagene, La Jolla, Calif.). The library contained $7.5 \times 10^6$ p.f.u. The library was plated onto 15 plates at approximately 30,000 pfu/150 mm plate and plaques were transferred to nitrocellulose and screened with the absorbed rabbit antiserum (1:500). Positive plaques were identified using anti-rabbit Ig-horseradish peroxidase conjugate (Southern Biotechnology Assoc., Birmingham, Ala.) and 4-chloro-1-napthol reagent. After subcloning three times and retesting with antiserum, 54 positive clones remained. These clones contained inserts ranging from 1.5 to >4.0 kbp and were designated pBK-CMV-B1 to B54.

DNA Sequencing and Sequence Analysis

The nucleotide sequence of the longest insert (B4) was determined using Big Dye terminators (PE Biosystems) and run on ABI 3700 or ABI 377 DNA sequencer by the Cornell University BioResource Center, Ithaca, N.Y. Using the T3 primer and then a series of internal sequencing primers, corresponding to less conserved regions of the gene, a 5965 bp sequence was identified in B4. Partial sequencing of the other inserts demonstrated that the majority corresponded to different parts of the B4 sequence.

Northern Blot Analysis mRNA was isolated from a panel of human tumor cell lines, which had been serologically typed for CA125 expression, using an mRNA Isolation System kit (Invitrogen, Carlsbad, Calif.). mRNA samples (3 :g) were denatured with formaldehyde, separated by electrophoresis in 1.0% agarose and transferred to nylon sheets (Gene Screen Plus, NEN, Boston, Mass.). The blot was hybridized with a biotin-labeled probe from an insert containing 3 tandem repeat regions (B53) using a chemiluminescence procedure following the manufacturer's directions (Renaissance reagent; NEN, Boston, Mass.).

Serological Analysis

Tumor cell lines were assayed for CA125 expression with mAb OC125 and VK-8 using a red cell rosetting method as described previously (15).

Results

Cloning of CA125/MUC16A cDNA

Although most studies on the molecular cloning of mucins utilized polyclonal antisera raised to the deglycosylated mucin (apomucin), in this study we used a rabbit antiserum prepared against the native CA125 antigen. CA125 was purified by affinity chromatography on an anti-CA125 antibody (mAb VK-8) column by elution under mild conditions with a chaotropic ion (3M $MgCl_2$) as described previously (15). The purified sample had an amino acid composition similar to that found in other mucins (Table 1) and extremely high CA125 activity ($2\times10^6$ units/mg protein). To immunize rabbits the preparation was further purified by SDS-PAGE and gel slices containing high molecular weight CA125 antigen (FIG. 1) were used as the immunogen (in incomplete Freund's adjuvant). The resulting antiserum was absorbed with a pellet of non-ovarian cancer cells, after partially solubilizing the cells in 0.2% NP-40, to remove non-specific antibodies.

TABLE 1

Comparison of Amino Acid Content of Purified CA125 and Deduced Amino Acid Composition of CA125/MUC16 and Its Tandem Repeat Region

| Amino Acid | Purified CA125 moles % | CA125/ MUC16 moles % | CA125/ MUC16 (TR) moles % |
|---|---|---|---|
| Asn | 8.5 | 8.9 | 8.1 |
| Glx | 7.8 | 8.1 | 7.5 |
| Ser | 11.0 | 8.7 | 8.9 |
| Gly | 9.0 | 7.4 | 7.6 |
| His | 2.6 | 2.8 | 2.9 |
| Arg | 4.6 | 5.9 | 6.3 |
| Thr | 12.4 | 11.6 | 12.7 |
| Ala | 3.8 | 3.1 | 2.9 |
| Pro | 8.7 | 8.1 | 9.0 |
| Tyr | 2.6 | 3.8 | 3.3 |
| Val | 5.2 | 5.0 | 4.7 |
| Met | 1.2 | 1.1 | 1.0 |
| Cys | — | 1.4 | 1.2 |
| Iso | 2.7 | 3.3 | 3.1 |
| Leu | 12.4 | 13.4 | 13.7 |
| Phe | 3.7 | 3.9 | 3.6 |
| Lys | 3.8 | 3.0 | 2.9 |

The absorbed antiserum was used to screen a λZAP cDNA library from OVCAR-3 cells expressed in *E. coli*. Fifty-four positive clones were detected and 53 inserts were sequenced. Initial sequencing of the longest clone (B4) showed that it had 9 partially conserved repeats of 468 b.p. each and a short non-repetitive 3' region. Further sequencing with internal primers extended the 3' end of the sequence to include a stop codon, a polyadenylation signal and a poly A region for a total of 5965 b.p. (FIG. 2). No clear initiation sequence (ATG in a Kozak box) was detected at the 5'-end, indicating that the derived sequence is incomplete. The majority of the other inserts (B1–B53) had sequences derived from different parts of the B4 sequence. No clones containing only 3' non-repetitive sequences were identified. Searching GenBank™ revealed no related full-length cDNA but numerous related human ESTs (including Accession Numbers: AI566650, AI537678, AI276341, AI923224, AI276341, AU158364, AU140211, AK024365) and one mouse EST (AK003577) were detected. With minor exceptions, these sequences were identical to those derived for B4. The nucleotide sequence of B4 was designated CA125/MUC16.

Chromosomal Location of CA125/MUC16 Sequences

Comparison of the B4 sequence with the working draft version of the human genome, available from the NCBI, located homologous sequences on chromosome 19 (p13.3 region). As sequencing of this region is incomplete and presently consists of numerous unordered segments of varying lengths, more complete genomic information must await the availability of further sequencing data.

Analysis of the Deduced Amino Acid Sequence of CA125/MUC16A

The nucleotide was conceptually translated into an amino acid sequence assuming initiation at the ATG of the β-galactosidase gene in the vector. The deduced amino acid sequence of 1890 amino acids (FIG. 3) suggested a mucin-type molecule. It had an amino acid composition that was moderately high in serine (8.9%), threonine (12.5%) and proline (8.8%); this composition is very similar to that of the purified CA125 sample used in this study (Table 1), although the proportion of these three amino acids is lower than in most other mucins. The sequence contained a large region of 9 tandem repeats (TR) of 156 amino acids each and a C-terminal non-repetitive region of 537 amino acids. None of the 9 repeats are identical but numerous perfectly conserved residues and short sequences are apparent (FIG. 3). Two conserved cysteine residues within each of the TRs are notable. The serine and threonine residues are scattered throughout the sequence but the TR regions have prominent clusters of Ser and Thr, often with adjacent Pro residues which is a common feature of O-glycosylation sites (19), e.g. SSVPTTSTP (47–55 and 671–679) and SSVSTTSTTSTP (1139–1147). These characteristics are typical of mucins. The high Leu content of this sequence is, however, not found in other cloned mucins. Other features of interest include a sequence of hydrophobic amino acids (25 residues) towards the C-terminal end (presumably representing a transmembrane region) and a short 31- amino-acid cytoplasmic tail. This region also contains a consensus tyrosine phosphorylation site (RRKKEGEY; refs. 20, 21). Numerous potential N-linked glycosylation sites occur in both the TR and non-TR regions (FIG. 3).

Northern Blotting mRNA from a panel of ten CA125$^+$ and CA125$^-$ cell lines was screened with a probe derived from the tandem repeat region of MUC16A. Three of the cell lines gave positive blots and 7 were unreactive (FIG. 4). The polydisperse pattern obtained is typical of that observed with other mucin mRNAs. These data corresponded to the expression of CA125 antigen on the cell lines as determined by serological analysis with antibodies to CA125 (mAbs OC125 and VK-8). The strongest signal was given by mRNA from OVCAR-3 (lane 5), the cell line from which the CA125 was purified and the cDNA library was produced.

Peptide Sequences Derived from CA125 Antigen

Purified CA125 was deglycosylated by treatment with anhydrous HF at room temperature for 3 hrs (22). Two sequences were obtained from a tryptic digest of the HF-treated sample after SDS-PAGE and transfer of the 25–35 kDa region to a nitrocellulose membrane (22). The product was also digested with Lys-C in guanidinium hydrochloride; peptides were isolated by microbore HPLC, and four peptides were successfully sequenced (Table 2). Five of these peptides corresponded to sequences within the TR and one to a sequence in the C-terminal region of the deduced MUC16 sequence (Table 2).

noprecipitated from OVCAR3 cells (FIG. 6A) but this is to be expected as B53 contains only 3 tandem repeats in contrast to the >9 repeats present in the native CA125 gene. As the synthesized peptide would be expected to have a size of 99 kDa, based on its translated nucleotide sequence, the observed size difference (about 80 kDa) is probably due to glycosylation.

This result proves that the cloned nucleotide sequence contains the information for coding for the CA125 antigen.

Discussion

Based on the following evidence, the cloned MUC16 sequence is a strong candidate for being the cDNA for the peptide core of the CA125 antigen: (i) the CA125 antigen used in the study was isolated by affinity chromatography on an anti-CA125 monoclonal antibody column and was highly purified, (ii) peptides isolated from the purified CA125 sample corresponded to sequences in the cloned MUC16 sequence (iii) MUC16A mRNA levels in a panel of cancer cell lines, as determined by Northern blotting, correlated

TABLE 2

Amino Acid Sequences Derived from Purified CA125

| Sequence | Position in CA125/MUC16 sequences | |
|---|---|---|
| By Lys-C digestion | | |
| AQPGTTNYQRNK | 1722–1733 | (SEQ. ID NO. 12) |
| SPRLDR | 1098–1113 | B4 (MUC 16A) corresponds to SEQ. I.D. NOS. 1–5 |
| PLFK | 120–123, and other locations | B30 (MUC 16B) corresponds to SEQ. I.D. NOS. 6 and 8 |
| PGL | 7–9 and other locations | B22 (MUC 16B) corresponds to SEQ. I.D. NOS. 6 and 8 |
| By trypsin digestion | | |
| KAQPGTTNYQRN | 1721–1732 | |
| RTPDTSTMHLATSRT | 833–847 | |

Expression Analysis of CA125 Nucleotide Clone (FIG. 6)

This figure is the result of an expression experiment that confirms that the sequence actually codes for CA125, as recognized by standard antibodies.

Method

B53-containing plasmid was digested with EcoR1 to release inserts (2668 base pairs) containing 3 tandem repeat regions and the non-tandem repeat region, but excluding the transmembrane sequence. The DNA were inserted into the pSecTag2B vector (Invitrogen Corp, Carlsbad, Calif.) at the EcoR1 cloning site. This vector is designed for the high level expression and secretion of proteins in mammalian cells after Zeocin selection. Sequencing confirmed the integrity and orientation of the B53 inserts. Following transfection of the construct into either SK-OV-3 or SW626 CA125-negative cell lines with Lipofectamine Plus (Life Sciences), stable colonies were selected with Zeocin (1000 :g/ml for SW626 and 750 :g/ml for SK-OV-3) for 5 weeks. Colonies were isolated by trypsinization using a cloning ring. Cells were subsequently cultured in MEM-10% FBS. Cultured cells were metabolically labeled with [$^3$H]GlcN (250 :Ci/T75 flask) for 3 days in complete MEM-10% fetal bovine serum. The medium was then harvested and the cells were lysed in NP40-containing buffer. Aliquots of the medium and cell lysate were precipitated with appropriate antibodies, the complexes isolated with protein A-agarose and analyzed by SDS-PAGE. Bands corresponding to CA125 were observed in immunoprecipitates from SW626/B53 (FIG. 6B. lanes 1 and 3) and from SK-OV-3 (FIG. 6C lanes 1 and 3). This size is considerably smaller than the CA125 immuwith the expression of CA125 in the cell lines as determined serologically and (iv) transfection of CA125 clone B53 into CA125-negative cell lines results in the expression of CA125 as detected by standard anti-CA125 antibodies. Moreover, this result supports earlier biochemical studies that had concluded that CA125 antigen is a mucin-type molecule (15). The cloned sequence is therefore designated as CA125/MUC16A. This gene has been provisionally localized to chromosome 19p13.3. Initially reported sequences of mucins are rarely full length because of the extremely large size of mucin mRNAs and not unexpectedly, no apparent 5' initiation signal is evident in the CA125/MUC16A cDNA sequence. The sequence is believed to be complete at the 3'-end as a stop codon, a polyadenylation site and a poly A tail have been identified (FIG. 2).

Mucins are notoriously difficult to clone because of their complex structure and high degree of glycosylation. Most successful cloning efforts have resulted from screening cDNA libraries with a polyclonal antiserum produced to the deglycosylated mucin (reviewed in 23–27). Thirteen human mucins have been cloned or partially cloned to date (MUC-1, -2, -3, -4, -5AC, -5B, -6, -7, -8, -9, -11, -12 and -13; refs. 23–29). In this study, however, a polyclonal antiserum to the native mucin was used to isolate a cDNA corresponding to the peptide moiety of CA125/MUC16 antigen. This approach may have been successful because of the relatively low content of serine and threonine (representing potential O-glycosylation sites) in CA125/MUC16 in comparison with most other mucins. The high degree of purity of the isolated antigen, as well as the use of a highly absorbed antiserum and the high expression of CA125 in the OVCAR-3 cell line used to produce the cDNA library, may also have been key factors in obtaining positive clones.

The deduced amino acid sequence of CA125/MUC16A resembles other mucins in having serine, threonine and proline as major amino acids; however, its high content of leucine is characteristic of MUC16. The presence of tandem repeats is also typical of mucins but the length of the repeat units (156 amino acids) is unusual, with only MUC6 having longer tandem repeats (30). Nine TRs have been identified thus far, with the last repeat being shorter than the others. The amino acid sequences in the TRs are not perfectly conserved, although 81 positions have conserved amino acids and certain motifs e.g. GPLYSCRLTLLR, ELGPYTL, FTLNFTIXNL and PGSRKFNXT, are found in all or most of the TRs. Two closely spaced cysteine residues (20 amino acids apart), which could form interchain disulfide bonded loops in the structure, are also perfectly conserved.

Serine and threonine residues, representing potential O-glycosylation sites, are scattered throughout the sequence but blocks of clustered Ser and Thr residues are evident in the TR region. These regions have adjacent or nearby Pro residues—a motif that is frequently found in O-glycosylation sites (19). One short serine/threonine-rich sequence (PTSSSST) is also found in the C-terminal non-TR region. Numerous potential N-glycosylation sites (Asn-X-Ser/Thr, where X is any amino acid except Pro) are also found in the sequence, including two that are perfectly conserved in the TR region. It is unlikely, however, that many of these sites are used as the content of N-linked glycan chains in purified CA125 is very low (15). It is also interesting to note that the sequence contains numerous lysine and arginine residues that are remote from the postulated O-glycosylation sites and which could explain the sensitivity of CA125 to trypsin digestion (16). Searching for conserved domains in the NCBI Blast site revealed the presence of six SEA domains in the deduced protein sequence. The significance of this finding is unclear. Five of the domains are in the tandem repeat region and one is in the non-tandem repeat region (amino acids 1709–1768). SEA domains were originally described as being characteristic of membrane-bound proteins with high levels of O-glycosylation (31); CA125/MUC16A certainly fits this description. Recently, it has been suggested that they also designate regions susceptible to proteolytic cleavage (32).

Two features of the non-TR region are particularly interesting. First, is the presence of a 25-amino- acid block of hydrophobic amino acids which could represent a membrane-spanning region. Transmembrane (TM) motifs have been found in five other mucins (MUC-1, -3, -4, -12 and 13). The remainder of the mucins that have been cloned lack TM regions and instead have cysteine-rich regions with homology to van Willebrand factor (27). Members of this family of mucins are secreted and form gels that protect and lubricate epithelial tissues. CA125 is also secreted from ovarian tumors and cell lines but the mechanism for its secretion is unclear. Two possibilities can be suggested—(i) a proteolytic event, possibly in the C-terminal SEA domain, cleaves off the luminal N-terminal domain (as in MUC1, refs. 33, 34) or (ii) alternatively-spliced mRNAs are generated that lack the TM region. Indeed, recent sequencing of clones B30 and B22 indicates the existence of such sequences (data not shown). The second feature of interest in the non-TR sequence is a short cytoplasmic tail (31 amino acid) that contains a putative tyrosine phosphorylation site (RRKKEGEY). This sequence is conserved in the translated mouse EST (AK003577) that has homology with CA125/MUC16A at the C-terminal end. MUC-1 has several tyrosine residues in its cytoplasmic tail and at least one of these is phosphorylated in vivo (35, 36). One of the Tyr residues in MUC1 occurs in a YTNP sequence, a motif that is responsible for binding to SH2 domains in proteins involved in intracellular signaling. The putative phosphorylation site found in CA125/MUC16A was first recognized in src family proteins (19, 20). Whether or not this tyrosine residue is phosphorylated in CA125 antigen is not known. Fendrick et al. (37) reported the presence of phosphate in CA125 from WISH cells by labeling with $^{32}PO_4^=$ and immunoprecipitation analysis but concluded that the phosphorylation site(s) are on Ser or Thr. Significantly, however, the secretion of CA125 is stimulated by epidermal growth factor (EGF), presumably through the EGF receptor which is a well-known tyrosine kinase (37). The possibility that CA125/MUC16 is phosphorylated on tyrosine and is involved in intracellular signaling needs further investigation. Interestingly, no EGF domains, which are found in some other mucins (MUC3, MUC4, MUC12 and 13), were located in CA125 (MUC16).

The molecular cloning of CA125 antigen opens the way to a better understanding of this important antigen, including its physiological function and its role in the biology of ovarian cancer. Of immediate interest will be the identification of the epitope(s) recognized by the various monoclonal antibodies that recognize CA125 (38). The identification of tandem repeats in the MUC16A/CA125 structure is consistent with the use of a single monoclonal antibody in double-determinant assays for CA125 levels, which would indicate that the antigen has multiple, identical epitopes (2). Such studies could lead to improvements in the CA125 assay for the detection of ovarian cancer.

REFERENCES

1. Bast, R. C., Jr., Feeney, M., Lazarus, H., Nadler, L. M., Colvin, R. C. and Knapp, R. C. (1981) *J. Clin. Invest.* 68, 1331–1337
2. Bast, R. C., Jr., Klug, T. L., St John, E., Jenison, E., Niloff, J. M., Lazarus, H., Berkowitz, R. S., Leavitt, T., Griffiths, C. T., and Parker, L., et al. (1983) *N. Engl. J. Med.* 309, 883–887
3. Bast, R. C., Jr., Xu, F. -J., Yu, Y. H., Barnhill, S., Zhang, Z., and Mills, G. B. (1998) *Int. J. Biol. Markers* 13, 179–187
4. Verheijen, R. H., Von Mensdorff-Pouilly, S., Van Kamp, G. J., and Kenemans, P. (1999) *Sem. Cancer Biol.* 9, 117–124
5. Menon, U. and Jacobs, I. J. (2000) *Curr. Opin. Obstet. Gynecol.* 12, 39–42
6. Meyer, T. and Rustin, G. J. (2000) *Br. J. Cancer* 82, 1535–1538
7. Meden, H. and Fattahi-Meibodi, A. (1998) *Int. J. Biol. Markers* 13, 231–237
8. O'Brien, T. J. (1998) *Int. J. Biol. Markers* 13, 188–195
9. Davis, H. M., Zurawski, V. R., Bast, R. C., Jr., and Klug, T. L. (1986) *Cancer Res.* 46, 6143–6148
10. Matsuoka, Y., Nakashima, T., Endo, K., Yoshida, T., Kunimatsu, M., Sakahara, H., Koizumi, M., Nakagawa, T., Yamaguchi, N. and Torizuka, K. (1987) *Cancer Res.* 47, 6335–6340
11. Nagata, A., Hirota, N., Sakai, T., Fujimoto, M., and Komoda, T. (1991) *Tumour Biol.* 12, 279–286
12. de los Frailes, M. T., Stark, S., Jaeger, W., Hoerauf, A., and Wildt, L. (1993) *Tumour Biol.* 14, 18–29

13. Kobayashi, H., Ida, W., Terao, T., and Kawashima, Y. (1993) *Am. J. Obstet. Gynecol.* 169, 725–730
14. Zurawski, V. R., Jr., Davis, H. M., Finkler, N. J., Harrison, C. L., Bast, R. C., Jr., and Knapp, R. C. (1988) *Cancer Rev.* 11–12, 102–118
15. Lloyd, K. O., Yin, B. W. T., and Kudryashov, V. (1997) *Int. J. Cancer* 71, 842–850
16. Lloyd, K. O. and Yin, B. W. T. (2001) *Tumor Biol.* 22, 77–82
17. Campbell, I. G., Campbell, I. G., Foulkes, W. D., Senger, G., Stamp, G. W., Allan, G., Boyers, C., Jones, K., Bast, R. C., Jr., and Solomon, E. (1994) *Hum. Mol. Gen.* 3, 589–594
18. Chambers, J. A. and Solomon, E. (1996) *Genomics* 38, 305–313
19. Hansen, J. E., Lund, O., Engelbrecht, J., Bohr, H., Nielsen, J. O., Hansen, J. -E. S., and Brunak, S. (1995) *Biochem. J.* 308, 801–813
20. Patschinsky, T., Hunter, T., Esch, F. S., and Cooper, J. A. (1982) *Proc. Natl. Acad. Sci. USA* 79, 973–977
21. Cooper, J. A., Esch, F. S., Taylor, S. S., and Hunter, T. (1984) *J. Biol. Chem* 259, 7835–7841
22. Lloyd, K. O., Yin, B. W. T., Tempst, P., and Erdjument-Bromage, H. (2000) *Biochim. Biophys. Acta Gen. Subj.* 1474, 410–414
23. Taylor-Papadimitriou, J. and Gendler, S. J. (1988) *Cancer Rev.* 11–12, 11–24.
24. Kim, Y. S., Gum, J. R., Jr., Byrd, J. C., and Toribara, N. W. (1991) *Am. Rev. Respir. Dis.* 144 Suppl., S10-S14
25. Gendler, S. J. and Spicer, A. P. (1995) *Annu. Rev. Physiol.* 57, 607–634
26. Seregni, E., Botti, C., Massaron, S., Lombardo, C., Capobianco, A., Bogni, A., and Bombardier, E. (1997) *Tumori* 83, 625–632
27. Perez-Vilar, J. and Hill, R. L. (1999) *J. Biol. Chem.* 274, 31751–31754
28. Williams, S. J., McGuckin, M. A., Gotley, D. C., Eyre, H. J., Sutherland, G. R., and Antalis, T. M. (1999) *Cancer Res.* 16, 4083–4089.
29. Williams, S. J., Wreschner, D. H., Tran, M., Eyre, H. J., Sutherland, G. R., and McGuckin, M. A. (2001) *J. Biol. Chem.*—in press
30. Toribara, N. W., Roberton, A. M., Ho, S. B., Kuo, W.-L., Gum, E., Hicks, J. W., Gum, J. R., Jr., Byrd, J. C., Siddiki, B., and Kim, Y. S. (1993) *J. Biol. Chem.* 268, 5879–5885
31. Bork, P. and Patthy, L. (1995) *Protein Sci.* 49, 1421–1425.
32. Wreischner, D. H., Keydar, I., Yoeli, M., Okun, L., Ziv, R., William, S., and McGuckin (2000). *Proc. 6th Int. Workshop on Carcinoma-associated Mucins,* Cambridge, UK. p. 25.
33. Ligtenberg, M. J., Kruijshaar, L., Buijs, F., van Meijer, M., Litvinov, S. V., and Hilkens, J. (1992) *J. Biol. Chem* 267, 6171–6177
34. Boshell, M., Lalani, E. -N., Pemberton, L., Burchell, J., Gendler, S., and Taylor-Papadimitriou, J. (1992) *Biochem. Biophys. Res. Commun.* 185, 1–8
35. Zrihan-Licht, S., Baruch, A., Elroy-Stein, O., Keydar, I., and Wreschner, D. H. (1994) *FEBS Lett.* 356, 130–136
36. Pandey, P., Kharbanda, S., and Kufe, D. (1995) *Cancer Res.* 55, 4000–4003
37. Fendrick, J. L., Konishi, I., Geary, S. M., Parmley, T. H., Quirk, J. G., Jr., and O'Brien, T. J. (1997) *Tumour Biol.* 18, 278–289
38. Nustad, K., Bast, R. C., Jr., O'Brien, T. J., Nilsson, O., Seguin, P., Suresh, M. R., Saga, T., Nozawa, S., Bermer, O. P., and de Bruijn, H. W. A., Nap, M., Vitali, A., Gadnell, M., Clark, J., Shigemasa, K., Karlsson, B., Kreutz, F. T., Jette D., Sakahara, H., Endo, K., Paus, E., Warren, D., Hammarstrom, S., Kenemans, P., and Hilgers, J. (1996) *Tumour Biol.* 17, 196–219

Second Series of Experiments

Identification of a Form of the CA125 Ovarian Cancer Antigen (MUC16B) Lacking a Transmembrane Sequence CA125 antigen is overexpressed in the majority of human ovarian carcinomas and is released into the blood stream where it can be detected with suitable immunological assays (1). Approximately 80% of patients with ovarian cancer have elevated serum CA125 levels and the measurement of these levels is a valuable tool for monitoring the clinical status of ovarian cancer patients (2,3).

Despite the widespread use of CA125 as a serum marker, until recently, very little information was available on the molecular nature of the CA125 antigen. Biochemical studies had indicated that the antigen is a large, highly glycosylated glycoprotein with mucin-like characteristics (4–6). This suggestion has now been confirmed by the molecular cloning of CA125 (gene designation: MUC16) by the inventors (7,8) and O'Brien and coworkers (9). Both groups reported a long DNA species that coded for a protein with a large number of partially-conserved, 156 amino acid-long tandem repeat (TR) sequences. These tandem repeats contain a serine, threonine and proline-rich (S/T-rich) area that is a potential region of O-glycosylation. The molecule also contains a C-terminal non-TR region, a potential membrane-spanning sequence and a short cytoplasmic tail. O'Brien et al. (9) also reported a large N-terminal non-repetitive S/T/P-rich region in CA125.

The presence of a membrane-spanning region in MUC16A/CA125 raises the question as to the source of serum CA125 antigen. One possibility is that cell-bound CA125 is cleaved by a protease(s) and released into the surrounding medium. In support of this mechanism is the presence in the molecule of SEA motifs which are possible protease-sensitive sites (7,9). Another, not mutually exclusive, explanation is that MUC16/CA125 is also synthesised as a form lacking a transmembrane region that could be directly secreted from cells. During the original cloning of MUC16/CA125 we had isolated a small number of cDNA clones that appeared to differ from the reported clone (B4) in having a different 3' nucleotide sequence. We now show that these species represent a second form of MUC16/CA125 lacking a C-terminal membrane-spanning region that could be a secreted form of the antigen. This species (gene designation: MUC16B) also has a long serine/threonine-rich N-terminal sequence.

Experimental Procedures

Materials and Methods

The isolation of cDNA clones B4, B30 and B22 in the pBK-CMV vector has been described (7). Human tumor cell lines OVCAR3, SK-OV-8, COLO316, 2774, SK-OV-3 and SK-OV-8 (ovarian cancer cell lines), MCF-7 (breast cancer), IMR-32 (neuroblastoma), MKN45 (gastric cancer), and MCA (sarcoma) and their CA125 status have been described (7).

RT-PCR Procedure and cDNA Sequencing

Messenger RNA was isolated from cell pellets using a FastTrack 2.0 kit (Invitrogen Life Technologies, Carlsbad, Calif.). cDNA was then synthesised using a Superscript First Strand Synthesis kit as described by the manufacturer (Invitrogen). RT-PCR was performed as follows: 2 µl cDNA, 0.2 mM dNTP mix, 4 mM MgCl2, 0.4 to 1 µM forward or reverse primers and 2.5U Platinum Taq DNA Polymerae (Invitrogen) were mixed in a total volume of 50 µl and the samples were cycled as follows: 94° for 1 min., 25–35 cycles of 94° C. for 30 secs, 54–65° C. for 30secs and 72° C. for 30 secs to 3 min. and a final cycle of 94° C. fro 5 min. For the PCR of longer products (>5 kb) the LA PCR kit from Takara Shuzo Co. was used under following conditions: 94° C. for 1 min., followed by 30 cycles of 94° C. for 20 secs., 60° C. for 30 secs and 72° C. for 7 or 10 min. and a final cycle of 94° C. for 20 secs., 55 or 60° C. for 30 secs., and 72° C. for 10 min. RT-PCR products were analyzed by gel electrophoresis in 0.8 or 1.0% agarose in Tris-acetate -EDTA and stained with ethidium bromide.

For sequencing the PCR product was cloned into the Topo TA cloning vector from Invitrogen). Inserts were sequenced initially with T3 and T7 primers and then with suitable forward and reverse primers designed according to the derived sequence. Sequencing was performed either by our own sequencing facility or by the Cornell University Facility using a BigDye Terminator Primer Sequencing Kit (Perkin Elmer/ABI) in ABI 3700 or ABI 377 DNA seqenators. The sequences were aligned visually for the repeat region sequences and with the aid of Vector NT for other sequences.

3' and 5' RACE Procedures

These procedures were performed with the First Choice RLM-RACE kit (Ambion Colo., Austin Tex.) using suitable forward primers for the 3' and reverse primers for 5' region respectively. For the 5' RACE the outer gene-specific primer was 5'TCACAGTCCCTACATTGACTA3' and the inner primer was 5'CATGGCACATCTCCAGGA3'. The products were cloned into TA vector and sequenced as described above.

Results

Cloning and Sequencing of B30 cDNA

During the original expression cloning of MUC16A(7) we observed that the majority of the clones detected by screening the cDNA library with a rabbit antiserum were shorter forms of the longest clone (B4) reported (7) and contained varying numbers of TRs, a non-TR region, a potential TM region and a cytoplasmic tail. However a few clones were isolated that appeared to be different in that they lacked a restriction enzyme site (Xho) present in the B4 family of inserts. The cDNA from one of these clones (B30) was completely sequenced using the T3 primer of the vector initially and, subsequently, new forward and reverse primers derived from the less conserved regions of the new sequence. The B30 insert had a total of 4103 bp with a stop codon at 3593 bp. This was followed by 3' non-translated region and finally, a poly A sequence. Despite the presence of a poly-A sequence no obvious polyadenylation site was observed (FIG. 7). Clone B22 was partially sequenced and shown to be a shorter (2432 bp) form identical to the 3' sequence of B30.

Conceptual translation of the B30 sequence indicated a protein composed entirely of 7.7 TRs of 156 amino acids each. The 4.5 C-terminal repeats were identical to sequences found in the B4 clone and three new partially-conserved TRs were detected N-terminal to the B4 sequence. The new repeats contained the potential cysteine loop, the 2 conserved N-glycosylation sites and the serine/threonine-rich region found in clone B4 of MUC16. No non-TR, transmembrane or cytoplasmic sequences were present in this new species of MUC16. Searching the NCBI database with this sequence yielded two EST (BE005912 and BI016218)

corresponding to repeat number 3 in the B30 sequence. Surprisingly, no ESTs, or even genomic, sequences corresponding to the non-translated 3' region of B30 were detected in the NCBI databases. In order to confirm that the new form of MUC16 was not a cloning artifact 3' RACE was performed with RNA from the OVCAR3 cell line. Sequences corresponding to the last repeat and the untranslated region were identified (data not shown). We also examined a panel of cancer cells for transcripts corresponding to the 3' region by RT-PCR using primers from repeat 8 and the 3' end of the untranslated region of B30. PCR products were found only with mRNA from cells known to express CA125, again confirming the relationship of B30 to CA125.

Complete Sequence of MUC16B/CA125

Searching the NCBI genomic database with sequences derived from B30 indicated that numerous sequences related to this species were located on a genomic sequence file designated NT 025133.6 (FIG. 10). At present (March 2002), this region, located on chromosome 19 p13.3/p13.2, consists of 31 unordered sequences of varying length. This data does not allow the complete sequence of MUC16 to be easily assembled, however by designing suitable RT-PCR primers from the genomic sequence for RT-PCR it was possible to amplify and sequence cDNA that extended to the 5' of B30 by 6.5 partially conserved tandem repeat units (FIGS. 8 and 9) and a non-TR region. This results in the identification of a total of 14 repeats in the MUC16B sequence. Adjacent to the first exon of the 5'-most repeat sequence in NT 025133.6 we noticed a very long potential open reading frame. This region does not contain any repeat sequences but is rich in serine, threonine and proline residues. Also, in NT 025133.6 we observed a short putative exon containing the ATG sequence suggested by O'Brien et al. (9) to be the initiating codon of CA125 (FIG. 10). Again by designing suitable primers in this region, PCR products corresponding to this new 5' region were cloned and sequenced. The NCBI database contains a number of ESTs corresponding to portions of the 5' region of this sequence. One of these ESTs extended into the 5' region beyond the ATG designated by O'Brien et al. (9). In fact NT 025133.6 contains an extremely long potential open reading frame (positions 176,04,53–179,693) corresponding to this region. The Celera public access database also contains genomic sequence for this region and, significantly, has an extremely long hypothetical transcript sequence (hCT1645865) containing all the putative exons in 176,053–179,693 and 179,693–183,573 b.p. regions of NT 025133.6. Primers were also designed to sequence these regions and by application of RT-PCR to OVCAR-3 mRNA it was possible to confirm these sequences. Only minor differences between the experimentally-derived sequence and the data base sequences except for numerous differences in the 3' region of the serine/threonine-rich were it joins the tandem repeat region between the published data and our sequence. This long S/T/P-rich coding region has numerous ATG codons which could serve as initiation sites for mRNA synthesis (some of them fitting a Kozak consensus motif, ref. 10) so it was difficult to pick a likely site. Application of 5' RACE with a series of primers in different locations in the sequence finally yielded a primer that gave a clear cDNA product and sequencing of this product indicated a start site at position 261 (FIGS. 8 and 9). This ATG is located in a classical Kozak box. To confirm that the 5' S/T/P-coding region was in fact related to the tandem repeat region and codes for the CA125 antigen we performed RT-PCR on mRNA from a panel of cell lines (as we had done for the 3' end) with primers corresponding to a sequence close to the 5' end; the result showed a complete correlation between generation of the PCR product and expression of CA125 in these cell lines.

Conceptual translation of the assembled nucleotide sequence (18347 bp) demonstrated a protein of a maximum of 5935 amino acids, with several AUG in its 5' mRNA that could act as the translational starting site. MUC16B has an extremely long (approximately 3650 amino acids) S/T/P-rich N-terminal (containing 17.2% serine, 19.5% threonine and 9.0% proline) followed by a region of 14 partially-conserved repeats of 156 amino acids each as described above (FIG. 9). The sequence terminated after one of the S/T/P-rich regions in the last TR with no hydrophobic C-terminal transmembrane region being observed.

Discussion

Using a combination of expression cloning and RT-PCR approaches we have identified a new species of CA125 (designated MUC16B) that has a long serine/threonine-rich N-terminal region and a C-terminal region of 14 tandem repeats but no apparent transmembrane region. This product could therefore be a secreted form of CA125 although no secretory peptide sequence is present at the N-terminus. The tandem repeat region is similar in construction to the repeats previously observed in MUC16A/CA125. These repeats contain a small region rich in serine and threonine which could represent O-glycosylation sites. The N-terminal region has numerous serine and threonine residues scattered through the sequence and these could also be O-glycosylated. CA125 is known to be highly glycosylated (77% by weight) and most of this consists of O-glycosylated chains (4). Two conserved potential N-glycosylated sites occur in each tandem repeat and these could also contribute to the carbohydrate content of CA125, although this level is probably quite low (4).

At present it is unclear as to whether the CA125 molecules identified by the inventors (7,8) and O'Brien et al. (9) have the same long N-terminal sequence. O'Brien et al. (9) described a N-terminal sequence of 1638 amino acids in contrast to the 3756 amino acids or less depending which methionine is really used as a start site of the several possible ones) described here for MUC16B. However, the S/T/P-rich region was connected to the TR regions and the non-TR, trans-membrane and cytoplasmic regions similar to those reported by us in MUC16/CA125. Using 5' RACE they detected an initiating methionine (at position 6435 in FIG. 8) whereas we could detect such a site as early as in position 49. There were three other possible initiating methionines at positions 151, 261 and 279 which are shown as underlined in FIG. 9. Also unclear is whether either of the N-terminal S/T/P-rich sequences are present in the MUC16A/CA125 species reported previously as clone B4 was not complete at the 5' end (7). We were unable to generate products by performing RT-PCR with primers located in MUC16B repeat region and in the 3' portion of the MUC16 tandem repeats not found in MUC16B, indicating that MUC16A and MUC16B have different repeat sequences at their 5'-end and possibly, therefore, a shorter or different S/T-rich regions. Such a situation may account for the larger number of repeats that were identified by O'Brien et al. (9) and those that can be found in the genome data bases and not in MUC16B.

MUC16B/CA125 is an extremely long molecule with a peptide chain of 5935 amino acids or less (depending on which AUG of the several present at the 5' of the mRNA is used as the start site) and an expected Mr of about 600,000. Many other cloned mucins (11,12) also have extremely long peptide sequences, e. g. MUC5B has 5662 amino acids and a Mr of about 600,000 (13). By pulse-chase experiments we had previously identified a putative CA125 precursor species of about 400 kDa which, given the uncertainties inherent in very high molecular sizes determined by SDS-PAGE, is consistent with this result (5). It is also interesting to note that the precursor consisted of a doublet of two closely-spaced species on SDS-PAGE which could correspond to MUC16A and MUC16B (5).

Although MUC16B/CA125 has many of the attributes expected of a mucin species (i.e. large size, high serine, threonine and proline content, high level of O-glycosylation and presence of tandem repeats) it also has some unique features. These include the presence of potential cysteine loops in the repeat region and the segregation of the O-glycosylation sites into a small region of each repeat. Another unusual feature is that the repeat region is not coded by one long exon; rather each repeat unit contains 5 small exons [O'Brien et al. (9) and our unreported data]. In CA125 the longest exons are found at the 5' end and code for a non-repeat serine/threonine-rich region. Because of it large size CA125 is extremely difficult to isolate in an intact form from biological materials. In our original purification of CA125 we described an extremely large species migrating in the stacking gel of a SDS-PAGE gel (4), whereas subsequently we found smaller species migrating mainly in the upper region of the separating gel (7). Recently, in a report from the Third ISOBM Workshop (14) it was reported that CA125 can be degraded by sonication procedures, as well as by proteolytic digestion.

A summary of the information to be presented on MUC16A and MUC16B is shown in FIG. 11, where the schematic compares the two proteins. As indicated, MUC16A and MUC16B share identical sequence for at least 677 aa, corresponding to the 4.5 last TR of MUC16B. Because the N-term region of MUC16A is missing, the region of perfect homology between the two proteins could be larger. After the 4.5 identical TR in the two CA125 forms, MUC16B ends with a non homologous 16 aa C-term tail, while MUC16A extends its C-term region with another 4.5 TR followed by more than 400 aa of a non-TR region that contains a single transmembrane region and a short intra-cytoplasmic tail.

Another feature of CA125 that still needs to be elucidated is the location in the molecule of the antibody-detected epitopes. Presently available data indicated that they are mainly located in the tandem repeat regions of the molecule (8,9) and this would be consistent with the ability of a single antibody to useful in sandwich assays (1). Further work on this problem will be needed to further delineate the structures of the epitopes and whether more specific assays for CA125 can be devised. The molecular cloning of CA125 also opens up approaches to determining the function of CA125 and an understanding of its role in ovarian malignancy.

REFERENCES

1. Bast, R. C., Jr., Klug, T. L., St John, E., Jenison, E., Niloff, J. M., Lazarus, H., Berkowitz, R. S., Leavitt, T., Griffiths, C. T., and Parker, L., et al. (1983) N. Engl. J. Med. 309, 883–887

2. Bast, R. C., Jr., Xu, F. -J., Yu, Y. H., Barnhill, S., Zhang, Z., and Mills, G. B. (1998) Int. J. Biol. Markers 13, 179–187

3. Menon, U. and Jacobs, I. J. (2000) Curr. Opin. Obstet. Gynecol. 12, 39–42
4. Lloyd, K. O., Yin, B. W. T., and Kudryashov, V. (1997) Int. J. Cancer 71, 842–850
5. Lloyd, K. O. and Yin, B. W. T. (2001) Tumor Biol. 22, 77–82
6. O'Brien, T. J. (1998) Int. J. Biol. Markers 13, 188–195
7. Yin, B. W. T. (2001) J.Biol. Chem. 276, 27371–27375
8. Yin, B. W. T. Dnistrian A., and Lloyd, K. O.(2002) Int. J. Cancer 98, 737–740
9. O'Brien T. J. Beard, J. B., Underwood, L. J., Dennis, R. A., Santin, A. D., and York, 1. (2001) Tumor Biol. 22, 348–366
10. Kozak M. (1991) J. Biol. Chem. 266, 19867–19870 Gendler, S. J. and Spicert, A. P. (1995) Annu. Rev. Physiol. 57, 607–634
11. Perez-Villar, J. and Hill, R. L. (1999) J. Biol. Chem. 274, 31751–31754
12. Dessayn, J. -C., Buisine, M. -P., Porchet, N., Aubert, J.-P., and Laine, A. J. (1998) J. Biol. Chem. 273, 30157–30164
13. Nustad, K., Yenedin, Y. Lloyd, K. O., Shigemasa, K., de Bruijn, H. W. A. Jansson, B., Nilsson, O., O'Brien t. J. (2002) Tumor Biol.—in press

What is claimed is:

1. An isolated nucleic acid molecule consisting of SEQ. ID NO. 6 or 7.

2. An isolated nucleic acid molecule consisting of the sequence encoding CA125 protein, wherein the CA125 protein consists of SEQ. ID NO. 8.

3. The isolated nucleic acid molecule of claim 1, wherein the nucleic acid molecule is a RNA, cDNA, or synthetic DNA.

4. An expression vector comprising the nucleic acid molecule of claim 1, that when expressed is capable of producing CA125 protein consisting of SEQ. ID No. 8.

5. A composition comprising the isolated nucleic acid molecule consisting of SEQ. ID No. 6 or 7.

6. The composition of claim 5, wherein the nucleic acid molecule is a RNA, cDNA, or synthetic DNA.

* * * * *